US007422754B2

(12) United States Patent
Nassif et al.

(10) Patent No.: US 7,422,754 B2

(45) Date of Patent: Sep. 9, 2008

(54) ***NEISSERIA MENINGITIDIS* COMPOUNDS AND ANTI-INFECTION APPLICATIONS THEREOF**

(75) Inventors: Xavier Nassif, Paris (FR); Colin Tinsley, Paris (FR); Silke Klee, Berlin (DE); Mark Achtman, Berlin (DE); Petra Merker, Berlin (DE)

(73) Assignees: Institut National de la Sante et de la Recherche Medicale (Inserm), Paris (FR); Max-Planck Gesellschaft zur Forderung des Wissenschaften E.V., Munich (DE)

( * ) Notice: Subject to any disclaimer, the term of this patent is extended or adjusted under 35 U.S.C. 154(b) by 379 days.

(21) Appl. No.: 10/845,424

(22) Filed: May 14, 2004

(65) Prior Publication Data

US 2005/0089527 A1 Apr. 28, 2005

Related U.S. Application Data

(62) Division of application No. 10/030,740, filed as application No. PCT/EP00/06943 on Jul. 5, 2000, now abandoned.

(30) Foreign Application Priority Data

Jul. 13, 1999 (EP) .................................. 99401764

(51) Int. Cl.
*A61K 39/095* (2006.01)
*C12P 21/04* (2006.01)
*C07H 21/04* (2006.01)
*C12N 1/20* (2006.01)

(52) U.S. Cl. .................. 424/250.1; 435/69.1; 435/69.7; 435/252.3; 530/300; 530/350; 424/249.1; 424/190.1; 424/184.1; 536/23.1; 536/23.7

(58) Field of Classification Search ............. 424/250.1, 424/249.1, 184.1, 190.1; 530/300, 350; 536/23.1, 536/23.7; 435/69.1, 69.3, 252.3, 69.7
See application file for complete search history.

(56) References Cited

FOREIGN PATENT DOCUMENTS

| | | |
|---|---|---|
| WO | WO 90 04641 | 5/1990 |
| WO | WO 90 06696 | 6/1990 |
| WO | WO 92 03467 | 3/1992 |
| WO | WO 94 05326 | 3/1994 |
| WO | WO 97 28273 | 8/1997 |

OTHER PUBLICATIONS

Bowie et al (Science, 1990, 257:1306-1310); Roitt et al (Immunology, 1993, Mosby, St. Louis, p. 7.7-7.8.*

Herbert et al (The Dictionary of Immunology, Academic Press, 3rd Edition, London, 1985, pp. 58-59).*

Accession: B81989 Parkhill Nature 404, 502-506, 2000.*

Holmes (Exp. Opin.Invest. Drugs, 2001, 10(3):511-519).*

Nassif et al, "What do we know about the entry of *Neisseria meningitidis* into the meninges?", Bull. Ins. Pasteur, vol. 95, No. 4, 1997, pp. 219-235.

Ala'Aldeen, "Vaccines Against *Neisseria meningitidis*: Past, Present and Future", Biotecnologia Aplicada, vol. 13, No. 1, 1996, pp. 1-7.

Gomez et al, "Antigenicity, cross-reactivity and surface exposure of the *Neisseria meningitidis* 37 kDa protein (Fbp)", Vaccine, vol. 14, No. 14, 1996, pp. 1340-1346.

Sarkari et al, "Variable expression of the Opc outer membrane protein in *Neisseria meningitidis* is caused by size variation of a promoter containing poly-citidine", Molecular Microbiology, vol. 13, No. 2, 1994, pp. 207-217.

Maiden et al, "Multilocus sequence typing: a portable approach to the identification of clones within populations of pathogenic microorganisms" Proc. Natl. Acad. Sci. USA, vol. 95, Mar. 1998, pp. 3140-3145.

Watarai et al, "Disulfide oxidoreductase activity of *Shigella flexneri* is required for release of Ipa proteins and invasion of epithelial cells", Proc. Natl. Acad. Sci. U.S.A., vol. 92, 1995, pp. 4927-4931.

Peek et al, "Characterization of a periplasmic thiol:disulfide interchange protein required for the functional maturation of secreted virulence factors of *Vibrio chlorae*", Proc. Natl. Acad. Sci. U.S.A., vol. 89, 1992, pp. 6210-6214.

Jonson et al, "Cloning and sequencing of *Vibrio cholera* mannose-sensitive haemagglutinin pilin gene: localization of mshA within a cluster of type 4 pilin genes", Molecular Microbiology, vol. 13, No. 1, 1994, pp. 109-118.

Van der Ley et al, "Construction of *Neisseria meningitidis* strains carrying multiple chromosomal copies of the porA gene for use in the production of a multivalent outer membrane vesicle vaccine", Vaccine, vol. 13, No. 4, 1995, pp. 401-407.

Scheuerpflug et al, "Roles of PilC and PilE proteins in pilus-mediated adherence of *Neisseria gonorrhoea* and *Neisseria meningitidis* to human erythrocytes and endothelial and epithelial cells", Infection and Immunity, vol. 67, No. 2, Feb. 1999, pp. 834-843.

Stibitz et al, "Genetic analysis of a region of the *Bordetella pertussis* chromosome encoding filamentous hemagglutinen and the pleiotropic regulatory locus vir", Journal of Bacteriology, vol. 170, No. 7, Jul. 1988, pp. 2904-2913.

Virji et al, "Variations in the expression of pili: the effect on adherence of *Neisseria meningitidis* to human epithelial and endothelial cells", Molecular Microbiology, GB, Oxford, vol. 6, No. 10, 1992, pp. 1271-1279.

Zhou et al, "Sequence diversity within the argF, fbp and recA genes of natural isolates of *Neisseria meningitidis*: interspecies recombination within the argF gene", Molecular Microbiology, vol. 6, No. 15, 1992, pp. 2135-2146.

(Continued)

*Primary Examiner*—Shanon A. Foley
*Assistant Examiner*—Padma v Baskar
(74) *Attorney, Agent, or Firm*—Nixon & Vanderhye P.C.

(57) ABSTRACT

The invention provides novel *Neisseria meningitides* (Nm) polypeptides and polynucleotides which cover the Nm genetic diversity, and which correspond to polypeptide of Nm outer membrane and/or periplasma, and to methods for producing such Nm compounds. Also provided are anti-Nm infection, and particularly diagnostic. prophylactic and therapeutic uses thereof.

5 Claims, 163 Drawing Sheets

OTHER PUBLICATIONS

Figure 46:
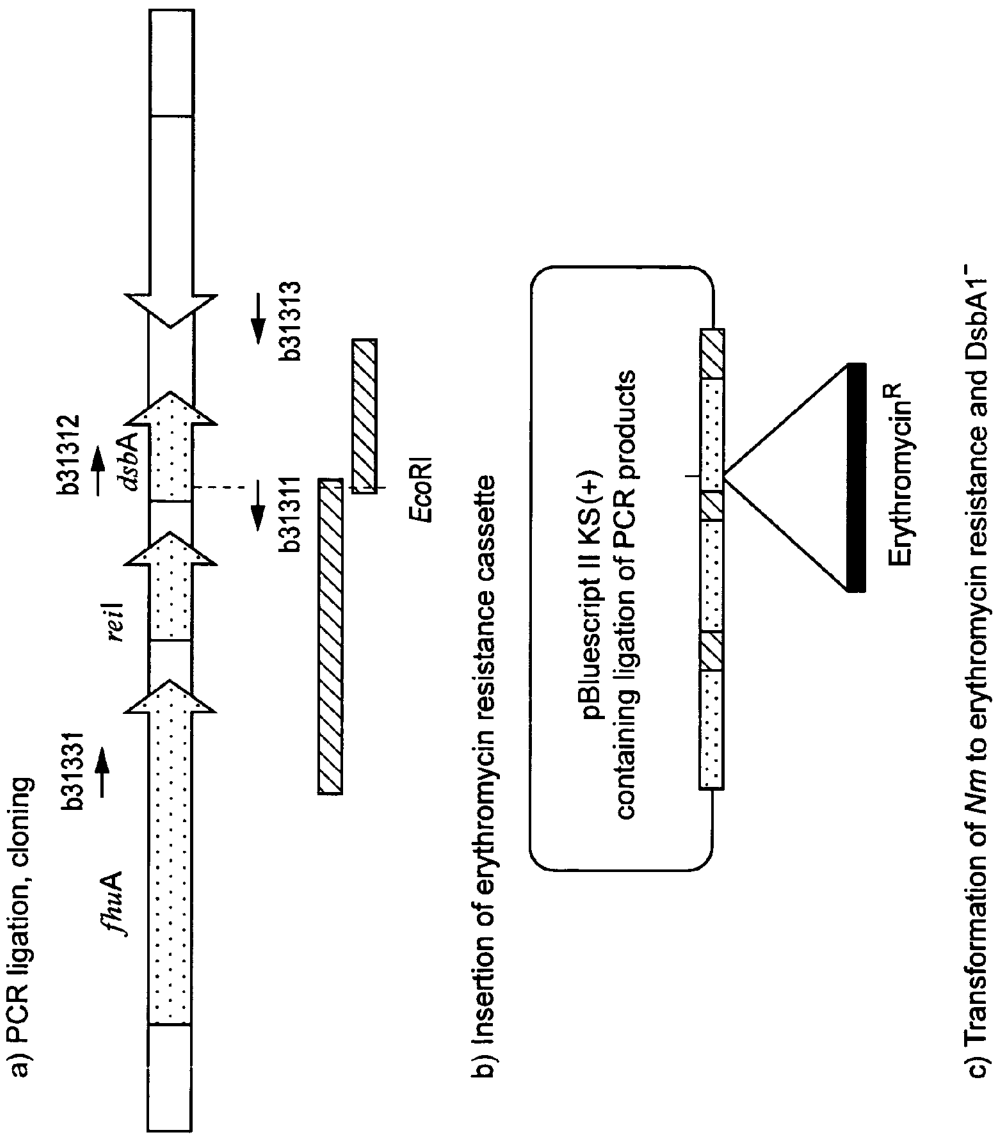

Barenkamp et al, "Cloning, Expression, and DNA Sequence Analysis of Genes Encoding Nontypeable *Haemophilus influenzae* High-Molecular-Weight Surface-Exposed Proteins Related to Filamentous Hemagglutinin of *Bordetella pertussis*", Inflection and Immunity, US, American Society for Microbiology, Washington, vol. 60, No. 4, Apr. 1, 1992, pp. 1302-1313.

Salit et al, "Adherence of *Neisseria meningitidis* to human epithelial cells", Infection and Immunity, vol. 31, No. 1, Jan. 1981, pp. 430-435.

EMBL databases; Heidelberg, Germany, May 18, 1999, "*Neisseria meningitidis* NatD (natD) and NatC (natC) genes, complete cds.", abstract.

Stone et al, "*Salmonella enteritidis* has a homologue of tolC that is required for virulence in BALB/c mice", Molecular Microbiology, vol. 17, No. 4, 1995, pp. 701-712.

* cited by examiner

*Fig. 1A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 1A-1*

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 1B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 2A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 2A-1*

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 2B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 3A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 3A-1*

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 3B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 4A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 4A-1*

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 4B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 5A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 5A-1*

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 5B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 6A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 6A-1*

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 6B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 7A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 7A-1*

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 7B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

Fig. 8A

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 8A-1*

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 8B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 9A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

*Fig. 9A-1*

551 TGACCAATAA ATTCCAAATC AGCGGCACAC CGACTGTGAT TGTCGGCGGC

601 AAATACCAAG TTGAATTTAA AGACTGGCAG TCTGGTATGA CCACGATTGA

651 CCAGTTGGTG GATAAAGTAC GCGAAGAGCA GAAAAAGCCG CAATAA

*Fig. 9B*

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 10A*

1 ATGAAACTGA AAACCTTAGC TTTGACTTCA TTGACCCTGT TGGCATTGGC

51 CGCTTGTAGC AAACAGGCTG AAACCAGTGT TCCGGCAGAC AGCGCCCAAA

101 GCAGCTCATC TGCTCCGGCA GCCCCTGCTG AGTTGAACGA AGGTGTGAAC

151 TACACTGTAT TGTCTACGCC TATTCCGCAA CAGCAGGCCG GTAAAATCGA

201 AGTATTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

Fig. 10A-1

551 TGACCAATAA ATTCCAAATC AGCGGCACAC CGACTGTGAT TGTCGGCGGC

601 AAATACCAAG TTGAATTTAA AGACTGGCAG TCTGGTATGA CCACGATTGA

651 CCAGTTGGTG GATAAAGTAC GCGAAGAGCA GAAAAAGCCG CAATAA

Fig. 10B

1 MKLKTLALTS LTLLALAACS KQAETSVPAD SAQSSSSAPA APAELNEGVN

51 YTVLSTPIPQ QQAGKIEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

*Fig. 11A*

1 ATGAAACTGA AAACCTTAGC TTTGACTTCA TTGACCCTGT TGGCATTGGC

51 CGCTTGTAGC AAACAGGCTG AAACCAGCGT TCCGGCAGAC AGCGTCCAAA

101 GCAGCTCATC TGCTCCGGCA GCCCCAGCCC CATTGACCGA AGGCGTGAAC

151 TACACTGTAT TGTCCACGCC TATCCCGCAA CAGCAGGCCG GCAAAGTCGA

201 AGTCTTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTTCTGAAA GCCAAGCGCG TGCGGCTCAA ATGGAAGAGT

*Fig. 11A-1*

551 TGACCAATAA ATTCCAAATC AGCGGCACAC CGACTGTGAT CGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 11B*

1 MKLKTLALTS LTLLALAACS KQAETSVPAD SVQSSSSAPA APAPLTEGVN

51 YTVLSTPIPQ QQAGKVEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE ASESQARAAQ MEELTNKFQI SGTPTVIVGG

201 KYQVEFKDWQ SGMTTIDQLV DKVREEQKKP Q*

*Fig. 12A*

1 ATGAAACTGA AAACCTTAGC TTTGACTTCA TTGACCCTGT TGGCATTGGC

51 CGCTTGTAGC AAACAGGCTG AAACCAGCGT TCCGGCAGAC AGCGTCCAAA

101 GCAGCTCATC TGCTCCGGCA GCCCCAGCCC CATTGACCGA AGGCGTGAAC

151 TACACTGTAT TGTCCACGCC TATCCCGCAA CAGCAGGCCG GCAAAGTCGA

201 AGTCTTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTTCTGAAA GCCAAGCGCG TGCGGCTCAA ATGGAAGAGT

*Fig. 12A-1*

551 TGACCAATAA ATTCCAAATC AGCGGCACAC CGACTGTGAT CGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

*Fig. 12B*

1 MKLKTLALTS LTLLALAACS KQAETSVPAD SVQSSSSAPA APAPLTEGVN

51 YTVLSTPIPQ QQAGKVEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE ASESQARAAQ MEELTNKFQI SGTPTVIVGG

201 KYQVEFKDWQ SGMTTIDQLV DKVREEQKKP Q*

Fig. 13A

1 ATGAAACTGA AAACCTTAGC TTTGACTTCA TTGACCCTGT TGGCATTGGC

51 CGCTTGTAGC AAACAGGCTG AAACCAGCGT TCCGGCAGAC AGCGTCCAAA

101 GCAGCTCATC TGCTCCGGCA GCCCCAGCCC CATTGACCGA AGGCGTGAAC

151 TACACTGTAT TGTCCACGCC TATCCCGCAA CAGCAGGCCG GCAAAGTCGA

201 AGTCTTGGAA TTTTTCGGCT ACTTCTGCCC GCATTGCGCC CATCTTGAGC

251 CGGTCTTGAG CGAGCACATC AAAACGTTTA AAGACGATAC CTATATGCGC

301 CGGGAGCATG TCGTGTGGGG TGATGAAATG AAACCTTTGG CACGTTTGGC

351 GGCCGCAGTG GAAATGGCCG GTGAATCAGA TAAAGCCAAC AGCCATATTT

401 TCGATGCGAT GGTTAATCAA AAAATCAATC TGGCCGATAC CGATACCCTG

451 AAAAAATGGC TGTCCGAGCA AACAGCGTTT GACGGCAAAA AAGTATTGGC

501 TGCATTTGAG GCTCCTGAAA GCCAAGCGCG TGCGGCTCAA ATGGAAGAGT

Fig. 13A-1

551 TGACCAATAA ATTCCAAATC AGCGGCACAC CGACTGTGAT TGTCGGCGGC

601 AAATACCAAG TTGAATTTAA AGACTGGCAG TCCGGTATGA CCACGATTGA

651 CCAGTTGGTG GATAAAGTAC GCGAAGAGCA GAAAAAGCCG CAATAA

Fig. 13B

1 MKLKTLALTS LTLLALAACS KQAETSVPAD SVQSSSSAPA APAPLTEGVN

51 YTVLSTPIPQ QQAGKVEVLE FFGYFCPHCA HLEPVLSEHI KTFKDDTYMR

101 REHVVWGDEM KPLARLAAAV EMAGESDKAN SHIFDAMVNQ KINLADTDTL

151 KKWLSEQTAF DGKKVLAAFE APESQARAAQ MEELTNKFQI SGTPTVIVGG

201 KYQVEFKDWQ SGMTTIDQLV DKVREEQKKP Q*

*Fig. 14A*

1 GAGTATGCTC TTAGAGAAAA ATTGATCAAA AAAGCCAAAG GGAAAGGCCT

51 ATTATCTTTA GATTGGGGCA GCCTGACCGA ACAAGAGGCA AGGCAGTTTA

101 TCTATTTGAT TGAGAAAGAT CGATATTCTA ATCAATTGCT TGACCGATAT

151 CAAAAAAATC CAAGTAGTTT AAATAATCAA GAAAAAAATA TTCTTGCATA

201 TTTTATTAAC CAAACCTCTG GAGGTAACAC AGCTTGGGCA GCTTCGATAC

251 TGAAAACGCC CCAGTCAATG GGTAATCTCA CTATTCCTTC CAAAGATATT

301 AATAACACCT TATCGAAAGC CTATCAAACA TTGAGTCGTT ATGATTCTTT

351 TGATTACAAA TCAGCTGTTG CCGCACAACC TGCACTTTAC TTATTAAACG

401. GACCGCTTGG CTTCAGTGTC AAAGCAGCTA CTGTGGCAGC AGGAGGATAT

451 AACATTGGAC AGGGAGCGAA AGCAATCTCT AATGGAGAAT ATCTGCATGG

501 TACAGTTCAG GTTGTTAATG GCACATTGAT GGTTGCAGGA TCTGTATCTG

551 CACAGGCTGC AATATCGGCC AAGCCTGCAC CTGTTACCCG TTATCTGAGC

601 AATGACAGTG CTCCTGCTTT AAGACAAGCT TTAACTGCTG AAAGCCAGAG

651 AATCCGCATG AAACTGCCGG AAGAGTATCG ACAAATAGGG AATCTTGCGA

701 TAGCAAAAAT TGATGTTAAA GGATTACCGC AAAGGATGGA AGCATTTAGT

*Fig. 14A-1*

751 TCTTTCCAAA AAGGGGAACA TGGATTTATT TCGTTACCTG AAACAAAAAT

801 TTTTAAACCT ATATCTGTTG ATAAATATCA TAATATTGCC TCTCCTCCTA

851 GAGGAACATT AAGAAATATA GATGGAGAAT ATAAATTACT TGAAACTATA

901 GCACAGCAAC TCGGAAATAA TCGTAATGTA TCAGGTAGAA TTGATCTATT

951 TACAGAATTA AAGGCCTGTC AATCTTGCAG CAATGTTATT TTAGAGTTTA

1001 GAAATCGCTA TCCAAATATT CAATTAAATA TTTTTACAGG AAAATAG

*Fig. 14B*

1 EYALREKLIK KAKGKGLLSL DWGSLTEQEA RQFIYLIEKD RYSNQLLDRY

51 QKNPSSLNNQ EKNILAYFIN QTSGGNTAWA ASILKTPQSM GNLTIPSKDI

101 NNTLSKAYQT LSRYDSFDYK SAVAAQPALY LLNGPLGFSV KAATVAAGGY

151 NIGQGAKAIS NGEYLHGTVQ VVNGTLMVAG SVSAQAAISA KPAPVTRYLS

201 NDSAPALRQA LTAESQRIRM KLPEEYRQIG NLAIAKIDVK GLPQRMEAFS

251 SFQKGEHGFI SLPETKIFKP ISVDKYHNIA SPPRGTLRNI DGEYKLLETI

301 AQQLGNNRNV SGRIDLFTEL KACQSCSNVI LEFRNRYPNI QLNIFTGK

Fig. 15A

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG CACGAACGAT TTGAGTTCCA TCCTCGAAGG CAATGCCGGC

301 ATCGACGCCG CCTACGATAT GCGCGGCGAA AGCATTTTCC TGCGCGGCTT

351 TCAAGCCGAC GCATCTGATA TTTACCGCGA CGGCGTACGC GAAAGCGGGC

401 AGGTGCGCCG TAGCACCGCC AACATCGAGC GCGTGGAAAT CCTGAAAGGT

451 CCGTCCTCCG TGCTTTATGG GCGTACCAAC GGCGGCGGTG TCATCAACAT

501 GGTCAGCAAA TACGCCAACT TCAAACAAAG CCGTAATATC GGTACGGTTT

*Fig. 15A-1*

551 ATGGTTCGTG GGCAAACCGC AGCCTGAATA TGGACATCAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGTTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA CTTAACGCTC

1051 AACGGCGACT ACACCATCGG CCGTTTTGAA AACCACCTGA CCGTAGGCAT

1101 GGATTACAGC CGCGAACACC GCAACCCGAC ATTGGGTTTC AGCAGCGCCT

*Fig. 15A-2*

1151 TTTCCGCCTC CATCAACCCC TACGACCGCG CAAGCTGGCC GGCTTCGGGC

1201 AGATTGCAGC CTATTCTGAC CCAAAACCGC CACAAAGCCG ACTCCTACGG

1251 CATCTTTGTG CAAAACATCT TCTCCGCCAC GCCCGATTTG AAATTCGTCC

1301 TCGGCGGCCG TTACGACAAA TACACCTTTA ATTCCGAAAA CAAACTCACC

1351 GGCAGCAGCC GCCAATACAG CGGACACTCG TTCAGCCCCA ACATCGGCGC

1401 AGTGTGGAAC ATCAATCCCG TCCACACACT TTACGCCTCG TATAACAAAG

1451 GCTTCGCGCC TTATGGCGGA CGCGGCGGCT ATTTGAGCAT CGATACGTTG

1501 TCTTCCGCCG TGTTCAACGC CGACCCCGAG TACACCCGCC AATACGAAAC

1551 CGGCGTGAAA AGCAGTTGGC TGGACGACCG CCTCAGCACT ACGTTGTCTG

1601 CCTACCAAAT CGAACGCTTC AATATCCGCT ACCGCCCCGA TCCAAAAAAC

1651 AACCCTTATA TTTATGCGGT TAGCGGCAAA CACCGTTCGC GCGGCGTGGA

1701 ATTGTCCGCC ATCGGGCAAA TCATCCCCAA AAAACTCTAT CTGCGCGGTT

*Fig. 15A-3*

1751 CGTTGGGCGT GATGCAGGCG AAAGTCGTTG AAGACAAAGA AAATCCCGAC

1801 CGAGTGGGCA TCCATTTGAA TAACACCAGC AACGTTACCG GCAACCTGTT

1851 TTTCCGTTAT ACCCCGACCG AAAACCTCTA CGGCGAAATC GGCGTAACCG

1901 GTACAGGCAA ACGCTACGGT TACGACTCAA GAAATAAAGA AGTGACTACG

1951 CTTCCAGGCT TTGCCCGAGT TGATGCCATG CTTGGCTGGA ACCATAAAAA

2001 TGTTAACGTT ACCTTTGCCG CAGCCAATCT GTTCAATCAA AAATATTGGC

2051 GTTCGGACTC TATGCCGGGT AATCCGCGCG GCTATACTGC CCGGGTAAAT

2101 TACCGTTTCT GA

*Fig. 15B*

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GTVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNLTL

351 NGDYTIGRFE NHLTVGMDYS REHRNPTLGF SSAFSASINP YDRASWPASG

401 RLQPILTQNR HKADSYGIFV QNIFSATPDL KFVLGGRYDK YTFNSENKLT

451 GSSRQYSGHS FSPNIGAVWN INPVHTLYAS YNKGFAPYGG RGGYLSIDTL

501 SSAVFNADPE YTRQYETGVK SSWLDDRLST TLSAYQIERF NIRYRPDPKN

*Fig. 15B-1*

551 NPYIYAVSGK HRSRGVELSA IGQIIPKKLY LRGSLGVMQA KVVEDKENPD

601 RVGIHLNNTS NVTGNLFFRY TPTENLYGEI GVTGTGKRYG YDSRNKEVTT

651 LPGFARVDAM LGWNHKNVNV TFAAANLFNQ KYWRSDSMPG NPRGYTARVN

701 YRF*

Fig. 16A

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG CACGAACGAT TTGAGTTCCA TCCTCGAAGG CAATGCCGGC

301 ATCGACGCCG CCTACGATAT GCGCGGCGAA AGCATTTTCC TGCGCGGCTT

351 TCAAGCCGAC GCATCTGATA TTTACCGCGA CGGCGTACGC GAAAGCGGGC

401 AGGTGCGCCG TAGCACCGCC AACATCGAGC GCGTGGAAAT CCTGAAAGGT

451 CCGTCCTCCG TGCTTTATGG GCGTACCAAC GGCGGCGGTG TCATCAACAT

501 GGTCAGCAAA TACGCCAACT TCAAACAAAG CCGTAATATC GGTACGGTTT

*Fig. 16A-1*

551 ATGGTTCGTG GGCAAACCGC AGCCTGAATA TGGACATCAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGTTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA CTTAACGCTC

1051 AACGGCGACT ACACCATCGG CCGTTTTGAA AACCACCTGA CCGTAGGCAT

1101 GGATTACAGC CGCGAACACC GCAACCCGAC ATTGGGTTTC AGCAGCGCCT

Fig. 16A-2

1151 TTTCCGCCTC CATCAACCCC TACGACCGCG CAAGCTGGCC GGCTTCGGGC

1201 AGATTGCAGC CTATTCTGAC CCAAAACCGC CACAAAGCCG ACTCCTACGG

1251 CATCTTTGTG CAAAACATCT TCTCCGCCAC GCCCGATTTG AAATTCGTCC

1301 TCGGCGGCCG TTACGACAAA TACACCTTTA ATTCCGAAAA CAAACTCACC

1351 GGCAGCAGCC GCCAATACAG CGGACACTCG TTCAGCCCCA ACATCGGCGC

1401 AGTGTGGAAC ATCAATCCCG TCCACACACT TTACGCCTCG TATAACAAAG

1451 GCTTCGCGCC TTATGGCGGA CGCGGCGGCT ATTTGAGCAT CGATACGTTG

1501 TCTTCCGCCG TGTTCAACGC CGACCCCGAG TACACCCGCC AATACGAAAC

1551 CGGCGTGAAA AGCAGTTGGC TGGACGACCG CCTCAGCACT ACGTTGTCTG

1601 CCTACCAAAT CGAACGCTTC AATATCCGCT ACCGCCCCGA TCCAAAAAAC

1651 AACCCTTATA TTTATGCGGT TAGCGGCAAA CACCGTTCGC GCGGCGTGGA

1701 ATTGTCCGCC ATCGGGCAAA TCATCCCCAA AAAAACTCTA TCTGCGCGGT

*Fig. 16A-3*

1751 TCGTTGGGCG TGATGCAGGC GAAAGTCGTT GAAGACAAAG AAAATCCCGA

1801 CCGAGTGGGC ATCCATTTGA ATAACACCAG CAACGTTACC GGCAACCTGT

1851 TTTTCCGTTA TACCCCGACC GAAAACCTCT ACGGCGAAAT CGGCGTAACC

1901 GGTACAGGCA AACGCTACGG TTACGACTCA AGAAATAAAG AAGTGACTAC

1951 GCTTCCAGGC TTTGCCCGAG TTGATGCCAT GCTTGGCTGG AACCATAAAA

2001 ATGTTAACGT TACCTTTGCC GCAGCCAATC TGTTCAATCA AAAATATTGG

2051 CGTTCGGACT CTATGCCGGG TAATCCGCGC GGCTATACTG CCCGGGTAAA

2101 TTACCGTTTC TGA

*Fig. 16B*

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GTVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNLTL

351 NGDYTIGRFE NHLTVGMDYS REHRNPTLGF SSAFSASINP YDRASWPASG

401 RLQPILTQNR HKADSYGIFV QNIFSATPDL KFVLGGRYDK YTFNSENKLT

451 GSSRQYSGHS FSPNIGAVWN INPVHTLYAS YNKGFAPYGG RGGYLSIDTL

501 SSAVFNADPE YTRQYETGVK SSWLDDRLST TLSAYQIERF NIRYRPDPKN

*Fig. 16B-1*

551 NPYIYAVSGK HRSRGVELSA IGQIIPKKTL SARFVGRDAG ESR*RQRKSR

601 PSGHPFE*HQ QRYRQPVFPL YPDRKPLRRN RRNRYRQTLR LRLKK*RSDY

651 ASRLCPS*CH AWLEP*KC*R YLCRSQSVQS KILAFGLYAG *SARLYCPGK

701 LPFL

*Fig. 17A*

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG TACGAACGAT TTGAGTTCCA TCCTCGAAGG CAATGCCGGC

301 ATCGACGCTG CCTACGATAT GCGCGGCGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT TCTGAAAGGC

451 CCGTCTTCCG TGCTTTACGG CCGCACCAAC GGCGGTGGCG TCATCAACAT

501 GGTCAGCAAA TACGCCAACT TCAAACAAAG CCGCAACATC GGAGCGGTTT

Fig. 17A-1

551 ACGGCTCAAG GGCAAACCGC AGCCTGAATA TGGACATTAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGTTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA TTTCACGCTC

1051 AACGGCGACT ACACCATCGG CCGTTTTGAA AACCACTTGA CCGTAGGCAT

1101 GGATTACAGC CGCGAACACC GCAACCCGAC CTTAGGTTAC AGCCGCGCCT

*Fig. 17A-2*

1151 TTACTGCTTC CATCGATCCA TACGACCGAG CAAGCTGGCC GGCTTCGGGC

1201 AGATTGCAGC CTATCCTCAC CCAAAACCGC CACAAAGCCG ACTCCTACGG

1251 CATCTTTGTG CAAAACATCT TCTCCGCCAC GCCCGATTTG AAATTCGTCC

1301 TCGGCGGCCG TTACGACAAA TACACCTTTA ATTCCGAAAA CAAACTCACC

1351 GGCAGCAGCC GCCAGTACAG CGGCCACTCG TTCAGCCCCA ACATCGGCGC

1401 AGTGTGGAAC ATCAACCCCG TTCACACACT TTACGCCTCG TATAACAAAG

1451 GTTTCGCGCC TTATGGCGGA CGCGGCGGCT ATTTGAGCAT CGATACGTCA

1501 TCTTCTGCCG TGTTTAACGC CGACCCCGAG TACACCCGCC AATACGAAAC

1551 CGGCGTCAAA AGCAGTTGGC TGGACAATCG TTTGGACACC ACATTGTCCG

1601 CCTACCAAAT CGAACGCTTC AATATCCGCT ACCGCCCCGA CGCGGAAAAT

1651 AATCCCTACA CTTGGGCAGT CGGCGGCAAA CACCGTTCGC GTGGCGTGGA

1701 ATTGTCCGCC ATCGGGCAAA TCATCCCCAA AAAACTCTAT CTGCGCGGTT

*Fig. 17A-3*

1751 CGTTGGGCGT GATGCAGGCG AAAGTCGTTG AAGACAAAAA AAATCCCGAC

1801 CGAGTGGGCA TCCATTTGAA TAATACCAGC AACGTTACCG GCAACCTGTT

1851 TTTCCGTTAT ACCCGACCGA AAACCTCTAC GGCGAAATCG GCGTAACCGG

1901 TACAGGCAAA CGCTACGGTT ACAACTCAAG AAATAAAGAA GTGACTACGC

1951 TTCCAGGCTT TGCCCGAGTT GATGCCATGC TTGGCTGGAA CCATAAAAAT

2001 GTTAACGTTA CCTTTGCCGC AGCCAATCTG TTCAATCAAA AATATTGGCG

2051 TTCGGACTCT ATGCCGGGTA ATCCGCGCGG CTATACTGCC CGGGTAAATT

2101 ACCGTTTCTG A

Fig. 17B

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYGSRANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNFTL

351 NGDYTIGRFE NHLTVGMDYS REHRNPTLGY SRAFTASIDP YDRASWPASG

401 RLQPILTQNR HKADSYGIFV QNIFSATPDL KFVLGGRYDK YTFNSENKLT

451 GSSRQYSGHS FSPNIGAVWN INPVHTLYAS YNKGFAPYGG RGGYLSIDTS

501 SSAVFNADPE YTRQYETGVK SSWLDNRLDT TLSAYQIERF NIRYRPDAEN

Fig. 17B-1

551 NPYTWAVGGK HRSRGVELSA IGQIIPKKLY LRGSLGVMQA KVVEDKKNPD

601 RVGIHLNNTS NVTGNLFFRY TRPKTSTAKS A*PVQANATV TTQEIKK*LR

651 FQALPELMPC LAGTIKMLTL PLPQPICSIK NIGVRTLCRV IRAAILPG*I

701 TVS

Fig. 18A

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG TACGAACGAT TTGAGTTCCA TCCTCGAAGG CAATGCCGGC

301 ATCGACGCTG CCTACGATAT GCGCGGCGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT CCTGAAAGGC

451 CCGTCTTCCG TGCTTTACGG CCGCACCAAC GGCGGCGGCG TCATCAACAT

501 GGTCAGCAAA TACGCCAACT TCAAACAAAG CCGCAACATC GGAGCGGTTT

*Fig. 18A-1*

551 ACGGCTCATG GGCAAACCGC AGCCTGAATA TGGACATTAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGTTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA CTTAACGCTC

1051 AACGGCGACT ACACCATCGG CCGTTTTGAA AACCACCTGA CCGTAGGCAT

1101 GGATTACAGC CGCGAACACC GCAACCCGAC ATTGGGTTTC AGCAGCGCCT

*Fig. 18A-2*

1151 TTTCCGCCTC CATCAACCCC TACGACCGCG CAAGCTGGCC GGCTTCGGGC

1201 AGATTGCAGC CTATTCTGAC CCAAAACCGC CACAAAGCCG ACGCCTACGG

1251 CATCTTTGTG CAAAACATCT TCTCCGCCAC GCCCGATTTG AAATTCGTCC

1301 TCGGCGGTCG TTACGACAAA TACACCTTTA ATTCCGAAAA CAAACTCACC

1351 GGCAGCAGCC GCCAATACAG CGGACACTCG TTCAGCCCCA ACATCGGCGC

1401 AGTGTGGAAC ATCAATCCCG TCCACACACT TTACGCCTCG TATAATAAAG

1451 GCTTCGCGCC TTATGGCGGA CGCGGCGGCT ATTTGAGCAT CAACACGTCG

1501 TCTTCCGCCG TGTTCAACGC CGACCCCGAG TACACCCGCC AATACGAAAC

1551 CGGTGTGAAA AGCAGTTGGC TGGACGACCG CCTCAGCACT ACGTTGTCTG

1601 CCTACCAAAT CGAACGCTTC AATATCCGCT ACCGCCCCGA CGAGCAAAAT

1651 GATCCCTACA CTTGGGCAGT CGGCGGCAAA CACCGTTCGC GCGGCGTGGA

1701 ATTGTCCGCC ATCGGGCAAA TCATCCCCAA AAAACTCTAT CTGCGCGGTT

*Fig. 18A-3*

1751 CGTTGGGCGT GATGCAGGCG AAAGTCGTTG AAGACAAAGA AAATCCCGAC

1801 CGAGTGGGCA TCCATTTGAA TAACACCAGC AACGTTACCG GCAACCTGTT

1851 TTTCCGTTAT ACCCCGACCG AAAACCTCTA CGGCGAAATC GGCGTAACCG

1901 GTACAGGCAA ACGCTACGGT TACAACTCAA GAAATAAAGA AGTGACTACG

1951 CTTCCAGGCT TTGCCCGAGT TGATGCCATG CTTGGCTGGA ACCATAAAAA

2001 TGTTAACATT ACCTTTGCCG CAGCCAATCT GCTCAATCAA AAATATTGGC

2051 GTTCGGATGC CATGCCCGGC GCGCCGCGCA CTTATACGGC GCGGGTTAAT

2101 TACAGTTTCT AA

*Fig. 18B*

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNLTL

351 NGDYTIGRFE NHLTVGMDYS REHRNPTLGF SSAFSASINP YDRASWPASG

401 RLQPILTQNR HKADAYGIFV QNIFSATPDL KFVLGGRYDK YTFNSENKLT

451 GSSRQYSGHS FSPNIGAVWN INPVHTLYAS YNKGFAPYGG RGGYLSINTS

501 SSAVFNADPE YTRQYETGVK SSWLDDRLST TLSAYQIERF NIRYRPDEQN

*Fig. 18B-1*

551 DPYTWAVGGK HRSRGVELSA IGQIIPKKLY LRGSLGVMQA KVVEDKENPD

601 RVGIHLNNTS NVTGNLFFRY TPTENLYGEI GVTGTGKRYG YNSRNKEVTT

651 LPGFARVDAM LGWNHKNVNI TFAAANLLNQ KYWRSDAMPG APRTYTARVN

701 YSF*

*Fig. 19A*

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC TAGAAAAACA

251 AAAATTACGG TACGAACGAT TTGAGTTCCA TCCTCGAAGG CAATGCCGGC

301 ATCGACGCTG CCTACGATAT GCGCGGCGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT CCTGAAAGGC

451 CCGTCTTCCG TGCTTTACGG CCGCACCAAC GGCGGCGGCG TCATCAACAT

501 GGTCAGCAAA TACGCCAACT TCAAACAAAG CCGCAACATC GGTGCGGTTT

Fig. 19A-1

551 ACGGTTCGTG GGCAAACCGC AGCCTGAATA TGGACATTAA CGAAGTGTTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGCTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA TTTCACGCTA

1051 AACGGCGACT ACACCATCGG CCGTTTTGAA AACCACTTGA CCGTAGGCAT

1101 GGATTACAGC CGCGAACACC GCAACCCGAC CTTAGGTTAC AGCCGCGCCT

*Fig. 19A-2*

1151 TTACTGCTTC CATCGATCCA TACGACCGAG CAAGCTGGCC GGCTTCGGGC

1201 AGATTGCAGC CTATCCTCAC CCAAAACCGC CACAAAGCCG ACTCCTACGG

1251 CATCTTTGTG CAAAACATCT TCTCCGCCAC GCCCGATTTG AAATTCGTCC

1301 TCGGCGGTCG TTACGACAAA TACACCTTTA ATTCCGAAAA CAAACTCACC

1351 GGCAGCAGCC GCCAATACAG CGGACACTCG TTCAGCCCCA ACATCGGCGC

1401 AGTGTGGAAC ATCAATCCCG TCCACACACT TTACGCCTCG TATAATAAAG

1451 GCTTCGCGCC TTATGGCGGA CGCGGCGGCT ATTTGAGCAT CAACACGTCG

1501 TCTTCCGCCG TGTTCAACGC CGACCCCGAG TACACCCGCC AATACGAAAC

1551 CGGTGTGAAA AGCAGTTGGC TGGACGACCG CCTCAGCACT ACGTTGTCTG

1601 CCTACCAAAT CGAACGCTTC AATATCCGCT ACCGCCCCGA CGAGCAAAAT

1651 GATCCCTACA CTTGGGCAGT CGGCGGCAAA CACCGTTCGC GCGGCGTGGA

1701 ATTGTCCGCC ATCGGGCAAA TCATCCCCAA AAAACTCTAT CTGCGCGGTT

Fig. 19A-3

1751 CGTTGGGCGT GATGCAGGCG AAAGTCGTTG AAGACAAAGA AAATCCCGAC

1801 CGAGTGGGCA TCCATTTGAA TAACACCAGC AACGTTACCG GCAACCTGTT

1851 TTTCCGTTAT ACCCCGACCG AAAACCTCTA CGGCGAAATC GGCGTAACCG

1901 GTACAGGCAA ACGCTACGGT TACAACTCAA GAAATAAAGA AGTGACTACG

1951 CTTCCAGGCT TTGCCCGAGT TGATGCCATG CTTGGCTGGA ACCATAAAAA

2001 TGTTAACATT ACCTTTGCCG CAGCCAATCT GCTCAATCAA AAATATTGGC

2051 GTTCGGATGC CATGCCCGGC GCGCCGCGCA CTTATACGGC GCGGGTTAAT

2101 TACAGTTTCT AA

*Fig. 19B*

1 MKISFHLALL PTLIIASFPV AAADTQDNGE HYTATLPTVS VVGQSDTSVL

51 KGYINYDEAA VTRNGQLIKE TPQTIDTLNI *KNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNFTL

351 NGDYTIGRFE NHLTVGMDYS REHRNPTLGY SRAFTASIDP YDRASWPASG

401 RLQPILTQNR HKADSYGIFV QNIFSATPDL KFVLGGRYDK YTFNSENKLT

451 GSSRQYSGHS FSPNIGAVWN INPVHTLYAS YNKGFAPYGG RGGYLSINTS

501 SSAVFNADPE YTRQYETGVK SSWLDDRLST TLSAYQIERF NIRYRPDEQN

Fig. 19B-1

551 DPYTWAVGGK HRSRGVELSA IGQIIPKKLY LRGSLGVMQA KVVEDKENPD

601 RVGIHLNNTS NVTGNLFFRY TPTENLYGEI GVTGTGKRYG YNSRNKEVTT

651 LPGFARVDAM LGWNHKNVNI TFAAANLLNQ KYWRSDAMPG APRTYTARVN

701 YSF*

*Fig. 20A*

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC TAGAAAAACA

251 AAAATTACGG TACGAACGAT TTGAGTTCCA TCCTCGAAGG CAATGCCGGC

301 ATCGACGCTG CCTACGATAT GCGCGGCGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT CCTGAAAGGC

451 CCGTCTTCCG TGCTTTACGG CCGCACCAAC GGCGGCGGCG TCATCAACAT

501 GGTCAGCAAA TACGCCAACT TCAAACAAAG CCGCAACATC GGTGCGGTTT

*Fig. 20A-1*

551 ACGGTTCGTG GGCAAACCGC AGCCTGAATA TGGACATTAA CGAAGTGTTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGCTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA TTTCACGCTA

1051 AACGGCGACT ACACCATCGG CCGTTTTGAA AACCACTTGA CCGTAGGCAT

1101 GGATTACAGC CGCGAACACC GCAACCCGAC ATTGGGCTAC CGCGGCAGTT

*Fig. 20A-2*

1151 TCACCGTGCC CATCAACCCC TACGACCGCG CAAGCTGGCC GGCTTCGGGC

1201 AGATTGCAGC CTATTCTGAC CCAAAACCGC CACAAAGCCG ACTCCTACGG

1251 CATCTTTGTG CAAAACATCT TCTCCGCTAC GCCCGATTTG AAATTCGTCC

1301 TCGGCGGCCG TTACGACAAA TACACCTTTA ATTCCGAAAA CAAACTCACC

1351 GGCAACAGCC GCCAATACAG CGGACACTCG TTCAGCCCCA ACATCGGCGC

1401 AGTGTGGAAC ATCAACCCAG TCCACACACT TTACGCCTCG TATAACAAAG

1451 GCTTCGCGCC TTATGGCGGA CGCGGCGGCT ATTTGAGTAT CGATACGTTG

1501 TCTTCCGCCG TGTTCAACGC CGACCCCGAG TACACCCGCC AATACGAAAC

1551 CGGCGTGAAA AGCAGTTGGC TGGACGACCG CCTCAGCACC ACATTGTCCG

1601 CCTACCAAAT CGAACGCTTC AATATCCGCT ACCGCCCCGA TCCAAAAAAC

1651 AACCCTTATA TTTATGCGGT TAGCGGCAAA CACCGTTCGC GCGGCGTGGA

1701 ATTGTCCGCC ATCGGGCAAA TCATCCCCAA AAAACTCTAT CTGCGCGGTT

*Fig. 20A-3*

1751 CGTTGGGCGT GATGCAGGCG AAAGTCGTTG AAGACAAAGA AAATCCCGAC

1801 CGAGTGGGCA TCCATTTGAA TAATACCAGC AACGTTACCG GCAACCTGTT

1851 TTTCCGTTAT ACCCCGACCG AAAACCTCTA CGGCGAAATC GGCGTAACCG

1901 GTACAGGCAA ACGCTACGGT TACAACTCAA GAAATAAAGA AGTGACTACG

1951 CTTCCAGGCT TTGCCCGAGT TGATGCCATG CTTGGCTGGA ACCATAAAAA

2001 TGTTAACGTT ACCTTTGCCG CAGCCAATCT GTTCAATCAA AAATATTGGC

2051 GTTCGGACTC TATGCCGGGT AATCCGCGCG GCTATACTGC CCGGGTAAAT

2101 TACCGTTTCT GA

*Fig. 20B*

1 MKISFHLALL PTLIIASFPV AAADTQDNGE HYTATLPTVS VVGQSDTSVL

51 KGYINYDEAA VTRNGQLIKE TPQTIDTLNI *KNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNFTL

351 NGDYTIGRFE NHLTVGMDYS REHRNPTLGY RGSFTVPINP YDRASWPASG

401 RLQPILTQNR HKADSYGIFV QNIFSATPDL KFVLGGRYDK YTFNSENKLT

451 GNSRQYSGHS FSPNIGAVWN INPVHTLYAS YNKGFAPYGG RGGYLSIDTL

501 SSAVFNADPE YTRQYETGVK SSWLDDRLST TLSAYQIERF NIRYRPDPKN

*Fig. 20B-1*

551 NPYIYAVSGK HRSRGVELSA IGQIIPKKLY LRGSLGVMQA KVVEDKENPD

601 RVGIHLNNTS NVTGNLFFRY TPTENLYGEI GVTGTGKRYG YNSRNKEVTT

651 LPGFARVDAM LGWNHKNVNV TFAAANLFNQ KYWRSDSMPG NPRGYTARVN

701 YRF*

Fig. 21A

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG TACGAACGAT TTGAGTTCCA TCCTCGAAGG CAATGCCGGC

301 ATCGACGCTG CCTACGATAT GCGCGGCGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT CCTGAAAGGC

451 CCGTCTTCCG TGCTTTACGG CCGCACCAAC GGCGGCGGCG TCATCAACAT

501 GGTCAGCAAA TACGCCAACT TCAAACAAAG CCGCAACATC GGTGCGGTTT

*Fig. 21A-1*

551 ACGGTTAGTG GGCAAACCGC AGCCTGAATA TGGACATTAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGTTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACTGAC AACAAAACCC TGTCGTCCAA TTTCACGCTA

1051 AACGGCGACT ACACCATCGG CCGTTTTGAA AACCACTTGA CCGTAGGCAT

1101 GGATTACAGC CGCGAACACC GCAACCCGAC CTTAGGTTAC AACCGCGCCT

*Fig. 21A-2*

1151 TTTCCGCCTC CATCAACCCC TACGACCGCG CAAGCTGGCC GGCTTCGGGC

1201 AGATTGCAGC CTATTCTGAC CCAAAACCGC CACAAAGCCG ACTCCTACGG

1251 CATCTTTGTG CAAAACATCT TCTCCGCCAC GCCCGATTTG AAATTCGTCC

1301 TCGGCGGCCG TTACGACAAA TACACCTTTA ATTCCGAAAA CAAACTCACC

1351 GGCAGCAGCC GCCAATACAG CGGACACTCG TTCAGCCCCA ACATCGGCGC

1401 AGTGTGGAAC ATCAATCCCG TCCACACACT TTACGCCTCG TATAACAAAG

1451 GCTTCGCGCC TTATGGCGGA CGCGGCGGCT ATTTGAGCAT CGATACGTTG

1501 TCTTCCGCCG TGTTCAACGC CGACCCCGAG TACACCCGCC AATACGAAAC

1551 CGGCGTGAAA AGCAGTTGGC TGGACGACCG CCTCAGCACT ACGTTGTCTG

1601 CCTACCAAAT CGAACGCTTC AATATCCGCT ACCGCCCCGA TCCAAAAAAC

1651 AACCCTTATA TTTATGCGGT TAGCGGCAAA CACCGTTCGC GCGGCGTGGA

1701 ATTGTCCGCC ATCGGGCAAA TCATCCCTAA AAAACTCTAT CTGCGCGGTT

*Fig. 21A-3*

1751 CGTTGGGCGT GATGCAGGCG AAAGTCGTTG AAGACAAAGA AAATCCCGAC

1801 CGAGTGGGCA TCCATTTGAA TAACACCAGC AACGTTACCG GCAACCTGTT

1851 TTTCCGTTAT ACCCCGACCG AAAACCTCTA CGGCGAAATC GGCGTAACCG

1901 GTACAGGCAA ACGCTACGGT TACGACTCAA GAAATAAAGA AGTGACTACG

1951 CTTCCAGGCT TTGCCCGAGT TGATGCCATG CTTGGCTGGA ACCATAAAAA

2001 TGTTAACGTT ACCTTTGCCG CAGCCAATCT GTTCAATCAA AAATATTGGC

2051 GTTCGGACTC TATGCCGGGT AATCCGCGCG GCTATACTGC CCGGGTAAAT

2101 TACCGTTTCT GA

*Fig. 21B*

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYG*WANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNFTL

351 NGDYTIGRFE NHLTVGMDYS REHRNPTLGY NRAFSASINP YDRASWPASG

401 RLQPILTQNR HKADSYGIFV QNIFSATPDL KFVLGGRYDK YTFNSENKLT

451 GSSRQYSGHS FSPNIGAVWN INPVHTLYAS YNKGFAPYGG RGGYLSIDTL

501 SSAVFNADPE YTRQYETGVK SSWLDDRLST TLSAYQIERF NIRYRPDPKN

*Fig. 21B-1*

551 NPYIYAVSGK HRSRGVELSA IGQIIPKKLY LRGSLGVMQA KVVEDKENPD

601 RVGIHLNNTS NVTGNLFFRY TPTENLYGEI GVTGTGKRYG YDSRNKEVTT

651 LPGFARVDAM LGWNHKNVNV TFAAANLFNQ KYWRSDSMPG NPRGYTARVN

701 YRF*

*Fig. 22A*

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG TACGAACGAT TTGAGTTCCA TCCTCGAAGG CAATGCCGGC

301 ATCGACGCTG CCTACGATAT GCGCGGTGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT CCTGAAAGGC

451 CCGTCTTCCG TGCTTTACGG CCGCACCAAC GGCGGCGGCG TCATCAACAT

501 GGTCAGCAAA TACGCCAACT TCAAACAAAG CCGCAACATC GGTGCGGTTT

*Fig. 22A-1*

551 ACGGTTCGTG GGCAAACCGC AGCCTGAATA TGGACATTAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGTTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA CTTAACGCTC

1051 AACGGCGACT ACACCATCGG CCGTTTTGAA AACCACCTGA CCGTAGGCAT

1101 GGATTACAGT CGCGAACACC GCAACCCGAC ATTGGGCTAC CGCGGCAGTT

*Fig. 22A-2*

1151 TCACCGTGCC CATCAACCCC TACGACCGCG CAAGCTGGCC GGCTTCGGGC

1201 AGATTGCAGC CTATTCTGAC CCAAAACCGC CACAAAGCCG ACTCCTACGG

1251 CATCTTTGTG CAAAACATCT TCTCCGCTAC GCCCGATTTG AAATTCGTCC

1301 TCGGCGGCCG TTACGACAAA TACACCTTTA ATTCCGAAAA CAAACTCACC

1351 GGCAACAGCC GCCAATACAG CGGACACTCG TTCAGCCCCA ACATCGGCGC

1401 AGTGTGGAAC ATCAACCCAG TCCACACACT TTATGCCTCG TATAACAAAG

1451 GCTTCGCGCC TTATGGCGGA CGCGGCTATT TGAGTATCGA CACTTCGTCT

1501 GCCGCCGTGT TCAACGCCGC CCCCGAGTAC ACTCGCCAAT ACGAAACCGG

1551 TGTGAAAAGC AGTTGGCTGG ACGACCGCCT CAGCACCACA TTGTCCGCCT

1601 ACCAAATCGA ACGCTTCAAT ATCCGCTACC GCCCCGATCC AAAAAACAAC

1651 CCTTATATTT ATGCGGTTAG CGGCAAACAC CGTTCGCGCG GCGTGGAATT

1701 GTCCGCCATC GGGCAAATCA TCCCTAAAAA ACTCTATCTG CGCGGTTCGT

*Fig. 22A-3*

1751 TGGGCGTGAT GCAGGCGAAA GTCGTTGAAG ACAAAGAAAA TCCCGACCGA

1801 GTGGGCATCC ATTTGAATAA CACCAGCAAC GTTACCGGCA ACCTGTTTTT

1851 CCGTTATACC CCGACTGAAA ACCTCTACGG CGAAATCGGC GTAACCGGTA

1901 CAGGCAAACG CTACGGCTAC AACTCAAGAA ATAAAGAAGT GACCACGCTT

1951 CCAGGCTTTG CCCGAGTTGA TGCCATGCTC GGCTGGAACC ATAAAAATGT

2001 TAACGTTACC TTTGCCGCTG CCAATCTGCT CAATCAAAAA TATTGGCGTT

2051 CGGACTCTAT GCCGGGTAAT CCGCGCGGCT ATACTGCCCG GGTAAATTAC

2101 CGTTTCTGA

*Fig. 22B*

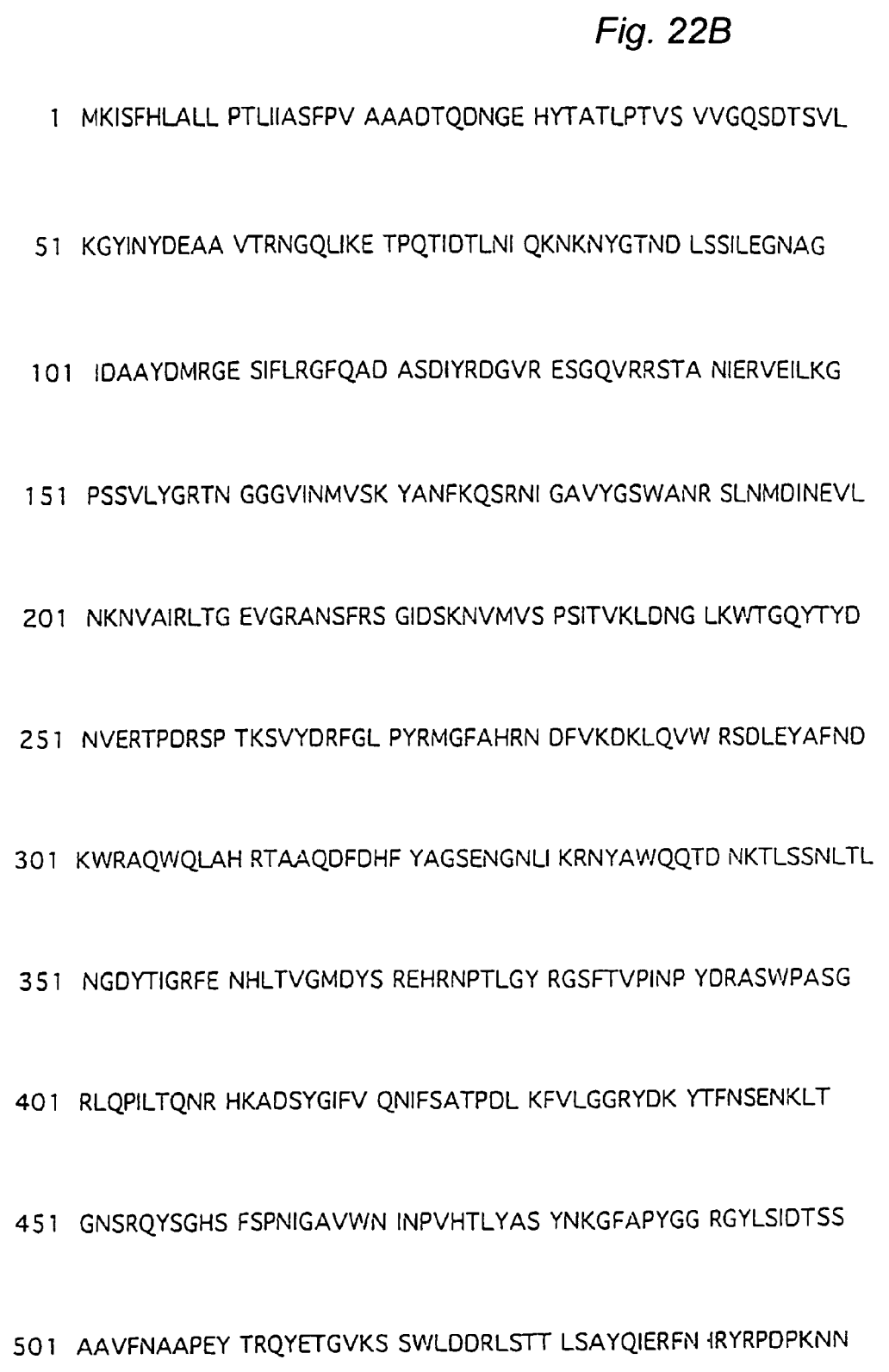

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNLTL

351 NGDYTIGRFE NHLTVGMDYS REHRNPTLGY RGSFTVPINP YDRASWPASG

401 RLQPILTQNR HKADSYGIFV QNIFSATPDL KFVLGGRYDK YTFNSENKLT

451 GNSRQYSGHS FSPNIGAVWN INPVHTLYAS YNKGFAPYGG RGYLSIDTSS

501 AAVFNAAPEY TRQYETGVKS SWLDDRLSTT LSAYQIERFN HRYRPDPKNN

*Fig. 22B-1*

551 PYIYAVSGKH RSRGVELSAI GQIIPKKLYL RGSLGVMQAK VVEDKENPDR

601 VGIHLNNTSN VTGNLFFRYT PTENLYGEIG VTGTGKRYGY NSRNKEVTTL

651 PGFARVDAML GWNHKNVNVT FAAANLLNQK YWRSDSMPGN PRGYTARVNY

701 RF*

Fig. 23A

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACGCTACC TACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG CACGAACGAT TTGAGTTCCA TCCTCGAAGG CAATGCCGGC

301 ATCGACGCTG CCTACGATAT GCGCGGTGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT CCTGAAAGGC

451 CCGTCTTCCG TGCTTTACGG CCGTACCAAC GGCGGCGGCG TCATCAACAT

501 GGTCAGCAAA TACGCCAACT TCAAACAAAG CCGCAACATC GGTGCGGTTT

*Fig. 23A-1*

551 ACGGTTCGTG GGCAAACCGC AGCCTGAATA TGGACATTAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCCGAAC GATTTTGTCA

851 AAGACAAGCT GCAAGTTTGG CGTTCCGACC TCGAATACGC CTTCAACGAC

901 AAATGGCGCG CCCAATGGCA GCTCGCCCAC CGCACGGCAG CGCAGGATTT

951 CGACCATTTT TATGCAGGCA GCGAAAACGG CAGCCGAATC AAACGCAACT

1001 ACGCCTGGCA GCAGACCGAC AACAAAACTC TGTCGTCCAA CTTCACGCTC

1051 AACGGCGACT ACACCATCGG TCGTTTTGAA AACCACCTGA CCGTAGGCAT

1101 GGATTACAGC CGCGAACACC GCAACCCGAC ATTGGGCTAC CGCGGCAGTT

*Fig. 23A-2*

1151 TCACCGTGCC CATCAACCCC TACGACCGCG CAAGCTGGCC GGCTTCGGGC

1201 AGATTGCAGC CTATTCTGAC CCAAAACCGC CACAAAGCCG ACTCCTACGG

1251 CATCTTTGTG CAAAACATCT TCTCCGCTAC GCCCGATTTG AAATTCGTCC

1301 TCGGCGGCCG TTACGACAAA TACACCTTTA ATTCCGAAAA CAAACTCACC

1351 GGCAACAGCC GCCAATACAG CGGACACTCG TTCAGCCCCA ACATCGGCGC

1401 AGTGTGGAAC ATCAACCCAG TCCACACACT TTACGCCTCG TATAACAAAG

1451 GCTTCGCGCC TTATGGCGGA CGCGGATATT TGAGTATCGA CACTTCGTCT

1501 GCCGCCGTGT TCAACGCCGC CCCCGAGTAC ACCCCCAATA CGAAACCGGC

1551 GTCAAAAGCA GTTGGCTGGA CAATCGTTTG GACACCACCC TGTCGGTTTA

1601 CCAAATCGAA CGCTTCAATA TCCGCTACCG CCCCGATCCA AAAAACAACC

1651 CTTATATTTA TGCGGTTAGC GGCAAACACC GTTCGCGCGG CGTGGAATTG

1701 TCCGCCATCG GGCAAATCAT CCCCAAAAAA CTCTATCTGC GCGGTTCGTT

*Fig. 23A-3*

1751 GGGCGTGATG CAGGCGAAAG TCGTTGAAGA CAAAGAAAAT CCCGACCGAG

1801 TGGGCATCCA TTTGAATAAC ACCAGCAACG TTACCGGCAA CCTGTTTTTC

1851 CGTTATACCC CGACCGAAAA CCTCTACGGC GAAATCGGCG TAACCGGTAC

1901 GGGCAAACGC TACGGTTACA ACTCAAGAAA TAAAGAAGTG ACTACGCTTC

1951 CAGGCTTTGC CCGAGTTGAT GCCATGCTTG GCTGGAACCA TAAAAATGTT

2001 AACGTTACCT TTGCCGCAGC CAATCTGTTC AATCAAAAAT ATTGGCGTTC

2051 GGACTCTATG CCGGGTAATC CGCGCGGCTA TACTGCCCGG GTAAATTACC

2101 GTTTCTGA

*Fig. 23B*

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHPN DFVKDKLQVW RSDLEYAFND

301 KWRAQWQLAH RTAAQDFDHF YAGSENGSRI KRNYAWQQTD NKTLSSNFTL

351 NGDYTIGRFE NHLTVGMDYS REHRNPTLGY RGSFTVPINP YDRASWPASG

401 RLQPILTQNR HKADSYGIFV QNIFSATPDL KFVLGGRYDK YTFNSENKLT

451 GNSRQYSGHS FSPNIGAVWN INPVHTLYAS YNKGFAPYGG RGYLSIDTSS

501 AAVFNAAPEY TPNTKPASKA VGWTIVWTPP CRFTKSNASI SATAPIQKTT

Fig. 23B-1

551 LIFMRLAANT VRAAWNCPPS GKSSPKNSIC AVRWA*CRRK SLKTKKIPTE

601 WASI*ITPAT LPATCFSVIP RPKTSTAKSA *PVRANATVT TQEIKK*LRF

651 QALPELMPCL AGTIKMLTLP LPQPICSIKN IGVRTLCRVI RAAILPG*IT

701 VS

*Fig. 24A*

1 ATGCAAATAC CATTTCATTT GGCTTTATTA CCCACGCTGA TTATTGCTTC

51 CTTCCCTGTT GCTGCCGCCG ATACGCAGGA CAATGGTGAA CATTACACCG

101 CCACGCTACC TACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG CACGAACGAT TTGAGTTCCA TCCTCGAAGG CAATGCCGGC

301 ATCGACGCCG CCTACGATAT GCGCGGCGAA AGCATTTTCC TGCGCGGCTT

351 TCAAGCCGAC GCATCTGATA TTTACCGCGA CGGCGTACGC GAAAGCGGGC

401 AGGTGCGCCG TAGCACCGCC AACATCGAGC GCGTGGAAAT CCTGAAAGGT

451 CCGTCCTCCG TGCTTTATGG GCGTACCAAC GGCGGCGGTG TCATCAACAT

501 GGTCAGCAAA TACGCCAACT TCAAACAAAG CCGTAATATC GGTACGGTTT

Fig. 24A-1

551 ATGGTTCGTG GGCAAACCGT AGCCTGAATA TGGACATCAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGTTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA CTTAACGCTC

1051 AACGGCGACT ACACCATCGG CCGTTTTGAA AACCACCTGA CCGTAGGCAT

1101 GGATTACAGC CGCGAACACC GCAACCCGAC ATTGGGTTTC AGCAGCGCCT

*Fig. 24A-2*

1151 TTTCCGCCTC CATCAACCCC TACGACCGCG CAAGCTGGCC GGCTTCGGGC

1201 AGATTGCAGC CTATTCTGAC CCAAAACCGC CACAAAGCCG ACTCCTACGG

1251 CATCTTTGTG CAAAACATCT TCTCCGCCAC GCCCGATTTG AAATTCGTCC

1301 TCGGCGGCCG TTACGACAAA TACACCTTTA ATTCCGAAAA CAAACTCACC

1351 GGCAGCAGCC GCCAATACAG CGGACACTCG TTCAGCCCCA ACATCGGCGC

1401 AGTGTGGAAC ATCAATCCCG TCCACACACT TTACGCCTCG TATAACAAAG

1451 GCTTCGCGCC TTATGGCGGA CGCGGCGGCT ATTTGAGCAT CGATACGTTG

1501 TCTTCCGCCG TGTTCAACGC CGACCCCGAG TACACCCGCC AATACGAAAC

1551 CGGCGTGAAA AGCAGTTGGC TGGACGACCG CCTCAGCACT ACGTTGTCTG

1601 CCTACCAAAT CGAACGCTTC AATATCCGCT ACCGCCCCGA TCCAAAAAAC

1651 AACCCTTATA TTTATGCGGT TAGCGGCAAA CACCGTTCGC GCGGCGTGGA

1701 ATTGTCCGCC ATCGGGCAAA TCATCCCCAA AAAAACTCTA TCTGCGCGGT

*Fig. 24A-3*

1751 TCGTTGGGCG TGATGCAGGC GAAAGTCGTT GAAGACAAAG AAAATCCCGA

1801 CCGAGTGGGC ATCCATTTGA ATAACACCAG CAACGTTACC GGCAACCTGT

1851 TTTTCCGTTA TACCCCGACC GAAAACCTCT ACGGCGAAAT CGGCGTAACC

1901 GGTACAGGCA AACGCTACGG TTACGACTCA AGAAATAAAG AAGTGACTAC

1951 GCTTCCAGGC TTTGCCCGAG TTGATGCCAT GCTTGGCTGG AACCATAAAA

2001 ATGTTAACGT TACCTTTGCC GCAGCCAATC TGTTCAATCA AAAATATTGG

2051 CGTTCGGACT CTATGCCGGG TAATCCGCGC GGCTATACTG CCCGGGTAAA

2101 TTACCGTTTC TGA

*Fig. 24B*

1 MQIPFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GTVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNLTL

351 NGDYTIGRFE NHLTVGMDYS REHRNPTLGF SSAFSASINP YDRASWPASG

401 RLQPILTQNR HKADSYGIFV QNIFSATPDL KFVLGGRYDK YTFNSENKLT

451 GSSRQYSGHS FSPNIGAVWN INPVHTLYAS YNKGFAPYGG RGGYLSIDTL

501 SSAVFNADPE YTRQYETGVK SSWLDDRLST TLSAYQIERF NIRYRPDPKN

*Fig. 24B-1*

551 NPYIYAVSGK HRSRGVELSA IGQIIPKKTL SARFVGRDAG ESR*RQRKSR

601 PSGHPFE*HQ QRYRQPVFPL YPDRKPLRRN RRNRYRQTLR LRLKK*RSDY

651 ASRLCPS*CH AWLEP*KC*R YLCRSQSVQS KILAFGLYAG *SARLYCPGK

701 LPFL

*Fig. 25A*

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG TACGAACGAT TTGAGTTCCA TCCTCGAAGG CAATGCCGGC

301 ATCGACGCTG CCTACGATAT GCGCGGCGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT CCTGAAAGGC

451 CCGTCTTCCG TGCTTTACGG CCGCACCAAC GGCGGCGGCG TCATCAACAT

501 GGTCAGCAAA TACGCCAACT TCAAACAAAG CCGCAACATC GGTGCGGTTT

*Fig. 25A-1*

551 ACGGTTCGTG GGCAAACCGC AGCCTGAATA TGGACATTAA CGAAGTGTTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGCTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA TTTCACGCTA

1051 AACGGCGACT ACACCATCGG CCGTTTTGAA AACCACTTGA CCGTAGGCAT

1101 GGATTACAGC CGCGAACACC GCAACCCGAC CTTAGGTTAC AGCCGCGCCT

*Fig. 25A-2*

1151 TTACTGCTTC CATCGATCCA TACGACCGAG CAAGCTGGCC GGCTTCGGGC

1201 AGATTGCAGC CTATCCTCAC CCAAAACCGC CACAAAGCCG ACTCCTACGG

1251 CATCTTTGTG CAAAACATCT TCTCCGCCAC GCCCGATTTG AAATTCGTCC

1301 TCGGCGGTCG TTACGACAAA TACACCTTTA ATTCCGAAAA CAAACTCACC

1351 GGCAGCAGCC GCCAATACAG CGGACACTCG TTCAGCCCCA ACATCGGCGC

1401 AGTGTGGAAC ATCAATCCCG TCCACACACT TTACGCCTCG TATAATAAAG

1451 GCTTCGCGCC TTATGGCGGA CGCGGCGGCT ATTTGAGCAT CAACACGTCG

1501 TCTTCCGCCG TGTTCAACGC CGACCCCGAG TACACCCGCC AATACGAAAC

1551 CGGTGTGAAA AGCAGTTGGC TGGACGACCG CCTCAGCACT ACGTTGTCTG

1601 CCTACCAAAT CGAACGCTTC AATATCCGCT ACCGCCCCGA CGAGCAAAAT

1651 GATCCCTACA CTTGGGCAGT CGGCGGCAAA CACCGTTCGC GCGGCGTGGA

1701 ATTGTCCGCC ATCGGGCAAA TCATCCCCAA AAAACTCTAT CTGCGCGGTT

*Fig. 25A-3*

1751 CGTTGGGCGT GATGCAGGCG AAAGTCGTTG AAGACAAAGA AAATCCCGAC

1801 CGAGTGGGCA TCCATTTGAA TAACACCAGC AACGTTACCG GCAACCTGTT

1851 TTTCCGTTAT ACCCCGACCG AAAACCTCTA CGGCGAAATC GGCGTAACCG

1901 GTACAGGCAA ACGCTACGGT TACAACTCAA GAAATAAAGA AGTGACTACG

1951 CTTCCAGGCT TTGCCCGAGT TGATGCCATG CTTGGCTGGA ACCATAAAAA

2001 TGTTAACATT ACCTTTGCCG CAGCCAATCT GCTCAATCAA AAATATTGGC

2051 GTTCGGATGC CATGCCCGGC GCGCCGCGCA CTTATACGGC GCGGGTTAAT

2101 TACAGTTTCT AA

*Fig. 25B*

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNFTL

351 NGDYTIGRFE NHLTVGMDYS REHRNPTLGY SRAFTASIDP YDRASWPASG

401 RLQPILTQNR HKADSYGIFV QNIFSATPDL KFVLGGRYDK YTFNSENKLT

451 GSSRQYSGHS FSPNIGAVWN INPVHTLYAS YNKGFAPYGG RGGYLSINTS

501 SSAVFNADPE YTRQYETGVK SSWLDDRLST TLSAYQIERF NIRYRPDEQN

*Fig. 25B-1*

551 DPYTWAVGGK HRSRGVELSA IGQIIPKKLY LRGSLGVMQA KVVEDKENPD

601 RVGIHLNNTS NVTGNLFFRY TPTENLYGEI GVTGTGKRYG YNSRNKEVTT

651 LPGFARVDAM LGWNHKNVNI TFAAANLLNQ KYWRSDAMPG APRTYTARVN

701 YSF*

Fig. 26A

1 ATGAAAATAT CATTTCATTT AGCTTTATTA CCCACGCTGA TTATTGCTTC

51 CTTCCCTGTT GCTGCCGCCG ATACGCAGGA CAATGGTGAA CATTACACCG

101 CCACTCTGCC CACCGTTTCC GTGGTCGGAC AGTCCGACAC CAGCGTACTC

151 AAAGGCTACA TCAACTACGA CGAAGCCGCC GTTACCCGCA ACGGACAGCT

201 CATCAAAGAA ACGCCGCAAA CCATCGATAC GCTCAATATC CAGAAAAACA

251 AAAATTACGG TACGAACGAT TTGAGTTCCA TCCTCGAAGG CAATGCCGGC

301 ATCGACGCTG CCTACGATAT GCGCGGTGAA AGCATTTTCC TGCGCGGTTT

351 TCAAGCCGAC GCATCCGATA TTTACCGCGA CGGCGTGCGC GAAAGCGGAC

401 AAGTGCGCCG CAGTACTGCC AACATCGAGC GCGTGGAAAT CCTGAAAGGC

451 CCGTCTTCCG TGCTTTACGG CCGCACCAAC GGCGGCGGCG TCATCAACAT

501 GGTCAGCAAA TACGCCAACT TCAAACAAAG CCGCAACATC GGAGCGGTTT

*Fig. 26A-1*

551 ACGGCTCATG GGCAAACCGC AGCCTGAATA TGGACATTAA CGAAGTGCTG

601 AACAAAAACG TCGCCATCCG TCTCACCGGC GAAGTCGGGC GCGCCAATTC

651 GTTCCGCAGC GGCATAGACA GCAAAAATGT CATGGTTTCG CCCAGCATTA

701 CCGTCAAACT CGACAACGGC TTGAAGTGGA CGGGGCAATA CACCTACGAC

751 AATGTGGAGC GCACGCCCGA CCGCAGTCCG ACCAAGTCCG TGTACGACCG

801 CTTCGGACTG CCTTACCGCA TGGGGTTCGC CCACCGGAAC GATTTTGTCA

851 AAGACAAGCT GCAAGTTTGG CGTTCCGACC TTGAATACGC CTTCAACGAC

901 AAATGGCGTG CCCAATGGCA GCTCGCCCAC CGCACGGCGG CGCAGGATTT

951 TGATCATTTC TATGCAGGCA GCGAAAATGG CAACTTAATC AAACGTAACT

1001 ACGCCTGGCA GCAGACCGAC AACAAAACCC TGTCGTCCAA CTTAACGCTC

1051 AACGGCGACT ACACCATCGG CCGTTTTGAA AACCACCTGA CCGTAGGCAT

1101 GGATTACAGC CGCGAACACC GCAACCCGAC ATTGGGTTTC AGCAGCGCCT

*Fig. 26A-2*

1151 TTTCCGCCTC CATCAACCCC TACGACCGCG CAAGCTGGCC GGCTTCGGGC

1201 AGATTGCAGC CTATTCTGAC CCAAAACCGC CACAAAGCCG ACTCCTACGG

1251 CATCTTTGTG CAAAACATCT TCTCCGCCAC GCCCGATTTG AAATTCGTCC

1301 TCGGCGGCCG TTACGACAAA TACACCTTTA ATTCCGAAAA CAAACTCACC

1351 GGCAGCAGCC GCCAATACAG CGGACACTCG TTCAGCCCCA ACATCGGCGC

1401 AGTGTGGAAC ATCAATCCCG TCCACACACT TTACGCCTCG TATAACAAAG

1451 GCTTCGCGCC TTATGGCGGA CGCGGCGGCT ATTTGAGCAT CGATACGTTG

1501 TCTTCCGCCG TGTTCAACGC CGACCCCGAG TACACCCGCC AATACGAAAC

1551 CGGCGTGAAA AGCAGTTGGC TGGACGACCG CCTCAGCACT ACGTTGTCTG

1601 CCTACCAAAT CGAACGCTTC AATATCCGCT ACCGCCCCGA TCCAAAAAAC

1651 AACCCTTATA TTTATGCGGT TAGCGGCAAA CACCGTTCGC GCGGCGTGGA

1701 ATTGTCCGCC ATCGGGCAAA TCATCCCCAA AAAACTCTAT CTGCGCGGTT

*Fig. 26A-3*

1751 CGTTGGGCGT GATGCAGGCG AAAGTCGTTG AAGACAAAGA AAATCCCGAC

1801 CGAGTGGGCA TCCATTTGAA TAATACCAGC AACGTTACCG GCAACCTGTT

1851 TTTCCGTTAT ACCCCGACCG AAAACCTCTA CGGCGAAATC GGCGTAACCG

1901 GTACAGGCAA ACGCTACGGT TACAACTCAA GAAATAAAGA AGTGACTACG

1951 CTTCCAGGCT TTGCCCGAGT TGATGCCATG CTTGGCTGGA ACCATAAAAA

2001 TGTTAACGTT ACCTTTGCCG CAGCCAATCT GCTCAATCAA AAATATTGGC

2051 GTTCGGACTC TATGCCGGGT AATCCGCGCG GCTATACTGC CCGGGTAAAT

2101 TACCGTTTCT GA

Fig. 26B

1 MKISFHLALL PTLIIASFPV AAADTQDNGE HYTATLPTVS VVGQSDTSVL

51 KGYINYDEAA VTRNGQLIKE TPQTIDTLNI QKNKNYGTND LSSILEGNAG

101 IDAAYDMRGE SIFLRGFQAD ASDIYRDGVR ESGQVRRSTA NIERVEILKG

151 PSSVLYGRTN GGGVINMVSK YANFKQSRNI GAVYGSWANR SLNMDINEVL

201 NKNVAIRLTG EVGRANSFRS GIDSKNVMVS PSITVKLDNG LKWTGQYTYD

251 NVERTPDRSP TKSVYDRFGL PYRMGFAHRN DFVKDKLQVW RSDLEYAFND

301 KWRAQWQLAH RTAAQDFDHF YAGSENGNLI KRNYAWQQTD NKTLSSNLTL

351 NGDYTIGRFE NHLTVGMDYS REHRNPTLGF SSAFSASINP YDRASWPASG

401 RLQPILTQNR HKADSYGIFV QNIFSATPDL KFVLGGRYDK YTFNSENKLT

451 GSSRQYSGHS FSPNIGAVWN INPVHTLYAS YNKGFAPYGG RGGYLSIDTL

501 SSAVFNADPE YTRQYETGVK SSWLDDRLST TLSAYQIERF NIRYRPDPKN

*Fig. 26B-1*

551 NPYIYAVSGK HRSRGVELSA IGQIIPKKLY LRGSLGVMQA KVVEDKENPD

601 RVGIHLNNTS NVTGNLFFRY TPTENLYGEI GVTGTGKRYG YNSRNKEVTT

651 LPGFARVDAM LGWNHKNVNV TFAAANLLNQ KYWRSDSMPG NPRGYTARVN

701 YRF*

*Fig. 27A*

1 MKRFTYTLSD GLCIEIELKR SAKKNLILRP VNMQTVSINV PPFFQDHALA

51 NWLAANETIL RNTLAKMPVH PVSHPNLPEW IWYRGIKTKL DTHSQSHIRI

101 TSSEILLPRK ETAAQIDHLR RLLNERAREY LLPRLEKHAA ETGLTPAATD

151 LSNAKTFWGV CRPHTGIRLN WRLIGTPEYV ADYVCIHELC HLRHPDHSPR

201 FWHLVNTLTP HTDNAKSWLK AHGRELFVLG *

*Fig. 27B*

1 ATGAAACGCT TCACCTATAC TCTTTCCGAC GGCTTGTGCA TCGAAATCGA

51 ACTCAAACGC AGTGCCAAGA AAAATCTGAT TCTGCGCCCC GTCAATATGC

101 AGACGGTCAG CATCAACGTC CCACCCTTTT TTCAAGACCA CGCGTTAGCA

151 AACTGGCTGG CGGCAAACGA AACGATTTTG CGGAACACGC TTGCTAAAAT

201 GCCCGTGCAT CCTGTTTCCC ACCCAAACTT ACCCGAGTGG ATTTGGTATC

251 GGGGAATAAA GACCAAGCTG GATACCCACA GCCAAAGCCA TATCCGTATC

301 ACGTCGTCTG AAATCCTGCT TCCCCGAAAA GAAACCGCCG CACAAATCGA

351 CCACCTGCGC CGCCTGTTGA ACGAACGCGC CCGCGAATAC CTGCTGCCCC

401 GCCTTGAAAA ACACGCAGCC GAAACAGGAC TGACTCCCGC TGCCACAGAC

451 CTGAGCAACG CCAAAACCTT TTGGGGCGTA TGCCGCCCGC ACACCGGCAT

501 CCGCCTCAAC TGGCGGCTGA TCGGCACGCC CGAATACGTC GCCGACTATG

Fig. 27B-1

551 TCTGCATCCA CGAACTCTGC CACCTCCGCC ACCCCGACCA CAGTCCGCGC

601 TTTTGGCATT TGGTGAACAC GCTGACGCCG CATACCGACA ATGCTAAAAG

651 TTGGCTGAAG GCGCACGGGC GGGAATTGTT TGTGCTGGGG TAA

*Fig. 28A*

1 ATGAGCAAGA TTATTGTGCT GACCGCAGGC CACAGCAACA CCGACCCGGG

51 TGCGGTCAAC GGAAGCGACC GTGAGGCGGA CTTGGCGCAG GATATGCGCA

101 ACATTGTGGC TTCAATCCTG CGTAACGATT ACGGCCTGAC CGTTAAAACC

151 GACGGCACGG GCAAAGGCAA TATGCCGCTG CGCGAAGCGG TCAAGCTGAT

201 TCGCGGCTCG GATGTGGCGA TTGAGTTTCA CACCAACGCT GCCGTCAGCA

251 AAGCGGCGAC AGGCATCGAA GCCTTGAGTA CCGTTAAAAA CAAACGCTGG

301 TGTCAGGTGT TGAGCAAAGC CGTTGCCAAG AAAACCGGCT GGAAACTGCG

351 CGGCGAAGAC GGCTTTAAAC CCGACAATGC GGGCCAGCAT TCGCGCCTGG

401 CTTATGCACA AGCCGGCGGC ATTGTGTTTG AGCCTTTTTT CATCAGCAAC

451 GACACTGATT TGGCCTTGTT TAAGACGACT AAATGGGGCA TCTGCCGCGC

501 GATTGCGGAC GCGATTGCGA TGGAATTGGG GGCGGCAAGA GTATGA

*Fig. 28B*

1 MSKIIVLTAG HSNTDPGAVN GSDREADLAQ DMRNIVASIL RNDYGLTVKT

51 DGTGKGNMPL REAVKLIRGS DVAIEFHTNA AVSKAATGIE ALSTVKNKRW

101 CQVLSKAVAK KTGWKLRGED GFKPDNAGQH SRLAYAQAGG IVFEPFFISN

151 DTDLALFKTT KWGICRAIAD AIAMELGAAR V*

*Fig. 29A*

1 ATGCGTATTT TGGATATTTT TAAAAACCCA GCGACAGGCA ATGTGTCGCA

51 CTCGAAACTG TGGGCAAACG TTGCCTGCGC GGCGGGGACG GTTAAGTTTG

101 TGATGCTGCC CGACCCGTCG GCGGAGATTT GGGCGGTGTA TTTGGGCATT

151 GTCGGCGGCT ATGCGGTGGC GCGTTCGTTG GTCAGCGTCA AACGTCAGGA

201 GGTCGAGAAT GAATCTCGTG AAACTGCTGG CGAATAA

*Fig. 29B*

1 MRILDIFKNP ATGNVSHSKL WANVACAAGT VKFVMLPDPS AEIWAVYLGI

51 VGGYAVARSL VSVKRQEVEN ESRETAGE*

*Fig. 30A*

1 ATGCGGTGGC GCGTTCGTTG GTCAGCGTCA AACGTCAGGA GGTCGAGAAT

51 GAATCTCGTG AAACTGCTGG CGAATAACTG GCAACCGATT GCCATCATCG

101 CGCTTGTCGG CACGGGTTTG GCGGTGTCGC ACCATCAAGG CTACAAGTCG

151 GCTTTTGCGA AGCAGCAGGC GGTCATTGAG AAAATGAAGC GCGACAAGGC

201 GCAAGCCCTG CTGTTGTCGG CTCAAAACTA CGCCCGCGAA CTGGAACAGG

251 CGCGTGCGGA AGCTAAAAAA TATGAAGTCA AGGCGCACGC CGTCGGCATG

301 GCTTTGGCGA AAAAACAGGC GGAAGTCAGC CGTCTGAAAA CGGAAAATAA

351 AAAGGAAATC GAAAATGTCC TTACTCAAGA CCGTAAAAAT GCAGGCGGCG

401 GTTGTATTGA CGGCTTTGGC CATCACGGCT TGCAGCTCTA CAAGCGCGCC

451 CTCGGCTACG GAAATTAA

*Fig. 30B*

1 MRWRVRWSAS NVRRSRMNLV KLLANNWQPI AIIALVGTGL AVSHHQGYKS

51 AFAKQQAVIE KMKRDKAQAL LLSAQNYARE LEQARAEAKK YEVKAHAVGM

101 ALAKKQAEVS RLKTENKKEI ENVLTQDRKN AGGGCIDGFG HHGLQLYKRA

151 LGYGN*

*Fig. 31A*

1 ATGTCCTTAC TCAAGACCGT AAAAATGCAG GCGGCGGTTG TATTGACGGC

51 TTTGGCCATC ACGGCTTGCA GCTCTACAAG CGCGCCCTCG GCTACGGAAA

101 TTAAGGTTGT CGAAAAGGCG GTCATGCCGA CACCGCCTGC CGCGTTGATG

151 GTCGCGCCGG TGCGCCCGAA TCCGCCGAAA GACGGCAAGA CGGCCACGCT

201 GTTGGAACAC GCCGCCGAGT TTGGCGGCTA TGTTGCCGAA CTTGAAAACC

251 AAAATCAGGC TTGGCGCGAC TGGGCGGGCA ATCACTCCCG CAAAGTCGGA

301 AACTGA

*Fig. 31B*

1 MSLLKTVKMQ AAVVLTALAI TACSSTSAPS ATEIKVVEKA VMPTPPAALM

51 VAPVRPNPPK DGKTATLLEH AAEFGGYVAE LENQNQAWRD WAGNHSRKVG

101 N*

*Fig. 32A*

1 GTGCTGGCAG TTTTGCTTGC TGGTGTAGCC TTCGCCCTGA GCGATGATTT

51 CATGGTTGGC TGCTTTCAAA CGCCAACGGT ATTCGCCTTT TGCGTCTTTA

101 TAGATTTCAA AATACATAAG GTTTCTCCTA TGAATGAGTA CACGTTTTCT

151 TACCGCTTTA ACGGCAAGTC CTGGTCATTG AGCATTTGGG CGGACAACCC

201 TGAAGAAGCC AGGGCGAAAT TTCGGGCTGC ACGAGAAAAT GCGCACTATG

251 ACGGCGAAGT TGTAGCAAAG GTTTATACAT TTGTAAATAT TTCGTGGGTT

301 AAGAAATTGT ACAAGCGGAC AAAATATTTA ATGGGTATCA AAGAATGA

*Fig. 32B*

1 VLAVLLAGVA FALSDDFMVG CFQTPTVFAF CVFIDFKIHK VSPMNEYTFS

51 YRFNGKSWSL SIWADNPEEA RAKFRAAREN AHYDGEVVAK VYTFVNISWV

101 KKLYKRTKYL MGIKE*

*Fig. 33A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

Fig. 33A-1

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGGCCTGG ACAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CTGCCGAAGC

1101 ACAGCTGACC GCAACCGAGC GGCACATCAA ACTCGCCGTA CGCCAGGCTT

*Fig. 33A-2*

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 33B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TGLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 34A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 34A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGGCCTGG ACAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CTGCCGAAGC

1101 ACAGCTGACC GCAACCGAGC GGCACATCAA ACTCGCCGTA CGCCAGGCTT

*Fig. 34A-2*

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 34B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TGLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 35A*

1 ATGACATTGC TCAATCTAAT ATGCAAGATT ACGGTATTTC CGTTTGCCTG

51 ACACTGACGC CCTATTTGCA ACATGAACTA TTTTCGGCTA TGAAATCCTA

101 TTTTTCCAAA TATATCCTAC CCGTTTCACT TTTTACCTTG CCACTATCCC

151 TTTCCCCATC CGTTTCGGCT TTTACGCTGC CTGAAGCATG GCGGGCGGCG

201 CAGCAACATT CGGCTGATTT TCAAGCGTCC CATTACCAGC GTGATGCAGT

251 GCGCGCACGG CAACAACAAG CCAAGGCCGC ATTCCTTCCC CATGTATCCG

301 CCAATGCCAG CTACCAGCGC CAGCCGCCAT CGATTTCTTC CACCCGCGAA

351 ACACAGGGAT GGAGCGTGCA GGTGGGACAA ACCTTATTTG ACTCTGCCAA

401 ATTTGCACAA TACCGCCAAA GCAGGTTCGA TACGCAGGCT GCAGAACAGC

451 GTTTCGATGC GGCACGCGAA GAATTGCTGT TGAAAGTTGC CGAAAGTTAT

501 TTCAACGTTT TACTCAGCCG AGACACCGTT GCCGCCCATG CGGCGGAAAA

*Fig. 35A-1*

551 AGAGGCTTAT GCCCAGCAGG TAAGGCAGGC GCAGGCTTTA TTCAATAAAG

601 GTGCTGCCAC CGCGCTAGAT ATTCACGAAG CCAAAGCCGG TTACGACAAT

651 GCCCTGGCCC AAGAAATCGC CGTATTGGCT GAGAAACAAA CCTATGAAAA

701 CCAGTTGAAC GACTACACCG GCCTGGACAG CAAACAAATC GAGGCCATAG

751 ATACCGCCAA CCTGTTGGCA CGCTATCTGC CCAAGCTGGA ACGTTACAGT

801 CTGGATGAAT GGCAGCGCAT TGCCTTATCC AACAATCATG AATACCGGAT

851 GCAGCAGCTT GCCCTGCAAA GCAGCGGACA GGCGCTTCGG GCAGCACAGA

901 ACAGCCGCTA TCCCACCGTT TCTGCCCATG TCGGCTATCA GAATAACCTC

951 TACACTTCAT CTGCGCAGAA TAATGACTAC CACTATCGGG GCAAAGGGAT

1001 GAGCGTCGGC GTACAGTTGA ATTTGCCGCT TTATACCGGC GGAGAATTGT

1051 CGGGCAAAAT CCATGAAGCC GAAGCGCAAT ACGGGGCTGC CGAAGCACAG

1101 CTGACCGCAA CCGAGCGGCA CATCAAACTC GCCGTACGCC AGGCTTATAC

*Fig. 35A-2*

1151 CGAAAGCGGT GCGGCGCGTT ACCAAATCAT GGCGCAAGAA CGGGTTTTGG

1201 AAAGCAGCCG TTTGAAACTG AAATCGACCG AAACCGGCCA ACAATACGGC

1251 ATCCGCAACC GGCTGGAAGT AATACGGGCG CGGCAGGAAG TCGCCCAAGC

1301 AGAACAGAAA CTGGCTCAAG CACGGTATAA ATTCATGCTG GCTTATTTGC

1351 GCTTGGTGAA AGAGAGCGGG TTAGGGTTGG AAACGGTATT TGCGGAATAA

*Fig. 35B*

1 MTLLNLICKI TVFPFA*H*R PICNMNYFRL *NPIFPNISY PFHFLPCHYP

51 FPHPFRLLRC LKHGGRRSNI RLIFKRPITS VMQCAHGNNK PRPHSFPMYP

101 PMPATSASRH RFLPPAKHRD GACRWDKPYL TLPNLHNTAK AGSIRRLQNS

151 VSMRHAKNCC *KLPKVISTF YSAETPLPPM RRKKRLMPSR *GRRRLYSIK

201 VLPPR*IFTK PKPVTTMPWP KKSPYWLRNK PMKTS*TTTP AWTANKSRP*

251 IPPTCWHAIC PSWNVTVWMN GSALPYPTIM NTGCSSLPCK AADRRFGQHR

301 TAAIPPFLPM SAIRITSTLH LRRIMTTTIG AKG*ASAYS* ICRFIPAENC

351 RAKSMKPKRN TGLPKHS*PQ PSGTSNSPYA RLIPKAVRRV TKSWRKNGFW

401 KAAV*N*NRP KPANNTASAT GWK*YGRGRK SPKQNRNWLK HGINSCWLIC

451 AW*KRAG*GW KRYLRN

Fig. 36A

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 36A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

*Fig. 36A-2*

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 36B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 37A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 37A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

Fig. 37A-2

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 37B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 38A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 38A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

*Fig. 38A-2*

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 38B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQIT ATERHIKIAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

Fig. 39A

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 39A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAAGCTT

*Fig. 39A-2*

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 39B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 40A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 40A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

*Fig. 40A-2*

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 40B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 41A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

Fig. 41A-1

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

Fig. 41A-2

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 41B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 42A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 42A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

Fig. 42A-2

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 42B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 43A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 43A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

Fig. 43A-2

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

Fig. 43B

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 44A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

Fig. 44A-1

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

*Fig. 44B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

*Fig. 44B-1*

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 45A*

1 ATGACATTGC TCAATCTAAT GATAATGCAA GATTACGGTA TTTCCGTTTG

51 CCTGACACTG ACGCCCTATT TGCAACATGA ACTATTTTCG GCTATGAAAT

101 CCTATTTTTC CAAATATATC CTACCCGTTT CACTTTTTAC CTTGCCACTA

151 TCCCTTTCCC CATCCGTTTC GGCTTTTACG CTGCCTGAAG CATGGCGGGC

201 GGCGCAGCAA CATTCGGCTG ATTTTCAAGC GTCCCATTAC CAGCGTGATG

251 CAGTGCGCGC ACGGCAACAA CAAGCCAAGG CCGCATTCCT TCCCCATGTA

301 TCCGCCAATG CCAGCTACCA GCGCCAGCCG CCATCGATTT CTTCCACCCG

351 CGAAACACAG GGATGGAGCG TGCAGGTGGG ACAAACCTTA TTTGACGCTG

401 CCAAATTTGC ACAATACCGC CAAAGCAGGT TCGATACGCA GGCTGCAGAA

451 CAGCGTTTCG ATGCGGCACG CGAAGAATTG CTGTTGAAAG TTGCCGAAAG

501 TTATTTCAAC GTTTTACTCA GCCGAGACAC CGTTGCCGCC CATGCGGCGG

*Fig. 45A-1*

551 AAAAAGAGGC TTATGCCCAG CAGGTAAGGC AGGCGCAGGC TTTATTCAAT

601 AAAGGTGCTG CCACCGCGCT GGATATTCAC GAAGCCAAAG CCGGTTACGA

651 CAATGCCCTG GCCCAAGAAA TCGCCGTATT GGCTGAGAAA CAAACCTATG

701 AAAACCAGTT GAACGACTAC ACCGACCTGG ATAGCAAACA AATCGAGGCC

751 ATAGATACCG CCAACCTGTT GGCACGCTAT CTGCCCAAGC TGGAACGTTA

801 CAGTCTGGAT GAATGGCAGC GCATTGCCTT ATCCAACAAT CATGAATACC

851 GGATGCAGCA GCTTGCCCTG CAAAGCAGCG GACAGGCGCT TCGGGCAGCA

901 CAGAACAGCC GCTATCCCAC CGTTTCTGCC CATGTCGGCT ATCAGAATAA

951 CCTCTACACT TCATCTGCGC AGAATAATGA CTACCACTAT CGGGGCAAAG

1001 GGATGAGCGT CGGCGTACAG TTGAATTTGC CGCTTTATAC CGGCGGAGAA

1051 TTGTCGGGCA AAATCCATGA AGCCGAAGCG CAATACGGGG CCGCCGAAGC

1101 ACAGCTGACC GCAACCGAGC GGCACATCAA ACTCGCCGTA CGCCAGGCTT

Fig. 45A-2

1151 ATACCGAAAG CGGTGCGGCG CGTTACCAAA TCATGGCGCA AGAACGGGTT

1201 TTGGAAAGCA GCCGTTTGAA ACTGAAATCG ACCGAAACCG GCCAACAATA

1251 CGGCATCCGC AACCGGCTGG AAGTAATACG GGCGCGGCAG GAAGTCGCCC

1301 AAGCAGAACA GAAACTGGCT CAAGCACGGT ATAAATTCAT GCTGGCTTAT

1351 TTGCGCTTGG TGAAAGAGAG CGGGTTAGGG TTGGAAACGG TATTTGCGGA

1401 ATAA

*Fig. 45B*

1 MTLLNLMIMQ DYGISVCLTL TPYLQHELFS AMKSYFSKYI LPVSLFTLPL

51 SLSPSVSAFT LPEAWRAAQQ HSADFQASHY QRDAVRARQQ QAKAAFLPHV

101 SANASYQRQP PSISSTRETQ GWSVQVGQTL FDAAKFAQYR QSRFDTQAAE

151 QRFDAAREEL LLKVAESYFN VLLSRDTVAA HAAEKEAYAQ QVRQAQALFN

201 KGAATALDIH EAKAGYDNAL AQEIAVLAEK QTYENQLNDY TDLDSKQIEA

251 IDTANLLARY LPKLERYSLD EWQRIALSNN HEYRMQQLAL QSSGQALRAA

301 QNSRYPTVSA HVGYQNNLYT SSAQNNDYHY RGKGMSVGVQ LNLPLYTGGE

351 LSGKIHEAEA QYGAAEAQLT ATERHIKLAV RQAYTESGAA RYQIMAQERV

401 LESSRLKLKS TETGQQYGIR NRLEVIRARQ EVAQAEQKLA QARYKFMLAY

451 LRLVKESGLG LETVFAE*

Bactericidal assay. Anti-DsbA1 and Preimmune
15 June 1999

Bactericidal assay. 8013 and 8013-DsbA1
21 June 1999

SEQUENCE LISTING

<160> NUMBER OF SEQ ID NOS: 116

<210> SEQ ID NO 1
<211> LENGTH: 696
<212> TYPE: DNA
<213> ORGANISM: Neisseria meningitidis

<400> SEQUENCE: 1

```
atgaaactga aaaccttagc tttgacttca ttgaccctgt tggcattggc cgcttgtagc     60

aaacaggctg aaaccagtgt tccggcagac agcgcccaaa gcagctcatc tgctccggca    120

gcccctgctg agttgaacga aggtgtgaac tacactgtat tgtctacgcc tattccgcaa    180

cagcaggccg gtaaaatcga agtattggaa tttttcggct acttctgccc gcattgcgcc    240

catcttgagc cggtcttgag cgagcacatc aaaacgttta aagacgatac ctatatgcgc    300

cgggagcatg tcgtgtgggg tgatgaaatg aaacctttgg cacgtttggc ggccgcagtg    360

gaaatggccg gtgaatcaga taaagccaac agccatattt tcgatgcgat ggttaatcaa    420

aaaatcaatc tggccgatac cgataccctg aaaaaatggc tgtccgagca aacagcgttt    480

gacggcaaaa aagtattggc tgcatttgag gctcctgaaa gccaagcgcg tgcggctcaa    540

atggaagagt tgaccaataa attccaaatc agcggcacac cgactgtgat tgtcggcggc    600

aaataccaag ttgaatttaa agactggcag tccggtatga ccacgattga ccagttggtg    660

gataaagtac gcgaagagca gaaaaagccg caataa                              696
```

<210> SEQ ID NO 2
<211> LENGTH: 231
<212> TYPE: PRT
<213> ORGANISM: Neisseria meningitidis

<400> SEQUENCE: 2

```
Met Lys Leu Lys Thr Leu Ala Leu Thr Ser Leu Thr Leu Leu Ala Leu
1               5                   10                  15

Ala Ala Cys Ser Lys Gln Ala Glu Thr Ser Val Pro Ala Asp Ser Ala
            20                  25                  30

Gln Ser Ser Ser Ser Ala Pro Ala Ala Pro Ala Glu Leu Asn Glu Gly
        35                  40                  45

Val Asn Tyr Thr Val Leu Ser Thr Pro Ile Pro Gln Gln Gln Ala Gly
    50                  55                  60

Lys Ile Glu Val Leu Glu Phe Phe Gly Tyr Phe Cys Pro His Cys Ala
65                  70                  75                  80

His Leu Glu Pro Val Leu Ser Glu His Ile Lys Thr Phe Lys Asp Asp
                85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190
```

-continued

```
Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230


<210> SEQ ID NO 3
<211> LENGTH: 696
<212> TYPE: DNA
<213> ORGANISM: Neisseria meningitidis

<400> SEQUENCE: 3

atgaaactga aaaccttagc tttgacttca ttgaccctgt tggcattggc cgcttgtagc      60

aaacaggctg aaaccagtgt tccggcagac agcgcccaaa gcagctcatc tgctccggca     120

gcccctgctg agttgaacga aggtgtgaac tacactgtat tgtctacgcc tattccgcaa     180

cagcaggccg gtaaaatcga agtattggaa tttttcggct acttctgccc gcattgcgcc     240

catcttgagc cggtcttgag cgagcacatc aaaacgttta aagacgatac ctatatgcgc     300

cgggagcatg tcgtgtgggg tgatgaaatg aaacctttgg cacgtttggc ggccgcagtg     360

gaaatggccg gtgaatcaga taaagccaac agccatattt tcgatgcgat ggttaatcaa     420

aaaatcaatc tggccgatac cgataccctg aaaaaatggc tgtccgagca aacagcgttt     480

gacggcaaaa aagtattggc tgcatttgag gctcctgaaa gccaagcgcg tgcggctcaa     540

atggaagagt tgaccaataa attccaaatc agcggcacac cgactgtgat tgtcggcggc     600

aaataccaag ttgaatttaa agactggcag tccggtatga ccacgattga ccagttggtg     660

gataaagtac gcgaagagca gaaaaagccg caataa                               696


<210> SEQ ID NO 4
<211> LENGTH: 231
<212> TYPE: PRT
<213> ORGANISM: Neisseria meningitidis

<400> SEQUENCE: 4

Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Ala
             20                  25                  30

Gln Ser Ser Ser Ser Ala Pro Ala Ala Pro Ala Glu Leu Asn Glu Gly
         35                  40                  45

Val Asn Tyr Thr Val Leu Ser Thr Pro Ile Pro Gln Gln Gln Ala Gly
     50                  55                  60

Lys Ile Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160
```

-continued

```
Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230


<210> SEQ ID NO 5
<211> LENGTH: 696
<212> TYPE: DNA
<213> ORGANISM: Neisseria meningitidis

<400> SEQUENCE: 5

atgaaactga aaaccttagc tttgacttca ttgaccctgt tggcattggc cgcttgtagc      60

aaacaggctg aaaccagtgt tccggcagac agcgcccaaa gcagctcatc tgctccggca     120

gcccctgctg agttgaacga aggtgtgaac tacactgtat tgtctacgcc tattccgcaa     180

cagcaggccg gtaaaatcga agtattggaa tttttcggct acttctgccc gcattgcgcc     240

catcttgagc cggtcttgag cgagcacatc aaaacgttta aagacgatac ctatatgcgc     300

cgggagcatg tcgtgtgggg tgatgaaatg aaacctttgg cacgtttggc ggccgcagtg     360

gaaatggccg gtgaatcaga taaagccaac agccatattt tcgatgcgat ggttaatcaa     420

aaaatcaatc tggccgatac cgataccctg aaaaaatggc tgtccgagca aacagcgttt     480

gacggcaaaa aagtattggc tgcatttgag gctcctgaaa gccaagcgcg tgcggctcaa     540

atggaagagt tgaccaataa attccaaatc agcggcacac cgactgtgat tgtcggcggc     600

aaataccaag ttgaatttaa agactggcag tccggtatga ccacgattga ccagttggtg     660

gataaagtac gcgaagagca gaaaaagccg caataa                               696


<210> SEQ ID NO 6
<211> LENGTH: 231
<212> TYPE: PRT
<213> ORGANISM: Neisseria meningitidis

<400> SEQUENCE: 6

Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Ala
             20                  25                  30

Gln Ser Ser Ser Ser Ala Pro Ala Ala Pro Ala Glu Leu Asn Glu Gly
         35                  40                  45

Val Asn Tyr Thr Val Leu Ser Thr Pro Ile Pro Gln Gln Gln Ala Gly
     50                  55                  60

Lys Ile Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125
```

-continued

```
Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230


<210> SEQ ID NO 7
<211> LENGTH: 696
<212> TYPE: DNA
<213> ORGANISM: Neisseria meningitidis

<400> SEQUENCE: 7

atgaaactga aaaccttagc tttgacttca ttgaccctgt tggcattggc cgcttgtagc      60

aaacaggctg aaaccagtgt tccggcagac agcgcccaaa gcagctcatc tgctccggca     120

gcccctgctg agttgaacga aggtgtgaac tacactgtat tgtctacgcc tattccgcaa     180

cagcaggccg gtaaaatcga agtattggaa tttttcggct acttctgccc gcattgcgcc     240

catcttgagc cggtcttgag cgagcacatc aaaacgttta aagacgatac ctatatgcgc     300

cgggagcatg tcgtgtgggg tgatgaaatg aaacctttgg cacgtttggc ggccgcagtg     360

gaaatggccg gtgaatcaga taaagccaac agccatattt tcgatgcgat ggttaatcaa     420

aaaatcaatc tggccgatac cgataccctg aaaaaatggc tgtccgagca aacagcgttt     480

gacggcaaaa aagtattggc tgcatttgag gctcctgaaa gccaagcgcg tgcggctcaa     540

atggaagagt tgaccaataa attccaaatc agcggcacac cgactgtgat tgtcggcggc     600

aaataccaag ttgaatttaa agactggcag tccggtatga ccacgattga ccagttggtg     660

gataaagtac gcgaagagca gaaaaagccg caataa                               696


<210> SEQ ID NO 8
<211> LENGTH: 231
<212> TYPE: PRT
<213> ORGANISM: Neisseria meningitidis

<400> SEQUENCE: 8

Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Ala
            20                  25                  30

Gln Ser Ser Ser Ser Ala Pro Ala Ala Pro Ala Glu Leu Asn Glu Gly
         35                  40                  45

Val Asn Tyr Thr Val Leu Ser Thr Pro Ile Pro Gln Gln Gln Ala Gly
     50                  55                  60

Lys Ile Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95
```

-continued

```
Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230
```

<210> SEQ ID NO 9
<211> LENGTH: 696
<212> TYPE: DNA
<213> ORGANISM: Neisseria meningitidis

<400> SEQUENCE: 9

```
atgaaactga aaaccttagc tttgacttca ttgaccctgt tggcattggc cgcttgtagc      60

aaacaggctg aaaccagtgt tccggcagac agcgcccaaa gcagctcatc tgctccggca     120

gcccctgctg agttgaacga aggtgtgaac tacactgtat tgtctacgcc tattccgcaa     180

cagcaggccg gtaaaatcga agtattggaa tttttcggct acttctgccc gcattgcgcc     240

catcttgagc cggtcttgag cgagcacatc aaaacgttta aagacgatac ctatatgcgc     300

cgggagcatg tcgtgtgggg tgatgaaatg aaacctttgg cacgtttggc ggccgcagtg     360

gaaatggccg gtgaatcaga taaagccaac agccatattt tcgatgcgat ggttaatcaa     420

aaaatcaatc tggccgatac cgataccctg aaaaaatggc tgtccgagca aacagcgttt     480

gacggcaaaa aagtattggc tgcatttgag gctcctgaaa gccaagcgcg tgcggctcaa     540

atggaagagt tgaccaataa attccaaatc agcggcacac cgactgtgat tgtcggcggc     600

aaataccaag ttgaatttaa agactggcag tccggtatga ccacgattga ccagttggtg     660

gataaagtac gcgaagagca gaaaaagccg caataa                               696
```

<210> SEQ ID NO 10
<211> LENGTH: 231
<212> TYPE: PRT
<213> ORGANISM: Neisseria meningitidis

<400> SEQUENCE: 10

```
Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Ala
             20                  25                  30

Gln Ser Ser Ser Ser Ala Pro Ala Ala Pro Ala Glu Leu Asn Glu Gly
         35                  40                  45

Val Asn Tyr Thr Val Leu Ser Thr Pro Ile Pro Gln Gln Gln Ala Gly
     50                  55                  60
```

-continued

```
Lys Ile Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230


<210> SEQ ID NO 11
<211> LENGTH: 696
<212> TYPE: DNA
<213> ORGANISM: Neisseria meningitidis

<400> SEQUENCE: 11

atgaaactga aaaccttagc tttgacttca ttgaccctgt tggcattggc cgcttgtagc      60

aaacaggctg aaaccagtgt tccggcagac agcgcccaaa gcagctcatc tgctccggca     120

gcccctgctg agttgaacga aggtgtgaac tacactgtat tgtctacgcc tattccgcaa     180

cagcaggccg gtaaaatcga agtattggaa tttttcggct acttctgccc gcattgcgcc     240

catcttgagc cggtcttgag cgagcacatc aaaacgttta aagacgatac ctatatgcgc     300

cgggagcatg tcgtgtgggg tgatgaaatg aaacctttgg cacgtttggc ggccgcagtg     360

gaaatggccg gtgaatcaga taaagccaac agccatattt tcgatgcgat ggttaatcaa     420

aaaatcaatc tggccgatac cgataccctg aaaaaatggc tgtccgagca aacagcgttt     480

gacggcaaaa aagtattggc tgcatttgag gctcctgaaa gccaagcgcg tgcggctcaa     540

atggaagagt tgaccaataa attccaaatc agcggcacac cgactgtgat tgtcggcggc     600

aaataccaag ttgaatttaa agactggcag tccggtatga ccacgattga ccagttggtg     660

gataaagtac gcgaagagca gaaaaagccg caataa                               696


<210> SEQ ID NO 12
<211> LENGTH: 231
<212> TYPE: PRT
<213> ORGANISM: Neisseria meningitidis

<400> SEQUENCE: 12

Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Ala
             20                  25                  30
```

-continued

```
Gln Ser Ser Ser Ser Ala Pro Ala Ala Pro Ala Glu Leu Asn Glu Gly
        35                  40                  45

Val Asn Tyr Thr Val Leu Ser Thr Pro Ile Pro Gln Gln Gln Ala Gly
    50                  55                  60

Lys Ile Glu Val Leu Glu Phe Phe Gly Tyr Phe Cys Pro His Cys Ala
65                  70                  75                  80

His Leu Glu Pro Val Leu Ser Glu His Ile Lys Thr Phe Lys Asp Asp
                85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230
```

<210> SEQ ID NO 13
<211> LENGTH: 696
<212> TYPE: DNA
<213> ORGANISM: Neisseria meningitidis

<400> SEQUENCE: 13

```
atgaaactga aaaccttagc tttgacttca ttgaccctgt tggcattggc cgcttgtagc      60

aaacaggctg aaaccagtgt tccggcagac agcgcccaaa gcagctcatc tgctccggca     120

gcccctgctg agttgaacga aggtgtgaac tacactgtat tgtctacgcc tattccgcaa     180

cagcaggccg gtaaaatcga agtattggaa tttttcggct acttctgccc gcattgcgcc     240

catcttgagc cggtcttgag cgagcacatc aaaacgttta aagacgatac ctatatgcgc     300

cgggagcatg tcgtgtgggg tgatgaaatg aaacctttgg cacgtttggc ggccgcagtg     360

gaaatggccg gtgaatcaga taaagccaac agccatattt tcgatgcgat ggttaatcaa     420

aaaatcaatc tggccgatac cgataccctg aaaaaatggc tgtccgagca aacagcgttt     480

gacggcaaaa aagtattggc tgcatttgag gctcctgaaa gccaagcgcg tgcggctcaa     540

atggaagagt tgaccaataa attccaaatc agcggcacac cgactgtgat tgtcggcggc     600

aaataccaag ttgaatttaa agactggcag tccggtatga ccacgattga ccagttggtg     660

gataaagtac gcgaagagca gaaaaagccg caataa                               696
```

<210> SEQ ID NO 14
<211> LENGTH: 231
<212> TYPE: PRT
<213> ORGANISM: Neisseria meningitidis

<400> SEQUENCE: 14

-continued

```
Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Ala
             20                  25                  30

Gln Ser Ser Ser Ser Ala Pro Ala Ala Pro Ala Glu Leu Asn Glu Gly
         35                  40                  45

Val Asn Tyr Thr Val Leu Ser Thr Pro Ile Pro Gln Gln Gln Ala Gly
     50                  55                  60

Lys Ile Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230
```

<210> SEQ ID NO 15
<211> LENGTH: 696
<212> TYPE: DNA
<213> ORGANISM: Neisseria meningitidis

<400> SEQUENCE: 15

```
atgaaactga aaaccttagc tttgacttca ttgaccctgt tggcattggc cgcttgtagc      60

aaacaggctg aaaccagtgt tccggcagac agcgcccaaa gcagctcatc tgctccggca     120

gcccctgctg agttgaacga aggtgtgaac tacactgtat tgtctacgcc tattccgcaa     180

cagcaggccg gtaaaatcga agtattggaa tttttcggct acttctgccc gcattgcgcc     240

catcttgagc cggtcttgag cgagcacatc aaaacgttta aagacgatac ctatatgcgc     300

cgggagcatg tcgtgtgggg tgatgaaatg aaacctttgg cacgtttggc ggccgcagtg     360

gaaatggccg gtgaatcaga taaagccaac agccatattt tcgatgcgat ggttaatcaa     420

aaaatcaatc tggccgatac cgataccctg aaaaaatggc tgtccgagca aacagcgttt     480

gacggcaaaa aagtattggc tgcatttgag gctcctgaaa gccaagcgcg tgcggctcaa     540

atggaagagt tgaccaataa attccaaatc agcggcacac cgactgtgat tgtcggcggc     600

aaataccaag ttgaatttaa agactggcag tccggtatga ccacgattga ccagttggtg     660

gataaagtac gcgaagagca gaaaaagccg caataa                               696
```

-continued

<210> SEQ ID NO 16
<211> LENGTH: 231
<212> TYPE: PRT
<213> ORGANISM: Neisseria meningitidis

<400> SEQUENCE: 16

```
Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Ala
             20                  25                  30

Gln Ser Ser Ser Ser Ala Pro Ala Ala Pro Ala Glu Leu Asn Glu Gly
         35                  40                  45

Val Asn Tyr Thr Val Leu Ser Thr Pro Ile Pro Gln Gln Gln Ala Gly
     50                  55                  60

Lys Ile Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230
```

<210> SEQ ID NO 17
<211> LENGTH: 696
<212> TYPE: DNA
<213> ORGANISM: Neisseria meningitidis

<400> SEQUENCE: 17

```
atgaaactga aaaccttagc tttgacttca ttgaccctgt tggcattggc cgcttgtagc      60

aaacaggctg aaaccagtgt tccggcagac agcgcccaaa gcagctcatc tgctccggca     120

gcccctgctg agttgaacga aggtgtgaac tacactgtat tgtctacgcc tattccgcaa     180

cagcaggccg gtaaaatcga agtattggaa tttttcggct acttctgccc gcattgcgcc     240

catcttgagc cggtcttgag cgagcacatc aaaacgttta aagacgatac ctatatgcgc     300

cgggagcatg tcgtgtgggg tgatgaaatg aaacctttgg cacgtttggc ggccgcagtg     360

gaaatggccg gtgaatcaga taaagccaac agccatattt tcgatgcgat ggttaatcaa     420

aaaatcaatc tggccgatac cgataccctg aaaaaatggc tgtccgagca aacagcgttt     480

gacggcaaaa aagtattggc tgcatttgag gctcctgaaa gccaagcgcg tgcggctcaa     540

atggaagagt tgaccaataa attccaaatc agcggcacac cgactgtgat tgtcggcggc     600
```

-continued

```
aaataccaag ttgaatttaa agactggcag tctggtatga ccacgattga ccagttggtg    660

gataaagtac gcgaagagca gaaaaagccg caataa                              696


<210> SEQ ID NO 18
<211> LENGTH: 231
<212> TYPE: PRT
<213> ORGANISM: Neisseria meningitidis

<400> SEQUENCE: 18

Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Ala
             20                  25                  30

Gln Ser Ser Ser Ser Ala Pro Ala Ala Pro Ala Glu Leu Asn Glu Gly
         35                  40                  45

Val Asn Tyr Thr Val Leu Ser Thr Pro Ile Pro Gln Gln Gln Ala Gly
     50                  55                  60

Lys Ile Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230


<210> SEQ ID NO 19
<211> LENGTH: 696
<212> TYPE: DNA
<213> ORGANISM: Neisseria meningitidis

<400> SEQUENCE: 19

atgaaactga aaaccttagc tttgacttca ttgaccctgt tggcattggc cgcttgtagc     60

aaacaggctg aaaccagtgt tccggcagac agcgcccaaa gcagctcatc tgctccggca    120

gcccctgctg agttgaacga aggtgtgaac tacactgtat tgtctacgcc tattccgcaa    180

cagcaggccg gtaaaatcga agtattggaa tttttcggct acttctgccc gcattgcgcc    240

catcttgagc cggtcttgag cgagcacatc aaaacgttta aagacgatac ctatatgcgc    300

cgggagcatg tcgtgtgggg tgatgaaatg aaacctttgg cacgtttggc ggccgcagtg    360

gaaatggccg gtgaatcaga taaagccaac agccatattt tcgatgcgat ggttaatcaa    420
```

-continued aaaatcaatc tggccgatac cgataccctg aaaaaatggc tgtccgagca aacagcgttt 480
gacggcaaaa aagtattggc tgcatttgag gctcctgaaa gccaagcgcg tgcggctcaa 540
atggaagagt tgaccaataa attccaaatc agcggcacac cgactgtgat tgtcggcggc 600
aaataccaag ttgaatttaa agactggcag tctggtatga ccacgattga ccagttggtg 660
gataaagtac gcgaagagca gaaaaagccg caataa 696

<210> SEQ ID NO 20
<211> LENGTH: 231
<212> TYPE: PRT
<213> ORGANISM: Neisseria meningitidis

<400> SEQUENCE: 20

Met Lys Leu Lys Thr Leu Ala Leu Thr Ser Leu Thr Leu Leu Ala Leu
1 5 10 15

Ala Ala Cys Ser Lys Gln Ala Glu Thr Ser Val Pro Ala Asp Ser Ala
20 25 30

Gln Ser Ser Ser Ser Ala Pro Ala Ala Pro Ala Glu Leu Asn Glu Gly
35 40 45

Val Asn Tyr Thr Val Leu Ser Thr Pro Ile Pro Gln Gln Ala Gly
50 55 60

Lys Ile Glu Val Leu Glu Phe Phe Gly Tyr Phe Cys Pro His Cys Ala
65 70 75 80

His Leu Glu Pro Val Leu Ser Glu His Ile Lys Thr Phe Lys Asp Asp
85 90 95

Thr Tyr Met Arg Arg Glu His Val Val Trp Gly Asp Glu Met Lys Pro
100 105 110

Leu Ala Arg Leu Ala Ala Ala Val Glu Met Ala Gly Glu Ser Asp Lys
115 120 125

Ala Asn Ser His Ile Phe Asp Ala Met Val Asn Gln Lys Ile Asn Leu
130 135 140

Ala Asp Thr Asp Thr Leu Lys Lys Trp Leu Ser Glu Gln Thr Ala Phe
145 150 155 160

Asp Gly Lys Lys Val Leu Ala Ala Phe Glu Ala Pro Glu Ser Gln Ala
165 170 175

Arg Ala Ala Gln Met Glu Glu Leu Thr Asn Lys Phe Gln Ile Ser Gly
180 185 190

Thr Pro Thr Val Ile Val Gly Gly Lys Tyr Gln Val Glu Phe Lys Asp
195 200 205

Trp Gln Ser Gly Met Thr Thr Ile Asp Gln Leu Val Asp Lys Val Arg
210 215 220

Glu Glu Gln Lys Lys Pro Gln
225 230

<210> SEQ ID NO 21
<211> LENGTH: 696
<212> TYPE: DNA
<213> ORGANISM: Neisseria meningitidis

<400> SEQUENCE: 21
atgaaactga aaaccttagc tttgacttca ttgaccctgt tggcattggc cgcttgtagc 60
aaacaggctg aaaccagcgt tccggcagac agcgtccaaa gcagctcatc tgctccggca 120
gccccagccc cattgaccga aggcgtgaac tacactgtat tgtccacgcc tatcccgcaa 180
cagcaggccg gcaaagtcga agtcttggaa tttttcggct acttctgccc gcattgcgcc 240

-continued

```
catcttgagc cggtcttgag cgagcacatc aaaacgttta aagacgatac ctatatgcgc    300

cgggagcatg tcgtgtgggg tgatgaaatg aaacctttgg cacgtttggc ggccgcagtg    360

gaaatggccg gtgaatcaga taaagccaac agccatattt tcgatgcgat ggttaatcaa    420

aaaatcaatc tggccgatac cgataccctg aaaaaatggc tgtccgagca aacagcgttt    480

gacggcaaaa aagtattggc tgcatttgag gcttctgaaa gccaagcgcg tgcggctcaa    540

atggaagagt tgaccaataa attccaaatc agcggcacac cgactgtgat cgtcggcggc    600

aaataccaag ttgaatttaa agactggcag tccggtatga ccacgattga ccagttggtg    660

gataaagtac gcgaagagca gaaaaagccg caataa                              696
```

<210> SEQ ID NO 22
<211> LENGTH: 231
<212> TYPE: PRT
<213> ORGANISM: Neisseria meningitidis

<400> SEQUENCE: 22

```
Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Val
             20                  25                  30

Gln Ser Ser Ser Ser Ala Pro Ala Ala Pro Ala Pro Leu Thr Glu Gly
         35                  40                  45

Val Asn Tyr Thr Val Leu Ser Thr Pro Ile Pro Gln Gln Gln Ala Gly
     50                  55                  60

Lys Val Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Ser Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230
```

<210> SEQ ID NO 23
<211> LENGTH: 696
<212> TYPE: DNA
<213> ORGANISM: Neisseria meningitidis

<400> SEQUENCE: 23

```
atgaaactga aaaccttagc tttgacttca ttgaccctgt tggcattggc cgcttgtagc     60
```

-continued

```
aaacaggctg aaaccagcgt tccggcagac agcgtccaaa gcagctcatc tgctccggca    120

gccccagccc cattgaccga aggcgtgaac tacactgtat tgtccacgcc tatcccgcaa    180

cagcaggccg gcaaagtcga agtcttggaa tttttcggct acttctgccc gcattgcgcc    240

catcttgagc cggtcttgag cgagcacatc aaaacgttta aagacgatac ctatatgcgc    300

cgggagcatg tcgtgtgggg tgatgaaatg aaacctttgg cacgtttggc ggccgcagtg    360

gaaatggccg gtgaatcaga taaagccaac agccatattt tcgatgcgat ggttaatcaa    420

aaaatcaatc tggccgatac cgataccctg aaaaaatggc tgtccgagca aacagcgttt    480

gacggcaaaa aagtattggc tgcatttgag gcttctgaaa gccaagcgcg tgcggctcaa    540

atggaagagt tgaccaataa attccaaatc agcggcacac cgactgtgat cgtcggcggc    600

aaataccaag ttgaatttaa agactggcag tccggtatga ccacgattga ccagttggtg    660

gataaagtac gcgaagagca gaaaaagccg caataa                              696
```

<210> SEQ ID NO 24
<211> LENGTH: 231
<212> TYPE: PRT
<213> ORGANISM: Neisseria meningitidis

<400> SEQUENCE: 24

```
Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Val
             20                  25                  30

Gln Ser Ser Ser Ser Ala Pro Ala Ala Pro Ala Pro Leu Thr Glu Gly
         35                  40                  45

Val Asn Tyr Thr Val Leu Ser Thr Pro Ile Pro Gln Gln Gln Ala Gly
     50                  55                  60

Lys Val Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Ser Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220

Glu Glu Gln Lys Lys Pro Gln
225                 230
```

<210> SEQ ID NO 25
<211> LENGTH: 696

-continued

<212> TYPE: DNA
<213> ORGANISM: Neisseria meningitidis

<400> SEQUENCE: 25

```
atgaaactga aaaccttagc tttgacttca ttgaccctgt tggcattggc cgcttgtagc     60

aaacaggctg aaaccagcgt tccggcagac agcgtccaaa gcagctcatc tgctccggca    120

gccccagccc cattgaccga aggcgtgaac tacactgtat tgtccacgcc tatcccgcaa    180

cagcaggccg gcaaagtcga agtcttggaa tttttcggct acttctgccc gcattgcgcc    240

catcttgagc cggtcttgag cgagcacatc aaaacgttta aagacgatac ctatatgcgc    300

cgggagcatg tcgtgtgggg tgatgaaatg aaacctttgg cacgtttggc ggccgcagtg    360

gaaatggccg gtgaatcaga taaagccaac agccatattt tcgatgcgat ggttaatcaa    420

aaaatcaatc tggccgatac cgataccctg aaaaaatggc tgtccgagca aacagcgttt    480

gacggcaaaa aagtattggc tgcatttgag gctcctgaaa gccaagcgcg tgcggctcaa    540

atggaagagt tgaccaataa attccaaatc agcggcacac cgactgtgat tgtcggcggc    600

aaataccaag ttgaatttaa agactggcag tccggtatga ccacgattga ccagttggtg    660

gataaagtac gcgaagagca gaaaaagccg caataa                              696
```

<210> SEQ ID NO 26
<211> LENGTH: 231
<212> TYPE: PRT
<213> ORGANISM: Neisseria meningitidis

<400> SEQUENCE: 26

```
Met Lys Leu Lys Thr Leu Ala Leu Thr Ser Leu Thr Leu Leu Ala Leu
  1               5                  10                  15

Ala Ala Cys Ser Lys Gln Ala Glu Thr Ser Val Pro Ala Asp Ser Val
             20                  25                  30

Gln Ser Ser Ser Ser Ala Pro Ala Ala Pro Ala Pro Leu Thr Glu Gly
         35                  40                  45

Val Asn Tyr Thr Val Leu Ser Thr Pro Ile Pro Gln Gln Gln Ala Gly
     50                  55                  60

Lys Val Glu Val Leu Glu Phe Phe Gly Tyr Phe Cys Pro His Cys Ala
 65                  70                  75                  80

His Leu Glu Pro Val Leu Ser Glu His Ile Lys Thr Phe Lys Asp Asp
                 85                  90                  95

Thr Tyr Met Arg Arg Glu His Val Val Trp Gly Asp Glu Met Lys Pro
            100                 105                 110

Leu Ala Arg Leu Ala Ala Ala Val Glu Met Ala Gly Glu Ser Asp Lys
        115                 120                 125

Ala Asn Ser His Ile Phe Asp Ala Met Val Asn Gln Lys Ile Asn Leu
    130                 135                 140

Ala Asp Thr Asp Thr Leu Lys Lys Trp Leu Ser Glu Gln Thr Ala Phe
145                 150                 155                 160

Asp Gly Lys Lys Val Leu Ala Ala Phe Glu Ala Pro Glu Ser Gln Ala
                165                 170                 175

Arg Ala Ala Gln Met Glu Glu Leu Thr Asn Lys Phe Gln Ile Ser Gly
            180                 185                 190

Thr Pro Thr Val Ile Val Gly Gly Lys Tyr Gln Val Glu Phe Lys Asp
        195                 200                 205

Trp Gln Ser Gly Met Thr Thr Ile Asp Gln Leu Val Asp Lys Val Arg
    210                 215                 220
```

-continued

```
Glu Glu Gln Lys Lys Pro Gln
225                 230


<210> SEQ ID NO 27
<211> LENGTH: 1047
<212> TYPE: DNA
<213> ORGANISM: Neisseria meningitidis

<400> SEQUENCE: 27

gagtatgctc ttagagaaaa attgatcaaa aaagccaaag ggaaaggcct attatcttta      60

gattggggca gcctgaccga acaagaggca aggcagttta tctatttgat tgagaaagat     120

cgatattcta atcaattgct tgaccgatat caaaaaaatc caagtagttt aaataatcaa     180

gaaaaaaata ttcttgcata ttttattaac caaacctctg gaggtaacac agcttgggca     240

gcttcgatac tgaaaacgcc ccagtcaatg ggtaatctca ctattccttc caaagatatt     300

aataacacct tatcgaaagc ctatcaaaca ttgagtcgtt atgattcttt tgattacaaa     360

tcagctgttg ccgcacaacc tgcactttac ttattaaacg gaccgcttgg cttcagtgtc     420

aaagcagcta ctgtggcagc aggaggatat aacattggac agggagcgaa agcaatctct     480

aatggagaat atctgcatgg tacagttcag gttgttaatg gcacattgat ggttgcagga     540

tctgtatctg cacaggctgc aatatcggcc aagcctgcac ctgttacccg ttatctgagc     600

aatgacagtg ctcctgcttt aagacaagct ttaactgctg aaagccagag aatccgcatg     660

aaactgccgg aagagtatcg acaaataggg aatcttgcga tagcaaaaat tgatgttaaa     720

ggattaccgc aaaggatgga agcatttagt tctttccaaa aaggggaaca tggatttatt     780

tcgttacctg aaacaaaaat ttttaaacct atatctgttg ataaatatca taatattgcc     840

tctcctccta gaggaacatt aagaaatata gatggagaat ataaattact tgaaactata     900

gcacagcaac tcggaaataa tcgtaatgta tcaggtagaa ttgatctatt tacagaatta     960

aaggcctgtc aatcttgcag caatgttatt ttagagttta gaaatcgcta tccaaatatt    1020

caattaaata tttttacagg aaaatag                                        1047


<210> SEQ ID NO 28
<211> LENGTH: 348
<212> TYPE: PRT
<213> ORGANISM: Neisseria meningitidis

<400> SEQUENCE: 28

Glu Tyr Ala Leu Arg Glu Lys Leu Ile Lys Lys Ala Lys Gly Lys Gly
  1               5                  10                  15

Leu Leu Ser Leu Asp Trp Gly Ser Leu Thr Glu Gln Glu Ala Arg Gln
             20                  25                  30

Phe Ile Tyr Leu Ile Glu Lys Asp Arg Tyr Ser Asn Gln Leu Leu Asp
         35                  40                  45

Arg Tyr Gln Lys Asn Pro Ser Ser Leu Asn Asn Gln Glu Lys Asn Ile
     50                  55                  60

Leu Ala Tyr Phe Ile Asn Gln Thr Ser Gly Gly Asn Thr Ala Trp Ala
 65                  70                  75                  80

Ala Ser Ile Leu Lys Thr Pro Gln Ser Met Gly Asn Leu Thr Ile Pro
                 85                  90                  95

Ser Lys Asp Ile Asn Asn Thr Leu Ser Lys Ala Tyr Gln Thr Leu Ser
            100                 105                 110

Arg Tyr Asp Ser Phe Asp Tyr Lys Ser Ala Val Ala Ala Gln Pro Ala
        115                 120                 125
```

-continued

```
Leu Tyr Leu Leu Asn Gly Pro Leu Gly Phe Ser Val Lys Ala Ala Thr
    130                 135                 140

Val Ala Ala Gly Gly Tyr Asn Ile Gly Gln Gly Ala Lys Ala Ile Ser
145                 150                 155                 160

Asn Gly Glu Tyr Leu His Gly Thr Val Gln Val Val Asn Gly Thr Leu
                165                 170                 175

Met Val Ala Gly Ser Val Ser Ala Gln Ala Ala Ile Ser Ala Lys Pro
            180                 185                 190

Ala Pro Val Thr Arg Tyr Leu Ser Asn Asp Ser Ala Pro Ala Leu Arg
        195                 200                 205

Gln Ala Leu Thr Ala Glu Ser Gln Arg Ile Arg Met Lys Leu Pro Glu
    210                 215                 220

Glu Tyr Arg Gln Ile Gly Asn Leu Ala Ile Ala Lys Ile Asp Val Lys
225                 230                 235                 240

Gly Leu Pro Gln Arg Met Glu Ala Phe Ser Ser Phe Gln Lys Gly Glu
                245                 250                 255

His Gly Phe Ile Ser Leu Pro Glu Thr Lys Ile Phe Lys Pro Ile Ser
            260                 265                 270

Val Asp Lys Tyr His Asn Ile Ala Ser Pro Pro Arg Gly Thr Leu Arg
        275                 280                 285

Asn Ile Asp Gly Glu Tyr Lys Leu Leu Glu Thr Ile Ala Gln Gln Leu
    290                 295                 300

Gly Asn Asn Arg Asn Val Ser Gly Arg Ile Asp Leu Phe Thr Glu Leu
305                 310                 315                 320

Lys Ala Cys Gln Ser Cys Ser Asn Val Ile Leu Glu Phe Arg Asn Arg
                325                 330                 335

Tyr Pro Asn Ile Gln Leu Asn Ile Phe Thr Gly Lys
            340                 345
```

<210> SEQ ID NO 29
<211> LENGTH: 2112
<212> TYPE: DNA
<213> ORGANISM: Neisseria meningitidis

<400> SEQUENCE: 29

```
atgaaaatat catttcattt agctttatta cccacgctga ttattgcttc cttccctgtt      60

gctgccgccg atacgcagga caatggtgaa cattacaccg ccactctgcc caccgtttcc     120

gtggtcggac agtccgacac cagcgtactc aaaggctaca tcaactacga cgaagccgcc     180

gttacccgca acggacagct catcaaagaa acgccgcaaa ccatcgatac gctcaatatc     240

cagaaaaaca aaaattacgg cacgaacgat ttgagttcca tcctcgaagg caatgccggc     300

atcgacgccg cctacgatat gcgcggcgaa agcattttcc tgcgcggctt tcaagccgac     360

gcatctgata tttaccgcga cggcgtacgc gaaagcgggc aggtgcgccg tagcaccgcc     420

aacatcgagc gcgtggaaat cctgaaaggt ccgtcctccg tgctttatgg gcgtaccaac     480

ggcggcggtg tcatcaacat ggtcagcaaa tacgccaact tcaaacaaag ccgtaatatc     540

ggtacggttt atggttcgtg ggcaaaccgc agcctgaata tggacatcaa cgaagtgctg     600

aacaaaaacg tcgccatccg tctcaccggc gaagtcgggc gcgccaattc gttccgcagc     660

ggcatagaca gcaaaaatgt catggtttcg cccagcatta ccgtcaaact cgacaacggc     720

ttgaagtgga cggggcaata cacctacgac aatgtggagc gcacgcccga ccgcagtccg     780

accaagtccg tgtacgaccg cttcggactg ccttaccgca tggggttcgc ccaccggaac     840

gattttgtca aagacaagct gcaagtttgg cgttccgacc ttgaatacgc cttcaacgac     900
```

-continued

```
aaatggcgtg cccaatggca gctcgcccac cgcacggcgg cgcaggattt tgatcatttc    960

tatgcaggca gcgaaaatgg caacttaatc aaacgtaact acgcctggca gcagaccgac   1020

aacaaaaccc tgtcgtccaa cttaacgctc aacggcgact acaccatcgg ccgttttgaa   1080

aaccacctga ccgtaggcat ggattacagc cgcgaacacc gcaacccgac attgggtttc   1140

agcagcgcct tttccgcctc catcaacccc tacgaccgcg caagctggcc ggcttcgggc   1200

agattgcagc ctattctgac ccaaaaccgc cacaaagccg actcctacgg catctttgtg   1260

caaaacatct tctccgccac gcccgatttg aaattcgtcc tcggcggccg ttacgacaaa   1320

tacaccttta attccgaaaa caaactcacc ggcagcagcc gccaatacag cggacactcg   1380

ttcagcccca acatcggcgc agtgtggaac atcaatcccg tccacacact ttacgcctcg   1440

tataacaaag gcttcgcgcc ttatggcgga cgcggcggct atttgagcat cgatacgttg   1500

tcttccgccg tgttcaacgc cgaccccgag tacacccgcc aatacgaaac cggcgtgaaa   1560

agcagttggc tggacgaccg cctcagcact acgttgtctg cctaccaaat cgaacgcttc   1620

aatatccgct accgccccga tccaaaaaac aacccttata tttatgcggt tagcggcaaa   1680

caccgttcgc gcggcgtgga attgtccgcc atcgggcaaa tcatccccaa aaaactctat   1740

ctgcgcggtt cgttgggcgt gatgcaggcg aaagtcgttg aagacaaaga aaatcccgac   1800

cgagtgggca tccatttgaa taacaccagc aacgttaccg gcaacctgtt tttccgttat   1860

accccgaccg aaaacctcta cggcgaaatc ggcgtaaccg gtacaggcaa acgctacggt   1920

tacgactcaa gaaataaaga agtgactacg cttccaggct ttgcccgagt tgatgccatg   1980

cttggctgga accataaaaa tgttaacgtt acctttgccg cagccaatct gttcaatcaa   2040

aaatattggc gttcggactc tatgccgggt aatccgcgcg gctatactgc ccgggtaaat   2100

taccgtttct ga                                                       2112


<210> SEQ ID NO 30
<211> LENGTH: 703
<212> TYPE: PRT
<213> ORGANISM: Neisseria meningitidis

<400> SEQUENCE: 30

Met Lys Ile Ser Phe His Leu Ala Leu Leu Pro Thr Leu Ile Ile Ala
1               5                   10                  15

Ser Phe Pro Val Ala Ala Ala Asp Thr Gln Asp Asn Gly Glu His Tyr
            20                  25                  30

Thr Ala Thr Leu Pro Thr Val Ser Val Val Gly Gln Ser Asp Thr Ser
        35                  40                  45

Val Leu Lys Gly Tyr Ile Asn Tyr Asp Glu Ala Ala Val Thr Arg Asn
    50                  55                  60

Gly Gln Leu Ile Lys Glu Thr Pro Gln Thr Ile Asp Thr Leu Asn Ile
65                  70                  75                  80

Gln Lys Asn Lys Asn Tyr Gly Thr Asn Asp Leu Ser Ser Ile Leu Glu
                85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
```

-continued

```
145                 150                 155                 160

Gly Gly Gly Val Ile Asn Met Val Ser Lys Tyr Ala Asn Phe Lys Gln
                165                 170                 175

Ser Arg Asn Ile Gly Thr Val Tyr Gly Ser Trp Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
    210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
            260                 265                 270

Arg Met Gly Phe Ala His Arg Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300

Gln Trp Gln Leu Ala His Arg Thr Ala Ala Gln Asp Phe Asp His Phe
305                 310                 315                 320

Tyr Ala Gly Ser Glu Asn Gly Asn Leu Ile Lys Arg Asn Tyr Ala Trp
                325                 330                 335

Gln Gln Thr Asp Asn Lys Thr Leu Ser Ser Asn Leu Thr Leu Asn Gly
            340                 345                 350

Asp Tyr Thr Ile Gly Arg Phe Glu Asn His Leu Thr Val Gly Met Asp
        355                 360                 365

Tyr Ser Arg Glu His Arg Asn Pro Thr Leu Gly Phe Ser Ser Ala Phe
    370                 375                 380

Ser Ala Ser Ile Asn Pro Tyr Asp Arg Ala Ser Trp Pro Ala Ser Gly
385                 390                 395                 400

Arg Leu Gln Pro Ile Leu Thr Gln Asn Arg His Lys Ala Asp Ser Tyr
                405                 410                 415

Gly Ile Phe Val Gln Asn Ile Phe Ser Ala Thr Pro Asp Leu Lys Phe
            420                 425                 430

Val Leu Gly Gly Arg Tyr Asp Lys Tyr Thr Phe Asn Ser Glu Asn Lys
        435                 440                 445

Leu Thr Gly Ser Ser Arg Gln Tyr Ser Gly His Ser Phe Ser Pro Asn
    450                 455                 460

Ile Gly Ala Val Trp Asn Ile Asn Pro Val His Thr Leu Tyr Ala Ser
465                 470                 475                 480

Tyr Asn Lys Gly Phe Ala Pro Tyr Gly Gly Arg Gly Gly Tyr Leu Ser
                485                 490                 495

Ile Asp Thr Leu Ser Ser Ala Val Phe Asn Ala Asp Pro Glu Tyr Thr
            500                 505                 510

Arg Gln Tyr Glu Thr Gly Val Lys Ser Ser Trp Leu Asp Asp Arg Leu
        515                 520                 525

Ser Thr Thr Leu Ser Ala Tyr Gln Ile Glu Arg Phe Asn Ile Arg Tyr
    530                 535                 540

Arg Pro Asp Pro Lys Asn Asn Pro Tyr Ile Tyr Ala Val Ser Gly Lys
545                 550                 555                 560

His Arg Ser Arg Gly Val Glu Leu Ser Ala Ile Gly Gln Ile Ile Pro
                565                 570                 575
```

-continued

```
Lys Lys Leu Tyr Leu Arg Gly Ser Leu Gly Val Met Gln Ala Lys Val
            580                 585                 590

Val Glu Asp Lys Glu Asn Pro Asp Arg Val Gly Ile His Leu Asn Asn
        595                 600                 605

Thr Ser Asn Val Thr Gly Asn Leu Phe Phe Arg Tyr Thr Pro Thr Glu
    610                 615                 620

Asn Leu Tyr Gly Glu Ile Gly Val Thr Gly Thr Gly Lys Arg Tyr Gly
625                 630                 635                 640

Tyr Asp Ser Arg Asn Lys Glu Val Thr Thr Leu Pro Gly Phe Ala Arg
                645                 650                 655

Val Asp Ala Met Leu Gly Trp Asn His Lys Asn Val Asn Val Thr Phe
            660                 665                 670

Ala Ala Ala Asn Leu Phe Asn Gln Lys Tyr Trp Arg Ser Asp Ser Met
        675                 680                 685

Pro Gly Asn Pro Arg Gly Tyr Thr Ala Arg Val Asn Tyr Arg Phe
    690                 695                 700
```

<210> SEQ ID NO 31
<211> LENGTH: 2113
<212> TYPE: DNA
<213> ORGANISM: Neisseria meningitidis

<400> SEQUENCE: 31

```
atgaaaatat catttcattt agctttatta cccacgctga ttattgcttc cttccctgtt     60

gctgccgccg atacgcagga caatggtgaa cattacaccg ccactctgcc caccgtttcc    120

gtggtcggac agtccgacac cagcgtactc aaaggctaca tcaactacga cgaagccgcc    180

gttacccgca acggacagct catcaaagaa acgccgcaaa ccatcgatac gctcaatatc    240

cagaaaaaca aaaattacgg cacgaacgat ttgagttcca tcctcgaagg caatgccggc    300

atcgacgccg cctacgatat gcgcggcgaa agcattttcc tgcgcggctt tcaagccgac    360

gcatctgata tttaccgcga cggcgtacgc gaaagcgggc aggtgcgccg tagcaccgcc    420

aacatcgagc gcgtggaaat cctgaaaggt ccgtcctccg tgctttatgg gcgtaccaac    480

ggcggcggtg tcatcaacat ggtcagcaaa tacgccaact tcaaacaaag ccgtaatatc    540

ggtacggttt atggttcgtg ggcaaaccgc agcctgaata tggacatcaa cgaagtgctg    600

aacaaaaacg tcgccatccg tctcaccggc gaagtcgggc gcgccaattc gttccgcagc    660

ggcatagaca gcaaaaatgt catggtttcg cccagcatta ccgtcaaact cgacaacggc    720

ttgaagtgga cggggcaata cacctacgac aatgtggagc gcacgcccga ccgcagtccg    780

accaagtccg tgtacgaccg cttcggactg ccttaccgca tggggttcgc ccaccggaac    840

gattttgtca aagacaagct gcaagtttgg cgttccgacc ttgaatacgc cttcaacgac    900

aaatggcgtg cccaatggca gctcgcccac cgcacggcgg cgcaggattt tgatcatttc    960

tatgcaggca gcgaaaatgg caacttaatc aaacgtaact acgcctggca gcagaccgac   1020

aacaaaaccc tgtcgtccaa cttaacgctc aacggcgact acaccatcgg ccgttttgaa   1080

aaccacctga ccgtaggcat ggattacagc cgcgaacacc gcaacccgac attgggtttc   1140

agcagcgcct tttccgcctc catcaacccc tacgaccgcg caagctggcc ggcttcgggc   1200

agattgcagc ctattctgac ccaaaaccgc cacaaagccg actcctacgg catctttgtg   1260

caaaacatct tctccgccac gcccgatttg aaattcgtcc tcggcggccg ttacgacaaa   1320

tacaccttta attccgaaaa caaactcacc ggcagcagcc gccaatacag cggacactcg   1380
```

-continued

```
ttcagcccca acatcggcgc agtgtggaac atcaatcccg tccacacact ttacgcctcg   1440

tataacaaag gcttcgcgcc ttatggcgga cgcggcggct atttgagcat cgatacgttg   1500

tcttccgccg tgttcaacgc cgaccccgag tacacccgcc aatacgaaac cggcgtgaaa   1560

agcagttggc tggacgaccg cctcagcact acgttgtctg cctaccaaat cgaacgcttc   1620

aatatccgct accgccccga tccaaaaaac aacccttata tttatgcggt tagcggcaaa   1680

caccgttcgc gcggcgtgga attgtccgcc atcgggcaaa tcatccccaa aaaaactcta   1740

tctgcgcggt tcgttgggcg tgatgcaggc gaaagtcgtt gaagacaaag aaaatcccga   1800

ccgagtgggc atccatttga ataacaccag caacgttacc ggcaacctgt ttttccgtta   1860

taccccgacc gaaaacctct acggcgaaat cggcgtaacc ggtacaggca aacgctacgg   1920

ttacgactca agaaataaag aagtgactac gcttccaggc tttgcccgag ttgatgccat   1980

gcttggctgg aaccataaaa atgttaacgt tacctttgcc gcagccaatc tgttcaatca   2040

aaaatattgg cgttcggact ctatgccggg taatccgcgc ggctatactg cccgggtaaa   2100

ttaccgtttc tga                                                       2113


<210> SEQ ID NO 32
<211> LENGTH: 697
<212> TYPE: PRT
<213> ORGANISM: Neisseria meningitidis

<400> SEQUENCE: 32

Met Lys Ile Ser Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30

Thr Ala Thr Leu Pro Thr Val Ser Val Val Gly Gln Ser Asp Thr Ser
         35                  40                  45

Val Leu Lys Gly Tyr Ile Asn Tyr Asp Glu Ala Ala Val Thr Arg Asn
     50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                 85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Thr Val Tyr Gly Ser Trp Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
    210                 215                 220

Lys Asn Val Met Val Ser Pro Ser Ile Thr Val Lys Leu Asp Asn Gly
225                 230                 235                 240
```

-continued

```
Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
            260                 265                 270

Arg Met Gly Phe Ala His Arg Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300

Gln Trp Gln Leu Ala His Arg Thr Ala Ala Gln Asp Phe Asp His Phe
305                 310                 315                 320

Tyr Ala Gly Ser Glu Asn Gly Asn Leu Ile Lys Arg Asn Tyr Ala Trp
                325                 330                 335

Gln Gln Thr Asp Asn Lys Thr Leu Ser Ser Asn Leu Thr Leu Asn Gly
            340                 345                 350

Asp Tyr Thr Ile Gly Arg Phe Glu Asn His Leu Thr Val Gly Met Asp
        355                 360                 365

Tyr Ser Arg Glu His Arg Asn Pro Thr Leu Gly Phe Ser Ser Ala Phe
    370                 375                 380

Ser Ala Ser Ile Asn Pro Tyr Asp Arg Ala Ser Trp Pro Ala Ser Gly
385                 390                 395                 400

Arg Leu Gln Pro Ile Leu Thr Gln Asn Arg His Lys Ala Asp Ser Tyr
                405                 410                 415

Gly Ile Phe Val Gln Asn Ile Phe Ser Ala Thr Pro Asp Leu Lys Phe
            420                 425                 430

Val Leu Gly Gly Arg Tyr Asp Lys Tyr Thr Phe Asn Ser Glu Asn Lys
        435                 440                 445

Leu Thr Gly Ser Ser Arg Gln Tyr Ser Gly His Ser Phe Ser Pro Asn
    450                 455                 460

Ile Gly Ala Val Trp Asn Ile Asn Pro Val His Thr Leu Tyr Ala Ser
465                 470                 475                 480

Tyr Asn Lys Gly Phe Ala Pro Tyr Gly Gly Arg Gly Gly Tyr Leu Ser
                485                 490                 495

Ile Asp Thr Leu Ser Ser Ala Val Phe Asn Ala Asp Pro Glu Tyr Thr
            500                 505                 510

Arg Gln Tyr Glu Thr Gly Val Lys Ser Ser Trp Leu Asp Asp Arg Leu
        515                 520                 525

Ser Thr Thr Leu Ser Ala Tyr Gln Ile Glu Arg Phe Asn Ile Arg Tyr
    530                 535                 540

Arg Pro Asp Pro Lys Asn Asn Pro Tyr Ile Tyr Ala Val Ser Gly Lys
545                 550                 555                 560

His Arg Ser Arg Gly Val Glu Leu Ser Ala Ile Gly Gln Ile Ile Pro
                565                 570                 575

Lys Lys Thr Leu Ser Ala Arg Phe Val Gly Arg Asp Ala Gly Glu Ser
            580                 585                 590

Arg Arg Gln Arg Lys Ser Arg Pro Ser Gly His Pro Phe Glu His Gln
        595                 600                 605

Gln Arg Tyr Arg Gln Pro Val Phe Pro Leu Tyr Pro Asp Arg Lys Pro
    610                 615                 620

Leu Arg Arg Asn Arg Arg Asn Arg Tyr Arg Gln Thr Leu Arg Leu Arg
625                 630                 635                 640

Leu Lys Lys Arg Ser Asp Tyr Ala Ser Arg Leu Cys Pro Ser Cys His
                645                 650                 655

Ala Trp Leu Glu Pro Lys Cys Arg Tyr Leu Cys Arg Ser Gln Ser Val
```

-continued

```
            660                 665                 670

Gln Ser Lys Ile Leu Ala Phe Gly Leu Tyr Ala Gly Ser Ala Arg Leu
        675                 680                 685

Tyr Cys Pro Gly Lys Leu Pro Phe Leu
    690                 695


<210> SEQ ID NO 33
<211> LENGTH: 2111
<212> TYPE: DNA
<213> ORGANISM: Neisseria meningitidis

<400> SEQUENCE: 33

atgaaaatat catttcattt agctttatta cccacgctga ttattgcttc cttccctgtt     60

gctgccgccg atacgcagga caatggtgaa cattacaccg ccactctgcc caccgtttcc    120

gtggtcggac agtccgacac cagcgtactc aaaggctaca tcaactacga cgaagccgcc    180

gttacccgca acggacagct catcaaagaa acgccgcaaa ccatcgatac gctcaatatc    240

cagaaaaaca aaaattacgg tacgaacgat ttgagttcca tcctcgaagg caatgccggc    300

atcgacgctg cctacgatat gcgcggcgaa agcattttcc tgcgcggttt tcaagccgac    360

gcatccgata tttaccgcga cggcgtgcgc gaaagcggac aagtgcgccg cagtactgcc    420

aacatcgagc gcgtggaaat tctgaaaggc ccgtcttccg tgctttacgg ccgcaccaac    480

ggcggtggcg tcatcaacat ggtcagcaaa tacgccaact tcaaacaaag ccgcaacatc    540

ggagcggttt acggctcaag ggcaaaccgc agcctgaata tggacattaa cgaagtgctg    600

aacaaaaacg tcgccatccg tctcaccggc gaagtcgggc gcgccaattc gttccgcagc    660

ggcatagaca gcaaaaatgt catggtttcg cccagcatta ccgtcaaact cgacaacggc    720

ttgaagtgga cggggcaata cacctacgac aatgtggagc gcacgcccga ccgcagtccg    780

accaagtccg tgtacgaccg cttcggactg ccttaccgca tggggttcgc ccaccggaac    840

gattttgtca aagacaagct gcaagtttgg cgttccgacc ttgaatacgc cttcaacgac    900

aaatggcgtg cccaatggca gctcgcccac cgcacggcgg cgcaggattt tgatcatttc    960

tatgcaggca gcgaaaatgg caacttaatc aaacgtaact acgcctggca gcagaccgac   1020

aacaaaaccc tgtcgtccaa tttcacgctc aacggcgact acaccatcgg ccgttttgaa   1080

aaccacttga ccgtaggcat ggattacagc cgcgaacacc gcaacccgac cttaggttac   1140

agccgcgcct ttactgcttc catcgatcca tacgaccgag caagctggcc ggcttcgggc   1200

agattgcagc ctatcctcac ccaaaaccgc cacaaagccg actcctacgg catctttgtg   1260

caaaacatct tctccgccac gcccgatttg aaattcgtcc tcggcggccg ttacgacaaa   1320

tacaccttta attccgaaaa caaactcacc ggcagcagcc gccagtacag cggccactcg   1380

ttcagcccca acatcggcgc agtgtggaac atcaaccccg ttcacacact ttacgcctcg   1440

tataacaaag gtttcgcgcc ttatggcgga cgcggcggct atttgagcat cgatacgtca   1500

tcttctgccg tgtttaacgc cgaccccgag tacacccgcc aatacgaaac cggcgtcaaa   1560

agcagttggc tggacaatcg tttggacacc acattgtccg cctaccaaat cgaacgcttc   1620

aatatccgct accgccccga cgcggaaaat aatccctaca cttgggcagt cggcggcaaa   1680

caccgttcgc gtggcgtgga attgtccgcc atcgggcaaa tcatccccaa aaaactctat   1740

ctgcgcggtt cgttgggcgt gatgcaggcg aaagtcgttg aagacaaaaa aaatcccgac   1800

cgagtgggca tccatttgaa taataccagc aacgttaccg gcaacctgtt tttccgttat   1860

acccgaccga aaacctctac ggcgaaatcg gcgtaaccgg tacaggcaaa cgctacggtt   1920
```

-continued

```
acaactcaag aaataaagaa gtgactacgc ttccaggctt tgcccgagtt gatgccatgc   1980

ttggctggaa ccataaaaat gttaacgtta cctttgccgc agccaatctg ttcaatcaaa   2040

aatattggcg ttcggactct atgccgggta atccgcgcgg ctatactgcc cgggtaaatt   2100

accgtttctg a                                                        2111


<210> SEQ ID NO 34
<211> LENGTH: 700
<212> TYPE: PRT
<213> ORGANISM: Neisseria meningitidis

<400> SEQUENCE: 34

Met Lys Ile Ser Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30

Thr Ala Thr Leu Pro Thr Val Ser Val Val Gly Gln Ser Asp Thr Ser
         35                  40                  45

Val Leu Lys Gly Tyr Ile Asn Tyr Asp Glu Ala Ala Val Thr Arg Asn
     50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                 85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Ala Val Tyr Gly Ser Arg Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
    210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
            260                 265                 270

Arg Met Gly Phe Ala His Arg Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300

Gln Trp Gln Leu Ala His Arg Thr Ala Ala Gln Asp Phe Asp His Phe
305                 310                 315                 320

Tyr Ala Gly Ser Glu Asn Gly Asn Leu Ile Lys Arg Asn Tyr Ala Trp
                325                 330                 335
```

-continued

```
Gln Gln Thr Asp Asn Lys Thr Leu Ser Ser Asn Phe Thr Leu Asn Gly
            340                 345                 350

Asp Tyr Thr Ile Gly Arg Phe Glu Asn His Leu Thr Val Gly Met Asp
        355                 360                 365

Tyr Ser Arg Glu His Arg Asn Pro Thr Leu Gly Tyr Ser Arg Ala Phe
    370                 375                 380

Thr Ala Ser Ile Asp Pro Tyr Asp Arg Ala Ser Trp Pro Ala Ser Gly
385                 390                 395                 400

Arg Leu Gln Pro Ile Leu Thr Gln Asn Arg His Lys Ala Asp Ser Tyr
                405                 410                 415

Gly Ile Phe Val Gln Asn Ile Phe Ser Ala Thr Pro Asp Leu Lys Phe
            420                 425                 430

Val Leu Gly Gly Arg Tyr Asp Lys Tyr Thr Phe Asn Ser Glu Asn Lys
        435                 440                 445

Leu Thr Gly Ser Ser Arg Gln Tyr Ser Gly His Ser Phe Ser Pro Asn
    450                 455                 460

Ile Gly Ala Val Trp Asn Ile Asn Pro Val His Thr Leu Tyr Ala Ser
465                 470                 475                 480

Tyr Asn Lys Gly Phe Ala Pro Tyr Gly Gly Arg Gly Gly Tyr Leu Ser
                485                 490                 495

Ile Asp Thr Ser Ser Ser Ala Val Phe Asn Ala Asp Pro Glu Tyr Thr
            500                 505                 510

Arg Gln Tyr Glu Thr Gly Val Lys Ser Ser Trp Leu Asp Asn Arg Leu
        515                 520                 525

Asp Thr Thr Leu Ser Ala Tyr Gln Ile Glu Arg Phe Asn Ile Arg Tyr
    530                 535                 540

Arg Pro Asp Ala Glu Asn Asn Pro Tyr Thr Trp Ala Val Gly Gly Lys
545                 550                 555                 560

His Arg Ser Arg Gly Val Glu Leu Ser Ala Ile Gly Gln Ile Ile Pro
                565                 570                 575

Lys Lys Leu Tyr Leu Arg Gly Ser Leu Gly Val Met Gln Ala Lys Val
            580                 585                 590

Val Glu Asp Lys Lys Asn Pro Asp Arg Val Gly Ile His Leu Asn Asn
        595                 600                 605

Thr Ser Asn Val Thr Gly Asn Leu Phe Phe Arg Tyr Thr Arg Pro Lys
    610                 615                 620

Thr Ser Thr Ala Lys Ser Ala Pro Val Gln Ala Asn Ala Thr Val Thr
625                 630                 635                 640

Thr Gln Glu Ile Lys Lys Leu Arg Phe Gln Ala Leu Pro Glu Leu Met
                645                 650                 655

Pro Cys Leu Ala Gly Thr Ile Lys Met Leu Thr Leu Pro Leu Pro Gln
            660                 665                 670

Pro Ile Cys Ser Ile Lys Asn Ile Gly Val Arg Thr Leu Cys Arg Val
        675                 680                 685

Ile Arg Ala Ala Ile Leu Pro Gly Ile Thr Val Ser
    690                 695                 700
```

<210> SEQ ID NO 35
<211> LENGTH: 2112
<212> TYPE: DNA
<213> ORGANISM: Neisseria meningitidis

<400> SEQUENCE: 35

```
atgaaaatat catttcattt agctttatta cccacgctga ttattgcttc cttccctgtt      60
```

-continued

```
gctgccgccg atacgcagga caatggtgaa cattacaccg ccactctgcc caccgtttcc    120

gtggtcggac agtccgacac cagcgtactc aaaggctaca tcaactacga cgaagccgcc    180

gttacccgca acggacagct catcaaagaa acgccgcaaa ccatcgatac gctcaatatc    240

cagaaaaaca aaaattacgg tacgaacgat ttgagttcca tcctcgaagg caatgccggc    300

atcgacgctg cctacgatat gcgcggcgaa agcattttcc tgcgcggttt tcaagccgac    360

gcatccgata tttaccgcga cggcgtgcgc gaaagcggac aagtgcgccg cagtactgcc    420

aacatcgagc gcgtggaaat cctgaaaggc ccgtcttccg tgctttacgg ccgcaccaac    480

ggcggcggcg tcatcaacat ggtcagcaaa tacgccaact tcaaacaaag ccgcaacatc    540

ggagcggttt acggctcatg ggcaaaccgc agcctgaata tggacattaa cgaagtgctg    600

aacaaaaacg tcgccatccg tctcaccggc gaagtcgggc gcgccaattc gttccgcagc    660

ggcatagaca gcaaaaatgt catggtttcg cccagcatta ccgtcaaact cgacaacggc    720

ttgaagtgga cggggcaata cacctacgac aatgtggagc gcacgcccga ccgcagtccg    780

accaagtccg tgtacgaccg cttcggactg ccttaccgca tggggttcgc ccaccggaac    840

gattttgtca aagacaagct gcaagtttgg cgttccgacc ttgaatacgc cttcaacgac    900

aaatggcgtg cccaatggca gctcgcccac cgcacggcgg cgcaggattt tgatcatttc    960

tatgcaggca gcgaaaatgg caacttaatc aaacgtaact acgcctggca gcagaccgac   1020

aacaaaaccc tgtcgtccaa cttaacgctc aacggcgact acaccatcgg ccgttttgaa   1080

aaccacctga ccgtaggcat ggattacagc cgcgaacacc gcaacccgac attgggtttc   1140

agcagcgcct tttccgcctc catcaacccc tacgaccgcg caagctggcc ggcttcgggc   1200

agattgcagc ctattctgac ccaaaaccgc cacaaagccg acgcctacgg catctttgtg   1260

caaaacatct tctccgccac gcccgatttg aaattcgtcc tcggcggtcg ttacgacaaa   1320

tacaccttta attccgaaaa caaactcacc ggcagcagcc gccaatacag cggacactcg   1380

ttcagcccca acatcggcgc agtgtggaac atcaatcccg tccacacact ttacgcctcg   1440

tataataaag gcttcgcgcc ttatggcgga cgcggcggct atttgagcat caacacgtcg   1500

tcttccgccg tgttcaacgc cgaccccgag tacacccgcc aatacgaaac cggtgtgaaa   1560

agcagttggc tggacgaccg cctcagcact acgttgtctg cctaccaaat cgaacgcttc   1620

aatatccgct accgccccga cgagcaaaat gatccctaca cttgggcagt cggcggcaaa   1680

caccgttcgc gcggcgtgga attgtccgcc atcgggcaaa tcatccccaa aaaactctat   1740

ctgcgcggtt cgttgggcgt gatgcaggcg aaagtcgttg aagacaaaga aaatcccgac   1800

cgagtgggca tccatttgaa taacaccagc aacgttaccg gcaacctgtt tttccgttat   1860

accccgaccg aaaacctcta cggcgaaatc ggcgtaaccg gtacaggcaa acgctacggt   1920

tacaactcaa gaaataaaga agtgactacg cttccaggct ttgcccgagt tgatgccatg   1980

cttggctgga accataaaaa tgttaacatt acctttgccg cagccaatct gctcaatcaa   2040

aaatattggc gttcggatgc catgcccggc gcgccgcgca cttatacggc gcgggttaat   2100

tacagtttct aa                                                       2112
```

<210> SEQ ID NO 36
<211> LENGTH: 703
<212> TYPE: PRT
<213> ORGANISM: Neisseria meningitidis

<400> SEQUENCE: 36

-continued

```
Met Lys Ile Ser Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30

Thr Ala Thr Leu Pro Thr Val Ser Val Val Gly Gln Ser Asp Thr Ser
         35                  40                  45

Val Leu Lys Gly Tyr Ile Asn Tyr Asp Glu Ala Ala Val Thr Arg Asn
     50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                 85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Ala Val Tyr Gly Ser Trp Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
    210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
            260                 265                 270

Arg Met Gly Phe Ala His Arg Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300

Gln Trp Gln Leu Ala His Arg Thr Ala Ala Gln Asp Phe Asp His Phe
305                 310                 315                 320

Tyr Ala Gly Ser Glu Asn Gly Asn Leu Ile Lys Arg Asn Tyr Ala Trp
                325                 330                 335

Gln Gln Thr Asp Asn Lys Thr Leu Ser Ser Asn Leu Thr Leu Asn Gly
            340                 345                 350

Asp Tyr Thr Ile Gly Arg Phe Glu Asn His Leu Thr Val Gly Met Asp
        355                 360                 365

Tyr Ser Arg Glu His Arg Asn Pro Thr Leu Gly Phe Ser Ser Ala Phe
    370                 375                 380

Ser Ala Ser Ile Asn Pro Tyr Asp Arg Ala Ser Trp Pro Ala Ser Gly
385                 390                 395                 400

Arg Leu Gln Pro Ile Leu Thr Gln Asn Arg His Lys Ala Asp Ala Tyr
                405                 410                 415

Gly Ile Phe Val Gln Asn Ile Phe Ser Ala Thr Pro Asp Leu Lys Phe
```

-continued

```
            420                 425                 430

Val Leu Gly Gly Arg Tyr Asp Lys Tyr Thr Phe Asn Ser Glu Asn Lys
        435                 440                 445

Leu Thr Gly Ser Ser Arg Gln Tyr Ser Gly His Ser Phe Ser Pro Asn
    450                 455                 460

Ile Gly Ala Val Trp Asn Ile Asn Pro Val His Thr Leu Tyr Ala Ser
465                 470                 475                 480

Tyr Asn Lys Gly Phe Ala Pro Tyr Gly Gly Arg Gly Gly Tyr Leu Ser
                485                 490                 495

Ile Asn Thr Ser Ser Ser Ala Val Phe Asn Ala Asp Pro Glu Tyr Thr
            500                 505                 510

Arg Gln Tyr Glu Thr Gly Val Lys Ser Ser Trp Leu Asp Asp Arg Leu
        515                 520                 525

Ser Thr Thr Leu Ser Ala Tyr Gln Ile Glu Arg Phe Asn Ile Arg Tyr
    530                 535                 540

Arg Pro Asp Glu Gln Asn Asp Pro Tyr Thr Trp Ala Val Gly Gly Lys
545                 550                 555                 560

His Arg Ser Arg Gly Val Glu Leu Ser Ala Ile Gly Gln Ile Ile Pro
                565                 570                 575

Lys Lys Leu Tyr Leu Arg Gly Ser Leu Gly Val Met Gln Ala Lys Val
            580                 585                 590

Val Glu Asp Lys Glu Asn Pro Asp Arg Val Gly Ile His Leu Asn Asn
        595                 600                 605

Thr Ser Asn Val Thr Gly Asn Leu Phe Phe Arg Tyr Thr Pro Thr Glu
    610                 615                 620

Asn Leu Tyr Gly Glu Ile Gly Val Thr Gly Thr Gly Lys Arg Tyr Gly
625                 630                 635                 640

Tyr Asn Ser Arg Asn Lys Glu Val Thr Thr Leu Pro Gly Phe Ala Arg
                645                 650                 655

Val Asp Ala Met Leu Gly Trp Asn His Lys Asn Val Asn Ile Thr Phe
            660                 665                 670

Ala Ala Ala Asn Leu Leu Asn Gln Lys Tyr Trp Arg Ser Asp Ala Met
        675                 680                 685

Pro Gly Ala Pro Arg Thr Tyr Thr Ala Arg Val Asn Tyr Ser Phe
    690                 695                 700


<210> SEQ ID NO 37
<211> LENGTH: 2112
<212> TYPE: DNA
<213> ORGANISM: Neisseria meningitidis

<400> SEQUENCE: 37

atgaaaatat catttcattt agctttatta cccacgctga ttattgcttc cttccctgtt      60

gctgccgccg atacgcagga caatggtgaa cattacaccg ccactctgcc caccgtttcc     120

gtggtcggac agtccgacac cagcgtactc aaaggctaca tcaactacga cgaagccgcc     180

gttacccgca acggacagct catcaaagaa acgccgcaaa ccatcgatac gctcaatatc     240

tagaaaaaca aaaattacgg tacgaacgat ttgagttcca tcctcgaagg caatgccggc     300

atcgacgctg cctacgatat gcgcggcgaa agcattttcc tgcgcggttt tcaagccgac     360

gcatccgata tttaccgcga cggcgtgcgc gaaagcggac aagtgcgccg cagtactgcc     420

aacatcgagc gcgtggaaat cctgaaaggc ccgtcttccg tgctttacgg ccgcaccaac     480

ggcggcggcg tcatcaacat ggtcagcaaa tacgccaact tcaaacaaag ccgcaacatc     540
```

-continued

```
ggtgcggttt acggttcgtg ggcaaaccgc agcctgaata tggacattaa cgaagtgttg    600

aacaaaaacg tcgccatccg tctcaccggc gaagtcgggc gcgccaattc gttccgcagc    660

ggcatagaca gcaaaaatgt catggtttcg cccagcatta ccgtcaaact cgacaacggc    720

ttgaagtgga cggggcaata cacctacgac aatgtggagc gcacgcccga ccgcagtccg    780

accaagtccg tgtacgaccg cttcggactg ccttaccgca tggggttcgc ccaccggaac    840

gattttgtca aagacaagct gcaagtttgg cgctccgacc ttgaatacgc cttcaacgac    900

aaatggcgtg cccaatggca gctcgcccac cgcacggcgg cgcaggattt tgatcatttc    960

tatgcaggca gcgaaaatgg caacttaatc aaacgtaact acgcctggca gcagaccgac   1020

aacaaaaccc tgtcgtccaa tttcacgcta aacggcgact acaccatcgg ccgttttgaa   1080

aaccacttga ccgtaggcat ggattacagc cgcgaacacc gcaaccccgac cttaggttac   1140

agccgcgcct ttactgcttc catcgatcca tacgaccgag caagctggcc ggcttcgggc   1200

agattgcagc ctatcctcac ccaaaaccgc cacaaagccg actcctacgg catctttgtg   1260

caaaacatct tctccgccac gcccgatttg aaattcgtcc tcggcggtcg ttacgacaaa   1320

tacaccttta attccgaaaa caaactcacc ggcagcagcc gccaatacag cggacactcg   1380

ttcagcccca acatcggcgc agtgtggaac atcaatcccg tccacacact ttacgcctcg   1440

tataataaag gcttcgcgcc ttatggcgga cgcggcggct atttgagcat caacacgtcg   1500

tcttccgccg tgttcaacgc cgaccccgag tacacccgcc aatacgaaac cggtgtgaaa   1560

agcagttggc tggacgaccg cctcagcact acgttgtctg cctaccaaat cgaacgcttc   1620

aatatccgct accgccccga cgagcaaaat gatccctaca cttgggcagt cggcggcaaa   1680

caccgttcgc gcggcgtgga attgtccgcc atcgggcaaa tcatccccaa aaaactctat   1740

ctgcgcggtt cgttgggcgt gatgcaggcg aaagtcgttg aagacaaaga aaatcccgac   1800

cgagtgggca tccatttgaa taacaccagc aacgttaccg gcaacctgtt tttccgttat   1860

accccgaccg aaaacctcta cggcgaaatc ggcgtaaccg gtacaggcaa acgctacggt   1920

tacaactcaa gaaataaaga agtgactacg cttccaggct ttgcccgagt tgatgccatg   1980

cttggctgga accataaaaa tgttaacatt acctttgccg cagccaatct gctcaatcaa   2040

aaatattggc gttcggatgc catgcccggc gcgccgcgca cttatacggc gcgggttaat   2100

tacagtttct aa                                                       2112
```

<210> SEQ ID NO 38
<211> LENGTH: 702
<212> TYPE: PRT
<213> ORGANISM: Neisseria meningitidis

<400> SEQUENCE: 38

```
Met Lys Ile Ser Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30

Thr Ala Thr Leu Pro Thr Val Ser Val Val Gly Gln Ser Asp Thr Ser
         35                  40                  45

Val Leu Lys Gly Tyr Ile Asn Tyr Asp Glu Ala Ala Val Thr Arg Asn
     50                  55                  60

Gly Gln Leu Ile Lys Glu Thr Pro Gln Thr Ile Asp Thr Leu Asn Ile
 65                  70                  75                  80

Lys Asn Lys Asn Tyr Gly Thr Asn Asp Leu Ser Ser Ile Leu Glu Gly
                 85                  90                  95
```

-continued

```
Asn Ala Gly Ile Asp Ala Ala Tyr Asp Met Arg Gly Glu Ser Ile Phe
            100                 105                 110

Leu Arg Gly Phe Gln Ala Asp Ala Ser Asp Ile Tyr Arg Asp Gly Val
        115                 120                 125

Arg Glu Ser Gly Gln Val Arg Arg Ser Thr Ala Asn Ile Glu Arg Val
    130                 135                 140

Glu Ile Leu Lys Gly Pro Ser Ser Val Leu Tyr Gly Arg Thr Asn Gly
145                 150                 155                 160

Gly Gly Val Ile Asn Met Val Ser Lys Tyr Ala Asn Phe Lys Gln Ser
                165                 170                 175

Arg Asn Ile Gly Ala Val Tyr Gly Ser Trp Ala Asn Arg Ser Leu Asn
            180                 185                 190

Met Asp Ile Asn Glu Val Leu Asn Lys Asn Val Ala Ile Arg Leu Thr
        195                 200                 205

Gly Glu Val Gly Arg Ala Asn Ser Phe Arg Ser Gly Ile Asp Ser Lys
    210                 215                 220

Asn Val Met Val Ser Pro Ser Ile Thr Val Lys Leu Asp Asn Gly Leu
225                 230                 235                 240

Lys Trp Thr Gly Gln Tyr Thr Tyr Asp Asn Val Glu Arg Thr Pro Asp
                245                 250                 255

Arg Ser Pro Thr Lys Ser Val Tyr Asp Arg Phe Gly Leu Pro Tyr Arg
            260                 265                 270

Met Gly Phe Ala His Arg Asn Asp Phe Val Lys Asp Lys Leu Gln Val
        275                 280                 285

Trp Arg Ser Asp Leu Glu Tyr Ala Phe Asn Asp Lys Trp Arg Ala Gln
    290                 295                 300

Trp Gln Leu Ala His Arg Thr Ala Ala Gln Asp Phe Asp His Phe Tyr
305                 310                 315                 320

Ala Gly Ser Glu Asn Gly Asn Leu Ile Lys Arg Asn Tyr Ala Trp Gln
                325                 330                 335

Gln Thr Asp Asn Lys Thr Leu Ser Ser Asn Phe Thr Leu Asn Gly Asp
            340                 345                 350

Tyr Thr Ile Gly Arg Phe Glu Asn His Leu Thr Val Gly Met Asp Tyr
        355                 360                 365

Ser Arg Glu His Arg Asn Pro Thr Leu Gly Tyr Ser Arg Ala Phe Thr
    370                 375                 380

Ala Ser Ile Asp Pro Tyr Asp Arg Ala Ser Trp Pro Ala Ser Gly Arg
385                 390                 395                 400

Leu Gln Pro Ile Leu Thr Gln Asn Arg His Lys Ala Asp Ser Tyr Gly
                405                 410                 415

Ile Phe Val Gln Asn Ile Phe Ser Ala Thr Pro Asp Leu Lys Phe Val
            420                 425                 430

Leu Gly Gly Arg Tyr Asp Lys Tyr Thr Phe Asn Ser Glu Asn Lys Leu
        435                 440                 445

Thr Gly Ser Ser Arg Gln Tyr Ser Gly His Ser Phe Ser Pro Asn Ile
    450                 455                 460

Gly Ala Val Trp Asn Ile Asn Pro Val His Thr Leu Tyr Ala Ser Tyr
465                 470                 475                 480

Asn Lys Gly Phe Ala Pro Tyr Gly Gly Arg Gly Gly Tyr Leu Ser Ile
                485                 490                 495

Asn Thr Ser Ser Ser Ala Val Phe Asn Ala Asp Pro Glu Tyr Thr Arg
            500                 505                 510
```

-continued

```
Gln Tyr Glu Thr Gly Val Lys Ser Ser Trp Leu Asp Asp Arg Leu Ser
        515                 520                 525

Thr Thr Leu Ser Ala Tyr Gln Ile Glu Arg Phe Asn Ile Arg Tyr Arg
    530                 535                 540

Pro Asp Glu Gln Asn Asp Pro Tyr Thr Trp Ala Val Gly Gly Lys His
545                 550                 555                 560

Arg Ser Arg Gly Val Glu Leu Ser Ala Ile Gly Gln Ile Ile Pro Lys
                565                 570                 575

Lys Leu Tyr Leu Arg Gly Ser Leu Gly Val Met Gln Ala Lys Val Val
            580                 585                 590

Glu Asp Lys Glu Asn Pro Asp Arg Val Gly Ile His Leu Asn Asn Thr
        595                 600                 605

Ser Asn Val Thr Gly Asn Leu Phe Phe Arg Tyr Thr Pro Thr Glu Asn
    610                 615                 620

Leu Tyr Gly Glu Ile Gly Val Thr Gly Thr Gly Lys Arg Tyr Gly Tyr
625                 630                 635                 640

Asn Ser Arg Asn Lys Glu Val Thr Thr Leu Pro Gly Phe Ala Arg Val
                645                 650                 655

Asp Ala Met Leu Gly Trp Asn His Lys Asn Val Asn Ile Thr Phe Ala
            660                 665                 670

Ala Ala Asn Leu Leu Asn Gln Lys Tyr Trp Arg Ser Asp Ala Met Pro
        675                 680                 685

Gly Ala Pro Arg Thr Tyr Thr Ala Arg Val Asn Tyr Ser Phe
    690                 695                 700


<210> SEQ ID NO 39
<211> LENGTH: 2112
<212> TYPE: DNA
<213> ORGANISM: Neisseria meningitidis

<400> SEQUENCE: 39

atgaaaatat catttcattt agctttatta cccacgctga ttattgcttc cttccctgtt      60

gctgccgccg atacgcagga caatggtgaa cattacaccg ccactctgcc caccgtttcc     120

gtggtcggac agtccgacac cagcgtactc aaaggctaca tcaactacga cgaagccgcc     180

gttacccgca acggacagct catcaaagaa acgccgcaaa ccatcgatac gctcaatatc     240

tagaaaaaca aaaattacgg tacgaacgat ttgagttcca tcctcgaagg caatgccggc     300

atcgacgctg cctacgatat gcgcggcgaa agcattttcc tgcgcggttt tcaagccgac     360

gcatccgata tttaccgcga cggcgtgcgc gaaagcggac aagtgcgccg cagtactgcc     420

aacatcgagc gcgtggaaat cctgaaaggc ccgtcttccg tgctttacgg ccgcaccaac     480

ggcggcggcg tcatcaacat ggtcagcaaa tacgccaact tcaaacaaag ccgcaacatc     540

ggtgcggttt acggttcgtg ggcaaaccgc agcctgaata tggacattaa cgaagtgttg     600

aacaaaaacg tcgccatccg tctcaccggc gaagtcgggc gcgccaattc gttccgcagc     660

ggcatagaca gcaaaaatgt catggtttcg cccagcatta ccgtcaaact cgacaacggc     720

ttgaagtgga cggggcaata cacctacgac aatgtggagc gcacgcccga ccgcagtccg     780

accaagtccg tgtacgaccg cttcggactg ccttaccgca tggggttcgc ccaccggaac     840

gattttgtca aagacaagct gcaagtttgg cgctccgacc ttgaatacgc cttcaacgac     900

aaatggcgtg cccaatggca gctcgcccac cgcacggcgg cgcaggattt tgatcatttc     960

tatgcaggca gcgaaaatgg caacttaatc aaacgtaact acgcctggca gcagaccgac    1020

aacaaaaccc tgtcgtccaa tttcacgcta aacggcgact acaccatcgg ccgttttgaa    1080
```

-continued

```
aaccacttga ccgtaggcat ggattacagc cgcgaacacc gcaacccgac attgggctac   1140
cgcggcagtt tcaccgtgcc catcaacccc tacgaccgcg caagctggcc ggcttcgggc   1200
agattgcagc ctattctgac ccaaaaccgc cacaaagccg actcctacgg catctttgtg   1260
caaaacatct tctccgctac gcccgatttg aaattcgtcc tcggcggccg ttacgacaaa   1320
tacaccttta attccgaaaa caaactcacc ggcaacagcc gccaatacag cggacactcg   1380
ttcagcccca acatcggcgc agtgtggaac atcaacccag tccacacact ttacgcctcg   1440
tataacaaag gcttcgcgcc ttatggcgga cgcggcggct atttgagtat cgatacgttg   1500
tcttccgccg tgttcaacgc cgaccccgag tacacccgcc aatacgaaac cggcgtgaaa   1560
agcagttggc tggacgaccg cctcagcacc acattgtccg cctaccaaat cgaacgcttc   1620
aatatccgct accgccccga tccaaaaaac aacccttata tttatgcggt tagcggcaaa   1680
caccgttcgc gcggcgtgga attgtccgcc atcgggcaaa tcatccccaa aaaactctat   1740
ctgcgcggtt cgttgggcgt gatgcaggcg aaagtcgttg aagacaaaga aaatcccgac   1800
cgagtgggca tccatttgaa taataccagc aacgttaccg gcaacctgtt tttccgttat   1860
accccgaccg aaaacctcta cggcgaaatc ggcgtaaccg gtacaggcaa acgctacggt   1920
tacaactcaa gaaataaaga agtgactacg cttccaggct ttgcccgagt tgatgccatg   1980
cttggctgga accataaaaa tgttaacgtt acctttgccg cagccaatct gttcaatcaa   2040
aaatattggc gttcggactc tatgccgggt aatccgcgcg gctatactgc ccgggtaaat   2100
taccgtttct ga                                                       2112
```

```
<210> SEQ ID NO 40
<211> LENGTH: 702
<212> TYPE: PRT
<213> ORGANISM: Neisseria meningitidis

<400> SEQUENCE: 40

Met Lys Ile Ser Phe His Leu Ala Leu Leu Pro Thr Leu Ile Ile Ala
1               5                   10                  15

Ser Phe Pro Val Ala Ala Ala Asp Thr Gln Asp Asn Gly Glu His Tyr
            20                  25                  30

Thr Ala Thr Leu Pro Thr Val Ser Val Val Gly Gln Ser Asp Thr Ser
        35                  40                  45

Val Leu Lys Gly Tyr Ile Asn Tyr Asp Glu Ala Ala Val Thr Arg Asn
    50                  55                  60

Gly Gln Leu Ile Lys Glu Thr Pro Gln Thr Ile Asp Thr Leu Asn Ile
65                  70                  75                  80

Lys Asn Lys Asn Tyr Gly Thr Asn Asp Leu Ser Ser Ile Leu Glu Gly
                85                  90                  95

Asn Ala Gly Ile Asp Ala Ala Tyr Asp Met Arg Gly Glu Ser Ile Phe
            100                 105                 110

Leu Arg Gly Phe Gln Ala Asp Ala Ser Asp Ile Tyr Arg Asp Gly Val
        115                 120                 125

Arg Glu Ser Gly Gln Val Arg Arg Ser Thr Ala Asn Ile Glu Arg Val
    130                 135                 140

Glu Ile Leu Lys Gly Pro Ser Ser Val Leu Tyr Gly Arg Thr Asn Gly
145                 150                 155                 160

Gly Gly Val Ile Asn Met Val Ser Lys Tyr Ala Asn Phe Lys Gln Ser
                165                 170                 175

Arg Asn Ile Gly Ala Val Tyr Gly Ser Trp Ala Asn Arg Ser Leu Asn
```

-continued

```
            180                 185                 190

Met Asp Ile Asn Glu Val Leu Asn Lys Asn Val Ala Ile Arg Leu Thr
        195                 200                 205

Gly Glu Val Gly Arg Ala Asn Ser Phe Arg Ser Gly Ile Asp Ser Lys
    210                 215                 220

Asn Val Met Val Ser Pro Ser Ile Thr Val Lys Leu Asp Asn Gly Leu
225                 230                 235                 240

Lys Trp Thr Gly Gln Tyr Thr Tyr Asp Asn Val Glu Arg Thr Pro Asp
                245                 250                 255

Arg Ser Pro Thr Lys Ser Val Tyr Asp Arg Phe Gly Leu Pro Tyr Arg
            260                 265                 270

Met Gly Phe Ala His Arg Asn Asp Phe Val Lys Asp Lys Leu Gln Val
        275                 280                 285

Trp Arg Ser Asp Leu Glu Tyr Ala Phe Asn Asp Lys Trp Arg Ala Gln
    290                 295                 300

Trp Gln Leu Ala His Arg Thr Ala Ala Gln Asp Phe Asp His Phe Tyr
305                 310                 315                 320

Ala Gly Ser Glu Asn Gly Asn Leu Ile Lys Arg Asn Tyr Ala Trp Gln
                325                 330                 335

Gln Thr Asp Asn Lys Thr Leu Ser Ser Asn Phe Thr Leu Asn Gly Asp
            340                 345                 350

Tyr Thr Ile Gly Arg Phe Glu Asn His Leu Thr Val Gly Met Asp Tyr
        355                 360                 365

Ser Arg Glu His Arg Asn Pro Thr Leu Gly Tyr Arg Gly Ser Phe Thr
    370                 375                 380

Val Pro Ile Asn Pro Tyr Asp Arg Ala Ser Trp Pro Ala Ser Gly Arg
385                 390                 395                 400

Leu Gln Pro Ile Leu Thr Gln Asn Arg His Lys Ala Asp Ser Tyr Gly
                405                 410                 415

Ile Phe Val Gln Asn Ile Phe Ser Ala Thr Pro Asp Leu Lys Phe Val
            420                 425                 430

Leu Gly Gly Arg Tyr Asp Lys Tyr Thr Phe Asn Ser Glu Asn Lys Leu
        435                 440                 445

Thr Gly Asn Ser Arg Gln Tyr Ser Gly His Ser Phe Ser Pro Asn Ile
    450                 455                 460

Gly Ala Val Trp Asn Ile Asn Pro Val His Thr Leu Tyr Ala Ser Tyr
465                 470                 475                 480

Asn Lys Gly Phe Ala Pro Tyr Gly Gly Arg Gly Gly Tyr Leu Ser Ile
                485                 490                 495

Asp Thr Leu Ser Ser Ala Val Phe Asn Ala Asp Pro Glu Tyr Thr Arg
            500                 505                 510

Gln Tyr Glu Thr Gly Val Lys Ser Ser Trp Leu Asp Asp Arg Leu Ser
        515                 520                 525

Thr Thr Leu Ser Ala Tyr Gln Ile Glu Arg Phe Asn Ile Arg Tyr Arg
    530                 535                 540

Pro Asp Pro Lys Asn Asn Pro Tyr Ile Tyr Ala Val Ser Gly Lys His
545                 550                 555                 560

Arg Ser Arg Gly Val Glu Leu Ser Ala Ile Gly Gln Ile Ile Pro Lys
                565                 570                 575

Lys Leu Tyr Leu Arg Gly Ser Leu Gly Val Met Gln Ala Lys Val Val
            580                 585                 590

Glu Asp Lys Glu Asn Pro Asp Arg Val Gly Ile His Leu Asn Asn Thr
        595                 600                 605
```

-continued

Ser Asn Val Thr Gly Asn Leu Phe Phe Arg Tyr Thr Pro Thr Glu Asn
610 615 620

Leu Tyr Gly Glu Ile Gly Val Thr Gly Thr Gly Lys Arg Tyr Gly Tyr
625 630 635 640

Asn Ser Arg Asn Lys Glu Val Thr Thr Leu Pro Gly Phe Ala Arg Val
645 650 655

Asp Ala Met Leu Gly Trp Asn His Lys Asn Val Asn Val Thr Phe Ala
660 665 670

Ala Ala Asn Leu Phe Asn Gln Lys Tyr Trp Arg Ser Asp Ser Met Pro
675 680 685

Gly Asn Pro Arg Gly Tyr Thr Ala Arg Val Asn Tyr Arg Phe
690 695 700

<210> SEQ ID NO 41
<211> LENGTH: 2112
<212> TYPE: DNA
<213> ORGANISM: Neisseria meningitidis

<400> SEQUENCE: 41
atgaaaatat catttcattt agctttatta cccacgctga ttattgcttc cttccctgtt 60
gctgccgccg atacgcagga caatggtgaa cattacaccg ccactctgcc caccgtttcc 120
gtggtcggac agtccgacac cagcgtactc aaaggctaca tcaactacga cgaagccgcc 180
gttacccgca acggacagct catcaaagaa acgccgcaaa ccatcgatac gctcaatatc 240
cagaaaaaca aaaattacgg tacgaacgat ttgagttcca tcctcgaagg caatgccggc 300
atcgacgctg cctacgatat gcgcggcgaa agcattttcc tgcgcggttt tcaagccgac 360
gcatccgata tttaccgcga cggcgtgcgc gaaagcggac aagtgcgccg cagtactgcc 420
aacatcgagc gcgtggaaat cctgaaaggc ccgtcttccg tgctttacgg ccgcaccaac 480
ggcggcggcg tcatcaacat ggtcagcaaa tacgccaact tcaaacaaag ccgcaacatc 540
ggtgcggttt acggttagtg ggcaaaccgc agcctgaata tggacattaa cgaagtgctg 600
aacaaaaacg tcgccatccg tctcaccggc gaagtcgggc gcgccaattc gttccgcagc 660
ggcatagaca gcaaaaatgt catggtttcg cccagcatta ccgtcaaact cgacaacggc 720
ttgaagtgga cggggcaata cacctacgac aatgtggagc gcacgcccga ccgcagtccg 780
accaagtccg tgtacgaccg cttcggactg ccttaccgca tggggttcgc ccaccggaac 840
gattttgtca aagacaagct gcaagtttgg cgttccgacc ttgaatacgc cttcaacgac 900
aaatggcgtg cccaatggca gctcgcccac cgcacggcgg cgcaggattt tgatcatttc 960
tatgcaggca gcgaaaatgg caacttaatc aaacgtaact acgcctggca gcagactgac 1020
aacaaaaccc tgtcgtccaa tttcacgcta aacggcgact acaccatcgg ccgttttgaa 1080
aaccacttga ccgtaggcat ggattacagc cgcgaacacc gcaacccgac cttaggttac 1140
aaccgcgcct tttccgcctc catcaacccc tacgaccgcg caagctggcc ggcttcgggc 1200
agattgcagc ctattctgac ccaaaaccgc cacaaagccg actcctacgg catctttgtg 1260
caaaacatct tctccgccac gcccgatttg aaattcgtcc tcggcggccg ttacgacaaa 1320 tacacctta attccgaaaa caaactcacc ggcagcagcc gccaatacag cggacactcg 1380
ttcagcccca acatcggcgc agtgtggaac atcaatcccg tccacacact ttacgcctcg 1440
tataacaaag gcttcgcgcc ttatggcgga cgcggcggct atttgagcat cgatacgttg 1500
tcttccgccg tgttcaacgc cgaccccgag tacacccgcc aatacgaaac cggcgtgaaa 1560

-continued

```
agcagttggc tggacgaccg cctcagcact acgttgtctg cctaccaaat cgaacgcttc   1620

aatatccgct accgccccga tccaaaaaac aacccttata tttatgcggt tagcggcaaa   1680

caccgttcgc gcggcgtgga attgtccgcc atcgggcaaa tcatccctaa aaaactctat   1740

ctgcgcggtt cgttgggcgt gatgcaggcg aaagtcgttg aagacaaaga aaatcccgac   1800

cgagtgggca tccatttgaa taacaccagc aacgttaccg gcaacctgtt tttccgttat   1860

accccgaccg aaaacctcta cggcgaaatc ggcgtaaccg gtacaggcaa acgctacggt   1920

tacgactcaa gaaataaaga agtgactacg cttccaggct ttgcccgagt tgatgccatg   1980

cttggctgga accataaaaa tgttaacgtt acctttgccg cagccaatct gttcaatcaa   2040

aaatattggc gttcggactc tatgccgggt aatccgcgcg gctatactgc ccgggtaaat   2100

taccgtttct ga                                                       2112


<210> SEQ ID NO 42
<211> LENGTH: 702
<212> TYPE: PRT
<213> ORGANISM: Neisseria meningitidis

<400> SEQUENCE: 42

Met Lys Ile Ser Phe His Leu Ala Leu Leu Pro Thr Leu Ile Ile Ala
1               5                   10                  15

Ser Phe Pro Val Ala Ala Ala Asp Thr Gln Asp Asn Gly Glu His Tyr
            20                  25                  30

Thr Ala Thr Leu Pro Thr Val Ser Val Val Gly Gln Ser Asp Thr Ser
        35                  40                  45

Val Leu Lys Gly Tyr Ile Asn Tyr Asp Glu Ala Ala Val Thr Arg Asn
    50                  55                  60

Gly Gln Leu Ile Lys Glu Thr Pro Gln Thr Ile Asp Thr Leu Asn Ile
65                  70                  75                  80

Gln Lys Asn Lys Asn Tyr Gly Thr Asn Asp Leu Ser Ser Ile Leu Glu
                85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Ala Val Tyr Gly Trp Ala Asn Arg Ser Leu Asn
            180                 185                 190

Met Asp Ile Asn Glu Val Leu Asn Lys Asn Val Ala Ile Arg Leu Thr
        195                 200                 205

Gly Glu Val Gly Arg Ala Asn Ser Phe Arg Ser Gly Ile Asp Ser Lys
    210                 215                 220

Asn Val Met Val Ser Pro Ser Ile Thr Val Lys Leu Asp Asn Gly Leu
225                 230                 235                 240

Lys Trp Thr Gly Gln Tyr Thr Tyr Asp Asn Val Glu Arg Thr Pro Asp
                245                 250                 255

Arg Ser Pro Thr Lys Ser Val Tyr Asp Arg Phe Gly Leu Pro Tyr Arg
            260                 265                 270
```

-continued

```
Met Gly Phe Ala His Arg Asn Asp Phe Val Lys Asp Lys Leu Gln Val
        275                 280                 285

Trp Arg Ser Asp Leu Glu Tyr Ala Phe Asn Asp Lys Trp Arg Ala Gln
    290                 295                 300

Trp Gln Leu Ala His Arg Thr Ala Ala Gln Asp Phe Asp His Phe Tyr
305                 310                 315                 320

Ala Gly Ser Glu Asn Gly Asn Leu Ile Lys Arg Asn Tyr Ala Trp Gln
                325                 330                 335

Gln Thr Asp Asn Lys Thr Leu Ser Ser Asn Phe Thr Leu Asn Gly Asp
            340                 345                 350

Tyr Thr Ile Gly Arg Phe Glu Asn His Leu Thr Val Gly Met Asp Tyr
        355                 360                 365

Ser Arg Glu His Arg Asn Pro Thr Leu Gly Tyr Asn Arg Ala Phe Ser
    370                 375                 380

Ala Ser Ile Asn Pro Tyr Asp Arg Ala Ser Trp Pro Ala Ser Gly Arg
385                 390                 395                 400

Leu Gln Pro Ile Leu Thr Gln Asn Arg His Lys Ala Asp Ser Tyr Gly
                405                 410                 415

Ile Phe Val Gln Asn Ile Phe Ser Ala Thr Pro Asp Leu Lys Phe Val
            420                 425                 430

Leu Gly Gly Arg Tyr Asp Lys Tyr Thr Phe Asn Ser Glu Asn Lys Leu
        435                 440                 445

Thr Gly Ser Ser Arg Gln Tyr Ser Gly His Ser Phe Ser Pro Asn Ile
    450                 455                 460

Gly Ala Val Trp Asn Ile Asn Pro Val His Thr Leu Tyr Ala Ser Tyr
465                 470                 475                 480

Asn Lys Gly Phe Ala Pro Tyr Gly Gly Arg Gly Gly Tyr Leu Ser Ile
                485                 490                 495

Asp Thr Leu Ser Ser Ala Val Phe Asn Ala Asp Pro Glu Tyr Thr Arg
            500                 505                 510

Gln Tyr Glu Thr Gly Val Lys Ser Ser Trp Leu Asp Asp Arg Leu Ser
        515                 520                 525

Thr Thr Leu Ser Ala Tyr Gln Ile Glu Arg Phe Asn Ile Arg Tyr Arg
    530                 535                 540

Pro Asp Pro Lys Asn Asn Pro Tyr Ile Tyr Ala Val Ser Gly Lys His
545                 550                 555                 560

Arg Ser Arg Gly Val Glu Leu Ser Ala Ile Gly Gln Ile Ile Pro Lys
                565                 570                 575

Lys Leu Tyr Leu Arg Gly Ser Leu Gly Val Met Gln Ala Lys Val Val
            580                 585                 590

Glu Asp Lys Glu Asn Pro Asp Arg Val Gly Ile His Leu Asn Asn Thr
        595                 600                 605

Ser Asn Val Thr Gly Asn Leu Phe Phe Arg Tyr Thr Pro Thr Glu Asn
    610                 615                 620

Leu Tyr Gly Glu Ile Gly Val Thr Gly Thr Gly Lys Arg Tyr Gly Tyr
625                 630                 635                 640

Asp Ser Arg Asn Lys Glu Val Thr Thr Leu Pro Gly Phe Ala Arg Val
                645                 650                 655

Asp Ala Met Leu Gly Trp Asn His Lys Asn Val Asn Val Thr Phe Ala
            660                 665                 670

Ala Ala Asn Leu Phe Asn Gln Lys Tyr Trp Arg Ser Asp Ser Met Pro
        675                 680                 685

Gly Asn Pro Arg Gly Tyr Thr Ala Arg Val Asn Tyr Arg Phe
```

-continued 690 695 700

<210> SEQ ID NO 43
<211> LENGTH: 2109
<212> TYPE: DNA
<213> ORGANISM: Neisseria meningitidis

<400> SEQUENCE: 43
atgaaaatat catttcattt agctttatta cccacgctga ttattgcttc cttccctgtt 60
gctgccgccg atacgcagga caatggtgaa cattacaccg ccactctgcc caccgtttcc 120
gtggtcggac agtccgacac cagcgtactc aaaggctaca tcaactacga cgaagccgcc 180
gttacccgca acggacagct catcaaagaa acgccgcaaa ccatcgatac gctcaatatc 240
cagaaaaaca aaaattacgg tacgaacgat ttgagttcca tcctcgaagg caatgccggc 300
atcgacgctg cctacgatat gcgcggtgaa agcattttcc tgcgcggttt tcaagccgac 360
gcatccgata tttaccgcga cggcgtgcgc gaaagcggac aagtgcgccg cagtactgcc 420
aacatcgagc gcgtggaaat cctgaaaggc ccgtcttccg tgctttacgg ccgcaccaac 480
ggcggcggcg tcatcaacat ggtcagcaaa tacgccaact tcaaacaaag ccgcaacatc 540
ggtgcggttt acggttcgtg ggcaaaccgc agcctgaata tggacattaa cgaagtgctg 600
aacaaaaacg tcgccatccg tctcaccggc gaagtcgggc gcgccaattc gttccgcagc 660
ggcatagaca gcaaaaatgt catggtttcg cccagcatta ccgtcaaact cgacaacggc 720
ttgaagtgga cggggcaata cacctacgac aatgtggagc gcacgcccga ccgcagtccg 780
accaagtccg tgtacgaccg cttcggactg ccttaccgca tggggttcgc ccaccggaac 840
gattttgtca aagacaagct gcaagtttgg cgttccgacc ttgaatacgc cttcaacgac 900
aaatggcgtg cccaatggca gctcgcccac cgcacggcgg cgcaggattt tgatcatttc 960
tatgcaggca gcgaaaatgg caacttaatc aaacgtaact acgcctggca gcagaccgac 1020
aacaaaaccc tgtcgtccaa cttaacgctc aacggcgact acaccatcgg ccgttttgaa 1080
aaccacctga ccgtaggcat ggattacagt cgcgaacacc gcaacccgac attgggctac 1140
cgcggcagtt tcaccgtgcc catcaacccc tacgaccgcg caagctggcc ggcttcgggc 1200
agattgcagc ctattctgac ccaaaaccgc cacaaagccg actcctacgg catctttgtg 1260
caaaacatct tctccgctac gcccgatttg aaattcgtcc tcggcggccg ttacgacaaa 1320
tacaccttta attccgaaaa caaactcacc ggcaacagcc gccaatacag cggacactcg 1380
ttcagcccca acatcggcgc agtgtggaac atcaacccag tccacacact ttatgcctcg 1440
tataacaaag gcttcgcgcc ttatggcgga cgcggctatt tgagtatcga cacttcgtct 1500
gccgccgtgt tcaacgccgc ccccgagtac actcgccaat acgaaaccgg tgtgaaaagc 1560
agttggctgg acgaccgcct cagcaccaca ttgtccgcct accaaatcga acgcttcaat 1620
atccgctacc gccccgatcc aaaaaacaac ccttatattt atgcggttag cggcaaacac 1680
cgttcgcgcg gcgtggaatt gtccgccatc gggcaaatca tccctaaaaa actctatctg 1740
cgcggttcgt tgggcgtgat gcaggcgaaa gtcgttgaag acaaagaaaa tcccgaccga 1800
gtgggcatcc atttgaataa caccagcaac gttaccggca acctgttttt ccgttatacc 1860
ccgactgaaa acctctacgg cgaaatcggc gtaaccggta caggcaaacg ctacggctac 1920
aactcaagaa ataaagaagt gaccacgctt ccaggctttg cccgagttga tgccatgctc 1980
ggctggaacc ataaaaatgt taacgttacc tttgccgctg ccaatctgct caatcaaaaa 2040
tattggcgtt cggactctat gccgggtaat ccgcgcggct atactgcccg ggtaaattac 2100
cgtttctga 2109

<210> SEQ ID NO 44
<211> LENGTH: 702
<212> TYPE: PRT
<213> ORGANISM: Neisseria meningitidis

<400> SEQUENCE: 44

```
Met Lys Ile Ser Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30

Thr Ala Thr Leu Pro Thr Val Ser Val Val Gly Gln Ser Asp Thr Ser
         35                  40                  45

Val Leu Lys Gly Tyr Ile Asn Tyr Asp Glu Ala Ala Val Thr Arg Asn
     50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                 85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Ala Val Tyr Gly Ser Trp Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
    210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
            260                 265                 270

Arg Met Gly Phe Ala His Arg Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300

Gln Trp Gln Leu Ala His Arg Thr Ala Ala Gln Asp Phe Asp His Phe
305                 310                 315                 320

Tyr Ala Gly Ser Glu Asn Gly Asn Leu Ile Lys Arg Asn Tyr Ala Trp
                325                 330                 335

Gln Gln Thr Asp Asn Lys Thr Leu Ser Ser Asn Leu Thr Leu Asn Gly
            340                 345                 350

Asp Tyr Thr Ile Gly Arg Phe Glu Asn His Leu Thr Val Gly Met Asp
        355                 360                 365
```

-continued

```
Tyr Ser Arg Glu His Arg Asn Pro Thr Leu Gly Tyr Arg Gly Ser Phe
    370                 375                 380

Thr Val Pro Ile Asn Pro Tyr Asp Arg Ala Ser Trp Pro Ala Ser Gly
385                 390                 395                 400

Arg Leu Gln Pro Ile Leu Thr Gln Asn Arg His Lys Ala Asp Ser Tyr
                405                 410                 415

Gly Ile Phe Val Gln Asn Ile Phe Ser Ala Thr Pro Asp Leu Lys Phe
            420                 425                 430

Val Leu Gly Gly Arg Tyr Asp Lys Tyr Thr Phe Asn Ser Glu Asn Lys
        435                 440                 445

Leu Thr Gly Asn Ser Arg Gln Tyr Ser Gly His Ser Phe Ser Pro Asn
    450                 455                 460

Ile Gly Ala Val Trp Asn Ile Asn Pro Val His Thr Leu Tyr Ala Ser
465                 470                 475                 480

Tyr Asn Lys Gly Phe Ala Pro Tyr Gly Gly Arg Gly Tyr Leu Ser Ile
                485                 490                 495

Asp Thr Ser Ser Ala Ala Val Phe Asn Ala Ala Pro Glu Tyr Thr Arg
            500                 505                 510

Gln Tyr Glu Thr Gly Val Lys Ser Ser Trp Leu Asp Asp Arg Leu Ser
        515                 520                 525

Thr Thr Leu Ser Ala Tyr Gln Ile Glu Arg Phe Asn Ile Arg Tyr Arg
    530                 535                 540

Pro Asp Pro Lys Asn Asn Pro Tyr Ile Tyr Ala Val Ser Gly Lys His
545                 550                 555                 560

Arg Ser Arg Gly Val Glu Leu Ser Ala Ile Gly Gln Ile Ile Pro Lys
                565                 570                 575

Lys Leu Tyr Leu Arg Gly Ser Leu Gly Val Met Gln Ala Lys Val Val
            580                 585                 590

Glu Asp Lys Glu Asn Pro Asp Arg Val Gly Ile His Leu Asn Asn Thr
        595                 600                 605

Ser Asn Val Thr Gly Asn Leu Phe Phe Arg Tyr Thr Pro Thr Glu Asn
    610                 615                 620

Leu Tyr Gly Glu Ile Gly Val Thr Gly Thr Gly Lys Arg Tyr Gly Tyr
625                 630                 635                 640

Asn Ser Arg Asn Lys Glu Val Thr Thr Leu Pro Gly Phe Ala Arg Val
                645                 650                 655

Asp Ala Met Leu Gly Trp Asn His Lys Asn Val Asn Val Thr Phe Ala
            660                 665                 670

Ala Ala Asn Leu Leu Asn Gln Lys Tyr Trp Arg Ser Asp Ser Met Pro
        675                 680                 685

Gly Asn Pro Arg Gly Tyr Thr Ala Arg Val Asn Tyr Arg Phe
    690                 695                 700
```

<210> SEQ ID NO 45
<211> LENGTH: 2108
<212> TYPE: DNA
<213> ORGANISM: Neisseria meningitidis

<400> SEQUENCE: 45

```
atgaaaatat catttcattt agctttatta cccacgctga ttattgcttc cttccctgtt      60

gctgccgccg atacgcagga caatggtgaa cattacaccg ccacgctacc taccgtttcc     120

gtggtcggac agtccgacac cagcgtactc aaaggctaca tcaactacga cgaagccgcc     180

gttacccgca acggacagct catcaaagaa acgccgcaaa ccatcgatac gctcaatatc     240
```

-continued

```
cagaaaaaca aaaattacgg cacgaacgat ttgagttcca tcctcgaagg caatgccggc    300
atcgacgctg cctacgatat gcgcggtgaa agcattttcc tgcgcggttt tcaagccgac    360
gcatccgata tttaccgcga cggcgtgcgc gaaagcggac aagtgcgccg cagtactgcc    420
aacatcgagc gcgtggaaat cctgaaaggc ccgtcttccg tgctttacgg ccgtaccaac    480
ggcggcggcg tcatcaacat ggtcagcaaa tacgccaact tcaaacaaag ccgcaacatc    540
ggtgcggttt acggttcgtg ggcaaaccgc agcctgaata tggacattaa cgaagtgctg    600
aacaaaaacg tcgccatccg tctcaccggc gaagtcgggc gcgccaattc gttccgcagc    660
ggcatagaca gcaaaaatgt catggtttcg cccagcatta ccgtcaaact cgacaacggc    720
ttgaagtgga cggggcaata cacctacgac aatgtggagc gcacgcccga ccgcagtccg    780
accaagtccg tgtacgaccg cttcggactg ccttaccgca tggggttcgc ccacccgaac    840
gattttgtca aagacaagct gcaagtttgg cgttccgacc tcgaatacgc cttcaacgac    900
aaatggcgcg cccaatggca gctcgcccac cgcacggcag cgcaggattt cgaccatttt    960
tatgcaggca gcgaaaacgg cagccgaatc aaacgcaact acgcctggca gcagaccgac   1020
aacaaaactc tgtcgtccaa cttcacgctc aacggcgact acaccatcgg tcgttttgaa   1080
aaccacctga ccgtaggcat ggattacagc cgcgaacacc gcaacccgac attgggctac   1140
cgcggcagtt tcaccgtgcc catcaacccc tacgaccgcg caagctggcc ggcttcgggc   1200
agattgcagc ctattctgac ccaaaaccgc cacaaagccg actcctacgg catctttgtg   1260
caaaacatct tctccgctac gcccgatttg aaattcgtcc tcggcggccg ttacgacaaa   1320
tacaccttta attccgaaaa caaactcacc ggcaacagcc gccaatacag cggacactcg   1380
ttcagcccca acatcggcgc agtgtggaac atcaacccag tccacacact ttacgcctcg   1440
tataacaaag gcttcgcgcc ttatggcgga cgcggatatt tgagtatcga cacttcgtct   1500
gccgccgtgt tcaacgccgc ccccgagtac acccccaata cgaaaccggc gtcaaaagca   1560
gttggctgga caatcgtttg gacaccaccc tgtcggttta ccaaatcgaa cgcttcaata   1620
tccgctaccg ccccgatcca aaaaacaacc cttatattta tgcggttagc ggcaaacacc   1680
gttcgcgcgg cgtggaattg tccgccatcg ggcaaatcat ccccaaaaaa ctctatctgc   1740
gcggttcgtt gggcgtgatg caggcgaaag tcgttgaaga caaagaaaat cccgaccgag   1800
tgggcatcca tttgaataac accagcaacg ttaccggcaa cctgtttttc cgttataccc   1860
cgaccgaaaa cctctacggc gaaatcggcg taaccggtac gggcaaacgc tacggttaca   1920
actcaagaaa taaagaagtg actacgcttc caggctttgc ccgagttgat gccatgcttg   1980
gctggaacca taaaaatgtt aacgttacct ttgccgcagc caatctgttc aatcaaaaat   2040
attggcgttc ggactctatg ccgggtaatc cgcgcggcta tactgcccgg gtaaattacc   2100
gtttctga                                                             2108
```

<210> SEQ ID NO 46
<211> LENGTH: 697
<212> TYPE: PRT
<213> ORGANISM: Neisseria meningitidis

<400> SEQUENCE: 46

```
Met Lys Ile Ser Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30
```

-continued

```
Thr Ala Thr Leu Pro Thr Val Ser Val Val Gly Gln Ser Asp Thr Ser
        35                  40                  45

Val Leu Lys Gly Tyr Ile Asn Tyr Asp Glu Ala Ala Val Thr Arg Asn
    50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Ala Val Tyr Gly Ser Trp Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
    210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
            260                 265                 270

Arg Met Gly Phe Ala His Pro Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300

Gln Trp Gln Leu Ala His Arg Thr Ala Ala Gln Asp Phe Asp His Phe
305                 310                 315                 320

Tyr Ala Gly Ser Glu Asn Gly Ser Arg Ile Lys Arg Asn Tyr Ala Trp
                325                 330                 335

Gln Gln Thr Asp Asn Lys Thr Leu Ser Ser Asn Phe Thr Leu Asn Gly
            340                 345                 350

Asp Tyr Thr Ile Gly Arg Phe Glu Asn His Leu Thr Val Gly Met Asp
        355                 360                 365

Tyr Ser Arg Glu His Arg Asn Pro Thr Leu Gly Tyr Arg Gly Ser Phe
    370                 375                 380

Thr Val Pro Ile Asn Pro Tyr Asp Arg Ala Ser Trp Pro Ala Ser Gly
385                 390                 395                 400

Arg Leu Gln Pro Ile Leu Thr Gln Asn Arg His Lys Ala Asp Ser Tyr
                405                 410                 415

Gly Ile Phe Val Gln Asn Ile Phe Ser Ala Thr Pro Asp Leu Lys Phe
            420                 425                 430

Val Leu Gly Gly Arg Tyr Asp Lys Tyr Thr Phe Asn Ser Glu Asn Lys
        435                 440                 445

Leu Thr Gly Asn Ser Arg Gln Tyr Ser Gly His Ser Phe Ser Pro Asn
```

-continued

```
    450                 455                 460

Ile Gly Ala Val Trp Asn Ile Asn Pro Val His Thr Leu Tyr Ala Ser
465                 470                 475                 480

Tyr Asn Lys Gly Phe Ala Pro Tyr Gly Gly Arg Gly Tyr Leu Ser Ile
                485                 490                 495

Asp Thr Ser Ser Ala Ala Val Phe Asn Ala Ala Pro Glu Tyr Thr Pro
            500                 505                 510

Asn Thr Lys Pro Ala Ser Lys Ala Val Gly Trp Thr Ile Val Trp Thr
        515                 520                 525

Pro Pro Cys Arg Phe Thr Lys Ser Asn Ala Ser Ile Ser Ala Thr Ala
    530                 535                 540

Pro Ile Gln Lys Thr Thr Leu Ile Phe Met Arg Leu Ala Ala Asn Thr
545                 550                 555                 560

Val Arg Ala Ala Trp Asn Cys Pro Pro Ser Gly Lys Ser Ser Pro Lys
                565                 570                 575

Asn Ser Ile Cys Ala Val Arg Trp Ala Cys Arg Arg Lys Ser Leu Lys
            580                 585                 590

Thr Lys Lys Ile Pro Thr Glu Trp Ala Ser Ile Ile Thr Pro Ala Thr
        595                 600                 605

Leu Pro Ala Thr Cys Phe Ser Val Ile Pro Arg Pro Lys Thr Ser Thr
    610                 615                 620

Ala Lys Ser Ala Pro Val Arg Ala Asn Ala Thr Val Thr Thr Gln Glu
625                 630                 635                 640

Ile Lys Lys Leu Arg Phe Gln Ala Leu Pro Glu Leu Met Pro Cys Leu
                645                 650                 655

Ala Gly Thr Ile Lys Met Leu Thr Leu Pro Leu Pro Gln Pro Ile Cys
            660                 665                 670

Ser Ile Lys Asn Ile Gly Val Arg Thr Leu Cys Arg Val Ile Arg Ala
        675                 680                 685

Ala Ile Leu Pro Gly Ile Thr Val Ser
    690                 695
```

<210> SEQ ID NO 47
<211> LENGTH: 2113
<212> TYPE: DNA
<213> ORGANISM: Neisseria meningitidis

<400> SEQUENCE: 47

```
atgcaaatac catttcattt ggctttatta cccacgctga ttattgcttc cttccctgtt      60

gctgccgccg atacgcagga caatggtgaa cattacaccg ccacgctacc taccgtttcc     120

gtggtcggac agtccgacac cagcgtactc aaaggctaca tcaactacga cgaagccgcc     180

gttacccgca acggacagct catcaaagaa acgccgcaaa ccatcgatac gctcaatatc     240

cagaaaaaca aaaattacgg cacgaacgat ttgagttcca tcctcgaagg caatgccggc     300

atcgacgccg cctacgatat gcgcggcgaa agcattttcc tgcgcggctt tcaagccgac     360

gcatctgata tttaccgcga cggcgtacgc gaaagcgggc aggtgcgccg tagcaccgcc     420

aacatcgagc gcgtggaaat cctgaaaggt ccgtcctccg tgctttatgg gcgtaccaac     480

ggcggcggtg tcatcaacat ggtcagcaaa tacgccaact tcaaacaaag ccgtaatatc     540

ggtacggttt atggttcgtg ggcaaaccgt agcctgaata tggacatcaa cgaagtgctg     600

aacaaaaacg tcgccatccg tctcaccggc gaagtcgggc gcgccaattc gttccgcagc     660

ggcatagaca gcaaaaatgt catggtttcg cccagcatta ccgtcaaact cgacaacggc     720
```

-continued

```
ttgaagtgga cggggcaata cacctacgac aatgtggagc gcacgcccga ccgcagtccg    780

accaagtccg tgtacgaccg cttcggactg ccttaccgca tggggttcgc ccaccggaac    840

gattttgtca aagacaagct gcaagtttgg cgttccgacc ttgaatacgc cttcaacgac    900

aaatggcgtg cccaatggca gctcgcccac cgcacggcgg cgcaggattt tgatcatttc    960

tatgcaggca gcgaaaatgg caacttaatc aaacgtaact acgcctggca gcagaccgac   1020

aacaaaaccc tgtcgtccaa cttaacgctc aacggcgact acaccatcgg ccgttttgaa   1080

aaccacctga ccgtaggcat ggattacagc cgcgaacacc gcaacccgac attgggtttc   1140

agcagcgcct tttccgcctc catcaacccc tacgaccgcg caagctggcc ggcttcgggc   1200

agattgcagc ctattctgac ccaaaaccgc cacaaagccg actcctacgg catctttgtg   1260

caaaacatct tctccgccac gcccgatttg aaattcgtcc tcggcggccg ttacgacaaa   1320

tacaccttta attccgaaaa caaactcacc ggcagcagcc gccaatacag cggacactcg   1380

ttcagcccca acatcggcgc agtgtggaac atcaatcccg tccacacact ttacgcctcg   1440

tataacaaag gcttcgcgcc ttatggcgga cgcggcggct atttgagcat cgatacgttg   1500

tcttccgccg tgttcaacgc cgaccccgag tacacccgcc aatacgaaac cggcgtgaaa   1560

agcagttggc tggacgaccg cctcagcact acgttgtctg cctaccaaat cgaacgcttc   1620

aatatccgct accgccccga tccaaaaaac aacccttata tttatgcggt tagcggcaaa   1680

caccgttcgc gcggcgtgga attgtccgcc atcgggcaaa tcatccccaa aaaaactcta   1740

tctgcgcggt tcgttgggcg tgatgcaggc gaaagtcgtt gaagacaaag aaaatcccga   1800

ccgagtgggc atccatttga ataacaccag caacgttacc ggcaacctgt tttccgttta   1860

taccccgacc gaaaacctct acggcgaaat cggcgtaacc ggtacaggca aacgctacgg   1920

ttacgactca agaaataaag aagtgactac gcttccaggc tttgcccgag ttgatgccat   1980

gcttggctgg aaccataaaa atgttaacgt tacctttgcc gcagccaatc tgttcaatca   2040

aaaatattgg cgttcggact ctatgccggg taatccgcgc ggctatactg cccgggtaaa   2100

ttaccgtttc tga                                                      2113
```

<210> SEQ ID NO 48
<211> LENGTH: 697
<212> TYPE: PRT
<213> ORGANISM: Neisseria meningitidis

<400> SEQUENCE: 48

```
Met Gln Ile Pro Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30

Thr Ala Thr Leu Pro Thr Val Ser Val Val Gly Gln Ser Asp Thr Ser
         35                  40                  45

Val Leu Lys Gly Tyr Ile Asn Tyr Asp Glu Ala Ala Val Thr Arg Asn
     50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                 85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125
```

-continued

```
Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Thr Val Tyr Gly Ser Trp Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
    210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
            260                 265                 270

Arg Met Gly Phe Ala His Arg Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300

Gln Trp Gln Leu Ala His Arg Thr Ala Ala Gln Asp Phe Asp His Phe
305                 310                 315                 320

Tyr Ala Gly Ser Glu Asn Gly Asn Leu Ile Lys Arg Asn Tyr Ala Trp
                325                 330                 335

Gln Gln Thr Asp Asn Lys Thr Leu Ser Ser Asn Leu Thr Leu Asn Gly
            340                 345                 350

Asp Tyr Thr Ile Gly Arg Phe Glu Asn His Leu Thr Val Gly Met Asp
        355                 360                 365

Tyr Ser Arg Glu His Arg Asn Pro Thr Leu Gly Phe Ser Ser Ala Phe
    370                 375                 380

Ser Ala Ser Ile Asn Pro Tyr Asp Arg Ala Ser Trp Pro Ala Ser Gly
385                 390                 395                 400

Arg Leu Gln Pro Ile Leu Thr Gln Asn Arg His Lys Ala Asp Ser Tyr
                405                 410                 415

Gly Ile Phe Val Gln Asn Ile Phe Ser Ala Thr Pro Asp Leu Lys Phe
            420                 425                 430

Val Leu Gly Gly Arg Tyr Asp Lys Tyr Thr Phe Asn Ser Glu Asn Lys
        435                 440                 445

Leu Thr Gly Ser Ser Arg Gln Tyr Ser Gly His Ser Phe Ser Pro Asn
    450                 455                 460

Ile Gly Ala Val Trp Asn Ile Asn Pro Val His Thr Leu Tyr Ala Ser
465                 470                 475                 480

Tyr Asn Lys Gly Phe Ala Pro Tyr Gly Gly Arg Gly Gly Tyr Leu Ser
                485                 490                 495

Ile Asp Thr Leu Ser Ser Ala Val Phe Asn Ala Asp Pro Glu Tyr Thr
            500                 505                 510

Arg Gln Tyr Glu Thr Gly Val Lys Ser Ser Trp Leu Asp Asp Arg Leu
        515                 520                 525

Ser Thr Thr Leu Ser Ala Tyr Gln Ile Glu Arg Phe Asn Ile Arg Tyr
    530                 535                 540
```

-continued

```
Arg Pro Asp Pro Lys Asn Asn Pro Tyr Ile Tyr Ala Val Ser Gly Lys
545                 550                 555                 560

His Arg Ser Arg Gly Val Glu Leu Ser Ala Ile Gly Gln Ile Ile Pro
                565                 570                 575

Lys Lys Thr Leu Ser Ala Arg Phe Val Gly Arg Asp Ala Gly Glu Ser
            580                 585                 590

Arg Arg Gln Arg Lys Ser Arg Pro Ser Gly His Pro Phe Glu His Gln
        595                 600                 605

Gln Arg Tyr Arg Gln Pro Val Phe Pro Leu Tyr Pro Asp Arg Lys Pro
    610                 615                 620

Leu Arg Arg Asn Arg Arg Asn Arg Tyr Arg Gln Thr Leu Arg Leu Arg
625                 630                 635                 640

Leu Lys Lys Arg Ser Asp Tyr Ala Ser Arg Leu Cys Pro Ser Cys His
                645                 650                 655

Ala Trp Leu Glu Pro Lys Cys Arg Tyr Leu Cys Arg Ser Gln Ser Val
            660                 665                 670

Gln Ser Lys Ile Leu Ala Phe Gly Leu Tyr Ala Gly Ser Ala Arg Leu
        675                 680                 685

Tyr Cys Pro Gly Lys Leu Pro Phe Leu
    690                 695


<210> SEQ ID NO 49
<211> LENGTH: 2112
<212> TYPE: DNA
<213> ORGANISM: Neisseria meningitidis

<400> SEQUENCE: 49

atgaaaatat catttcattt agctttatta cccacgctga ttattgcttc cttccctgtt      60

gctgccgccg atacgcagga caatggtgaa cattacaccg ccactctgcc caccgtttcc     120

gtggtcggac agtccgacac cagcgtactc aaaggctaca tcaactacga cgaagccgcc     180

gttacccgca acggacagct catcaaagaa acgccgcaaa ccatcgatac gctcaatatc     240

cagaaaaaca aaaattacgg tacgaacgat ttgagttcca tcctcgaagg caatgccggc     300

atcgacgctg cctacgatat gcgcggcgaa agcattttcc tgcgcggttt tcaagccgac     360

gcatccgata tttaccgcga cggcgtgcgc gaaagcggac aagtgcgccg cagtactgcc     420

aacatcgagc gcgtggaaat cctgaaaggc ccgtcttccg tgctttacgg ccgcaccaac     480

ggcggcggcg tcatcaacat ggtcagcaaa tacgccaact tcaaacaaag ccgcaacatc     540

ggtgcggttt acggttcgtg ggcaaaccgc agcctgaata tggacattaa cgaagtgttg     600

aacaaaaacg tcgccatccg tctcaccggc gaagtcgggc gcgccaattc gttccgcagc     660

ggcatagaca gcaaaaatgt catggtttcg cccagcatta ccgtcaaact cgacaacggc     720

ttgaagtgga cggggcaata cacctacgac aatgtggagc gcacgcccga ccgcagtccg     780

accaagtccg tgtacgaccg cttcggactg ccttaccgca tggggttcgc ccaccggaac     840

gattttgtca aagacaagct gcaagtttgg cgctccgacc ttgaatacgc cttcaacgac     900

aaatggcgtg cccaatggca gctcgcccac cgcacggcgg cgcaggattt tgatcatttc     960

tatgcaggca gcgaaaatgg caacttaatc aaacgtaact acgcctggca gcagaccgac    1020

aacaaaaccc tgtcgtccaa tttcacgcta aacggcgact acaccatcgg ccgttttgaa    1080

aaccacttga ccgtaggcat ggattacagc cgcgaacacc gcaacccgac cttaggttac    1140

agccgcgcct ttactgcttc catcgatcca tacgaccgag caagctggcc ggcttcgggc    1200

agattgcagc ctatcctcac ccaaaaccgc cacaaagccg actcctacgg catctttgtg    1260
```

-continued

```
caaaacatct tctccgccac gcccgatttg aaattcgtcc tcggcggtcg ttacgacaaa   1320

tacaccttta attccgaaaa caaactcacc ggcagcagcc gccaatacag cggacactcg   1380

ttcagcccca acatcggcgc agtgtggaac atcaatcccg tccacacact ttacgcctcg   1440

tataataaag gcttcgcgcc ttatggcgga cgcggcggct atttgagcat caacacgtcg   1500

tcttccgccg tgttcaacgc cgaccccgag tacacccgcc aatacgaaac cggtgtgaaa   1560

agcagttggc tggacgaccg cctcagcact acgttgtctg cctaccaaat cgaacgcttc   1620

aatatccgct accgccccga cgagcaaaat gatccctaca cttgggcagt cggcggcaaa   1680

caccgttcgc gcggcgtgga attgtccgcc atcgggcaaa tcatccccaa aaaactctat   1740

ctgcgcggtt cgttgggcgt gatgcaggcg aaagtcgttg aagacaaaga aaatcccgac   1800

cgagtgggca tccatttgaa taacaccagc aacgttaccg gcaacctgtt tttccgttat   1860

accccgaccg aaaacctcta cggcgaaatc ggcgtaaccg gtacaggcaa acgctacggt   1920

tacaactcaa gaaataaaga agtgactacg cttccaggct ttgcccgagt tgatgccatg   1980

cttggctgga accataaaaa tgttaacatt acctttgccg cagccaatct gctcaatcaa   2040

aaatattggc gttcggatgc catgcccggc gcgccgcgca cttatacggc gcgggttaat   2100

tacagtttct aa                                                       2112
```

<210> SEQ ID NO 50
<211> LENGTH: 703
<212> TYPE: PRT
<213> ORGANISM: Neisseria meningitidis

<400> SEQUENCE: 50

```
Met Lys Ile Ser Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30

Thr Ala Thr Leu Pro Thr Val Ser Val Val Gly Gln Ser Asp Thr Ser
         35                  40                  45

Val Leu Lys Gly Tyr Ile Asn Tyr Asp Glu Ala Ala Val Thr Arg Asn
     50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                 85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Ala Val Tyr Gly Ser Trp Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
```

-continued

```
    210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

Asp Arg Ser Pro Thr Lys Ser Val Tyr Asp Arg Phe Gly Leu Pro Tyr
            260                 265                 270

Arg Met Gly Phe Ala His Arg Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300

Gln Trp Gln Leu Ala His Arg Thr Ala Ala Gln Asp Phe Asp His Phe
305                 310                 315                 320

Tyr Ala Gly Ser Glu Asn Gly Asn Leu Ile Lys Arg Asn Tyr Ala Trp
                325                 330                 335

Gln Gln Thr Asp Asn Lys Thr Leu Ser Ser Asn Phe Thr Leu Asn Gly
            340                 345                 350

Asp Tyr Thr Ile Gly Arg Phe Glu Asn His Leu Thr Val Gly Met Asp
        355                 360                 365

Tyr Ser Arg Glu His Arg Asn Pro Thr Leu Gly Tyr Ser Arg Ala Phe
    370                 375                 380

Thr Ala Ser Ile Asp Pro Tyr Asp Arg Ala Ser Trp Pro Ala Ser Gly
385                 390                 395                 400

Arg Leu Gln Pro Ile Leu Thr Gln Asn Arg His Lys Ala Asp Ser Tyr
                405                 410                 415

Gly Ile Phe Val Gln Asn Ile Phe Ser Ala Thr Pro Asp Leu Lys Phe
            420                 425                 430

Val Leu Gly Gly Arg Tyr Asp Lys Tyr Thr Phe Asn Ser Glu Asn Lys
        435                 440                 445

Leu Thr Gly Ser Ser Arg Gln Tyr Ser Gly His Ser Phe Ser Pro Asn
    450                 455                 460

Ile Gly Ala Val Trp Asn Ile Asn Pro Val His Thr Leu Tyr Ala Ser
465                 470                 475                 480

Tyr Asn Lys Gly Phe Ala Pro Tyr Gly Gly Arg Gly Gly Tyr Leu Ser
                485                 490                 495

Ile Asn Thr Ser Ser Ser Ala Val Phe Asn Ala Asp Pro Glu Tyr Thr
            500                 505                 510

Arg Gln Tyr Glu Thr Gly Val Lys Ser Ser Trp Leu Asp Asp Arg Leu
        515                 520                 525

Ser Thr Thr Leu Ser Ala Tyr Gln Ile Glu Arg Phe Asn Ile Arg Tyr
    530                 535                 540

Arg Pro Asp Glu Gln Asn Asp Pro Tyr Thr Trp Ala Val Gly Gly Lys
545                 550                 555                 560

His Arg Ser Arg Gly Val Glu Leu Ser Ala Ile Gly Gln Ile Ile Pro
                565                 570                 575

Lys Lys Leu Tyr Leu Arg Gly Ser Leu Gly Val Met Gln Ala Lys Val
            580                 585                 590

Val Glu Asp Lys Glu Asn Pro Asp Arg Val Gly Ile His Leu Asn Asn
        595                 600                 605

Thr Ser Asn Val Thr Gly Asn Leu Phe Phe Arg Tyr Thr Pro Thr Glu
    610                 615                 620

Asn Leu Tyr Gly Glu Ile Gly Val Thr Gly Thr Gly Lys Arg Tyr Gly
625                 630                 635                 640
```

-continued

```
Tyr Asn Ser Arg Asn Lys Glu Val Thr Thr Leu Pro Gly Phe Ala Arg
                645                 650                 655

Val Asp Ala Met Leu Gly Trp Asn His Lys Asn Val Asn Ile Thr Phe
            660                 665                 670

Ala Ala Ala Asn Leu Leu Asn Gln Lys Tyr Trp Arg Ser Asp Ala Met
        675                 680                 685

Pro Gly Ala Pro Arg Thr Tyr Thr Ala Arg Val Asn Tyr Ser Phe
    690                 695                 700


<210> SEQ ID NO 51
<211> LENGTH: 2112
<212> TYPE: DNA
<213> ORGANISM: Neisseria meningitidis

<400> SEQUENCE: 51

atgaaaatat catttcattt agctttatta cccacgctga ttattgcttc cttccctgtt      60

gctgccgccg atacgcagga caatggtgaa cattacaccg ccactctgcc caccgtttcc     120

gtggtcggac agtccgacac cagcgtactc aaaggctaca tcaactacga cgaagccgcc     180

gttacccgca acggacagct catcaaagaa acgccgcaaa ccatcgatac gctcaatatc     240

cagaaaaaca aaaattacgg tacgaacgat ttgagttcca tcctcgaagg caatgccggc     300

atcgacgctg cctacgatat gcgcggtgaa agcattttcc tgcgcggttt tcaagccgac     360

gcatccgata tttaccgcga cggcgtgcgc gaaagcggac aagtgcgccg cagtactgcc     420

aacatcgagc gcgtggaaat cctgaaaggc ccgtcttccg tgctttacgg ccgcaccaac     480

ggcggcggcg tcatcaacat ggtcagcaaa tacgccaact tcaaacaaag ccgcaacatc     540

ggagcggttt acggctcatg ggcaaaccgc agcctgaata tggacattaa cgaagtgctg     600

aacaaaaacg tcgccatccg tctcaccggc gaagtcgggc gcgccaattc gttccgcagc     660

ggcatagaca gcaaaaatgt catggtttcg cccagcatta ccgtcaaact cgacaacggc     720

ttgaagtgga cggggcaata cacctacgac aatgtggagc gcacgcccga ccgcagtccg     780

accaagtccg tgtacgaccg cttcggactg ccttaccgca tggggttcgc ccaccggaac     840

gattttgtca aagacaagct gcaagtttgg cgttccgacc ttgaatacgc cttcaacgac     900

aaatggcgtg cccaatggca gctcgcccac cgcacggcgg cgcaggattt tgatcatttc     960

tatgcaggca gcgaaaatgg caacttaatc aaacgtaact acgcctggca gcagaccgac    1020

aacaaaaccc tgtcgtccaa cttaacgctc aacggcgact acaccatcgg ccgttttgaa    1080

aaccacctga ccgtaggcat ggattacagc cgcgaacacc gcaacccgac attgggtttc    1140

agcagcgcct tttccgcctc catcaacccc tacgaccgcg caagctggcc ggcttcgggc    1200

agattgcagc ctattctgac ccaaaaccgc cacaaagccg actcctacgg catctttgtg    1260

caaaacatct tctccgccac gcccgatttg aaattcgtcc tcggcggccg ttacgacaaa    1320

tacacccttta attccgaaaa caaactcacc ggcagcagcc gccaatacag cggacactcg    1380

ttcagcccca acatcggcgc agtgtggaac atcaatcccg tccacacact ttacgcctcg    1440

tataacaaag gcttcgcgcc ttatggcgga cgcggcggct atttgagcat cgatacgttg    1500

tcttccgccg tgttcaacgc cgaccccgag tacacccgcc aatacgaaac cggcgtgaaa    1560

agcagttggc tggacgaccg cctcagcact acgttgtctg cctaccaaat cgaacgcttc    1620

aatatccgct accgccccga tccaaaaaac aacccttata tttatgcggt tagcggcaaa    1680

caccgttcgc gcggcgtgga attgtccgcc atcgggcaaa tcatccccaa aaaactctat    1740
```

-continued

```
ctgcgcggtt cgttgggcgt gatgcaggcg aaagtcgttg aagacaaaga aaatcccgac   1800

cgagtgggca tccatttgaa taataccagc aacgttaccg gcaacctgtt tttccgttat   1860

accccgaccg aaaacctcta cggcgaaatc ggcgtaaccg gtacaggcaa acgctacggt   1920

tacaactcaa gaaataaaga agtgactacg cttccaggct ttgcccgagt tgatgccatg   1980

cttggctgga accataaaaa tgttaacgtt acctttgccg cagccaatct gctcaatcaa   2040

aaatattggc gttcggactc tatgccgggt aatccgcgcg gctatactgc ccgggtaaat   2100

taccgtttct ga                                                       2112


<210> SEQ ID NO 52
<211> LENGTH: 703
<212> TYPE: PRT
<213> ORGANISM: Neisseria meningitidis

<400> SEQUENCE: 52

Met Lys Ile Ser Phe His Leu Ala Leu Leu Pro Thr Leu Ile Ile Ala
  1               5                  10                  15

Ser Phe Pro Val Ala Ala Ala Asp Thr Gln Asp Asn Gly Glu His Tyr
             20                  25                  30

Thr Ala Thr Leu Pro Thr Val Ser Val Val Gly Gln Ser Asp Thr Ser
         35                  40                  45

Val Leu Lys Gly Tyr Ile Asn Tyr Asp Glu Ala Ala Val Thr Arg Asn
     50                  55                  60

Gly Gln Leu Ile Lys Glu Thr Pro Gln Thr Ile Asp Thr Leu Asn Ile
 65                  70                  75                  80

Gln Lys Asn Lys Asn Tyr Gly Thr Asn Asp Leu Ser Ser Ile Leu Glu
                 85                  90                  95

Gly Asn Ala Gly Ile Asp Ala Ala Tyr Asp Met Arg Gly Glu Ser Ile
            100                 105                 110

Phe Leu Arg Gly Phe Gln Ala Asp Ala Ser Asp Ile Tyr Arg Asp Gly
        115                 120                 125

Val Arg Glu Ser Gly Gln Val Arg Arg Ser Thr Ala Asn Ile Glu Arg
    130                 135                 140

Val Glu Ile Leu Lys Gly Pro Ser Ser Val Leu Tyr Gly Arg Thr Asn
145                 150                 155                 160

Gly Gly Gly Val Ile Asn Met Val Ser Lys Tyr Ala Asn Phe Lys Gln
                165                 170                 175

Ser Arg Asn Ile Gly Ala Val Tyr Gly Ser Trp Ala Asn Arg Ser Leu
            180                 185                 190

Asn Met Asp Ile Asn Glu Val Leu Asn Lys Asn Val Ala Ile Arg Leu
        195                 200                 205

Thr Gly Glu Val Gly Arg Ala Asn Ser Phe Arg Ser Gly Ile Asp Ser
    210                 215                 220

Lys Asn Val Met Val Ser Pro Ser Ile Thr Val Lys Leu Asp Asn Gly
225                 230                 235                 240

Leu Lys Trp Thr Gly Gln Tyr Thr Tyr Asp Asn Val Glu Arg Thr Pro
                245                 250                 255

9Asp Arg Ser Pro Thr Lys Ser Val Tyr Asp Arg Phe Gly Leu Pro Tyr
            260                 265                 270
A
rg Met Gly Phe Ala His Arg Asn Asp Phe Val Lys Asp Lys Leu Gln
        275                 280                 285

Val Trp Arg Ser Asp Leu Glu Tyr Ala Phe Asn Asp Lys Trp Arg Ala
    290                 295                 300
```

-continued

Gln Trp Gln Leu Ala His Arg Thr Ala Ala Gln Asp Phe Asp His Phe
305 310 315 320

Tyr Ala Gly Ser Glu Asn Gly Asn Leu Ile Lys Arg Asn Tyr Ala Trp
325 330 335

Gln Gln Thr Asp Asn Lys Thr Leu Ser Ser Asn Leu Thr Leu Asn Gly
340 345 350

Asp Tyr Thr Ile Gly Arg Phe Glu Asn His Leu Thr Val Gly Met Asp
355 360 365

Tyr Ser Arg Glu His Arg Asn Pro Thr Leu Gly Phe Ser Ser Ala Phe
370 375 380

Ser Ala Ser Ile Asn Pro Tyr Asp Arg Ala Ser Trp Pro Ala Ser Gly
385 390 395 400

Arg Leu Gln Pro Ile Leu Thr Gln Asn Arg His Lys Ala Asp Ser Tyr
405 410 415

Gly Ile Phe Val Gln Asn Ile Phe Ser Ala Thr Pro Asp Leu Lys Phe
420 425 430

Val Leu Gly Gly Arg Tyr Asp Lys Tyr Thr Phe Asn Ser Glu Asn Lys
435 440 445

Leu Thr Gly Ser Ser Arg Gln Tyr Ser Gly His Ser Phe Ser Pro Asn
450 455 460

Ile Gly Ala Val Trp Asn Ile Asn Pro Val His Thr Leu Tyr Ala Ser
465 470 475 480

Tyr Asn Lys Gly Phe Ala Pro Tyr Gly Gly Arg Gly Gly Tyr Leu Ser
485 490 495

Ile Asp Thr Leu Ser Ser Ala Val Phe Asn Ala Asp Pro Glu Tyr Thr
500 505 510

Arg Gln Tyr Glu Thr Gly Val Lys Ser Ser Trp Leu Asp Asp Arg Leu
515 520 525

Ser Thr Thr Leu Ser Ala Tyr Gln Ile Glu Arg Phe Asn Ile Arg Tyr
530 535 540

Arg Pro Asp Pro Lys Asn Asn Pro Tyr Ile Tyr Ala Val Ser Gly Lys
545 550 555 560

His Arg Ser Arg Gly Val Glu Leu Ser Ala Ile Gly Gln Ile Ile Pro
565 570 575

Lys Lys Leu Tyr Leu Arg Gly Ser Leu Gly Val Met Gln Ala Lys Val
580 585 590

Val Glu Asp Lys Glu Asn Pro Asp Arg Val Gly Ile His Leu Asn Asn
595 600 605

Thr Ser Asn Val Thr Gly Asn Leu Phe Phe Arg Tyr Thr Pro Thr Glu
610 615 620

Asn Leu Tyr Gly Glu Ile Gly Val Thr Gly Thr Gly Lys Arg Tyr Gly
625 630 635 640

Tyr Asn Ser Arg Asn Lys Glu Val Thr Thr Leu Pro Gly Phe Ala Arg
645 650 655

Val Asp Ala Met Leu Gly Trp Asn His Lys Asn Val Asn Val Thr Phe
660 665 670

Ala Ala Ala Asn Leu Leu Asn Gln Lys Tyr Trp Arg Ser Asp Ser Met
675 680 685

Pro Gly Asn Pro Arg Gly Tyr Thr Ala Arg Val Asn Tyr Arg Phe
690 695 700

<210> SEQ ID NO 53
<211> LENGTH: 693
<212> TYPE: DNA

-continued

<213> ORGANISM: Neisseria meningitidis

<400> SEQUENCE: 53

```
atgaaacgct tcacctatac tctttccgac ggcttgtgca tcgaaatcga actcaaacgc     60
agtgccaaga aaaatctgat tctgcgcccc gtcaatatgc agacggtcag catcaacgtc    120
ccaccctttt ttcaagacca cgcgttagca aactggctgg cggcaaacga aacgattttg    180
cggaacacgc ttgctaaaat gcccgtgcat cctgtttccc acccaaactt acccgagtgg    240
atttggtatc ggggaataaa gaccaagctg gatacccaca gccaaagcca tatccgtatc    300
acgtcgtctg aaatcctgct tccccgaaaa gaaaccgccg cacaaatcga ccacctgcgc    360
cgcctgttga acgaacgcgc ccgcgaatac ctgctgcccc gccttgaaaa acacgcagcc    420
gaaacaggac tgactcccgc tgccacagac ctgagcaacg ccaaaacctt ttggggcgta    480
tgccgcccgc acaccggcat ccgcctcaac tggcggctga tcggcacgcc cgaatacgtc    540
gccgactatg tctgcatcca cgaactctgc cacctccgcc accccgacca cagtccgcgc    600
ttttggcatt tggtgaacac gctgacgccg cataccgaca atgctaaaag ttggctgaag    660
gcgcacgggc gggaattgtt tgtgctgggg taa                                  693
```

<210> SEQ ID NO 54
<211> LENGTH: 230
<212> TYPE: PRT
<213> ORGANISM: Neisseria meningitidis

<400> SEQUENCE: 54

```
Met Lys Arg Phe Thr Tyr Thr Leu Ser Asp Gly Leu Cys Ile Glu Ile
1               5                   10                  15

Glu Leu Lys Arg Ser Ala Lys Lys Asn Leu Ile Leu Arg Pro Val Asn
            20                  25                  30

Met Gln Thr Val Ser Ile Asn Val Pro Pro Phe Phe Gln Asp His Ala
        35                  40                  45

Leu Ala Asn Trp Leu Ala Ala Asn Glu Thr Ile Leu Arg Asn Thr Leu
    50                  55                  60

Ala Lys Met Pro Val His Pro Val Ser His Pro Asn Leu Pro Glu Trp
65                  70                  75                  80

Ile Trp Tyr Arg Gly Ile Lys Thr Lys Leu Asp Thr His Ser Gln Ser
                85                  90                  95

His Ile Arg Ile Thr Ser Ser Glu Ile Leu Leu Pro Arg Lys Glu Thr
            100                 105                 110

Ala Ala Gln Ile Asp His Leu Arg Arg Leu Leu Asn Glu Arg Ala Arg
        115                 120                 125

Glu Tyr Leu Leu Pro Arg Leu Glu Lys His Ala Ala Glu Thr Gly Leu
    130                 135                 140

Thr Pro Ala Ala Thr Asp Leu Ser Asn Ala Lys Thr Phe Trp Gly Val
145                 150                 155                 160

Cys Arg Pro His Thr Gly Ile Arg Leu Asn Trp Arg Leu Ile Gly Thr
                165                 170                 175

Pro Glu Tyr Val Ala Asp Tyr Val Cys Ile His Glu Leu Cys His Leu
            180                 185                 190

Arg His Pro Asp His Ser Pro Arg Phe Trp His Leu Val Asn Thr Leu
        195                 200                 205

Thr Pro His Thr Asp Asn Ala Lys Ser Trp Leu Lys Ala His Gly Arg
    210                 215                 220

Glu Leu Phe Val Leu Gly
```

-continued 225 230

<210> SEQ ID NO 55
<211> LENGTH: 546
<212> TYPE: DNA
<213> ORGANISM: Neisseria meningitidis

<400> SEQUENCE: 55
atgagcaaga ttattgtgct gaccgcaggc cacagcaaca ccgacccggg tgcggtcaac 60
ggaagcgacc gtgaggcgga cttggcgcag gatatgcgca acattgtggc ttcaatcctg 120
cgtaacgatt acggcctgac cgttaaaacc gacggcacgg gcaaaggcaa tatgccgctg 180
cgcgaagcgg tcaagctgat tcgcggctcg gatgtggcga ttgagtttca caccaacgct 240
gccgtcagca aagcggcgac aggcatcgaa gccttgagta ccgttaaaaa caaacgctgg 300
tgtcaggtgt tgagcaaagc cgttgccaag aaaaccggct ggaaactgcg cggcgaagac 360
ggctttaaac ccgacaatgc gggccagcat tcgcgcctgg cttatgcaca agccggcggc 420
attgtgtttg agcctttttt catcagcaac gacactgatt tggccttgtt taagacgact 480
aaatggggca tctgccgcgc gattgcggac gcgattgcga tggaattggg ggcggcaaga 540
gtatga 546

<210> SEQ ID NO 56
<211> LENGTH: 181
<212> TYPE: PRT
<213> ORGANISM: Neisseria meningitidis

<400> SEQUENCE: 56

Met Ser Lys Ile Ile Val Leu Thr Ala Gly His Ser Asn Thr Asp Pro
1 5 10 15

Gly Ala Val Asn Gly Ser Asp Arg Glu Ala Asp Leu Ala Gln Asp Met
20 25 30

Arg Asn Ile Val Ala Ser Ile Leu Arg Asn Asp Tyr Gly Leu Thr Val
35 40 45

Lys Thr Asp Gly Thr Gly Lys Gly Asn Met Pro Leu Arg Glu Ala Val
50 55 60

Lys Leu Ile Arg Gly Ser Asp Val Ala Ile Glu Phe His Thr Asn Ala
65 70 75 80

Ala Val Ser Lys Ala Ala Thr Gly Ile Glu Ala Leu Ser Thr Val Lys
85 90 95

Asn Lys Arg Trp Cys Gln Val Leu Ser Lys Ala Val Ala Lys Lys Thr
100 105 110

Gly Trp Lys Leu Arg Gly Glu Asp Gly Phe Lys Pro Asp Asn Ala Gly
115 120 125

Gln His Ser Arg Leu Ala Tyr Ala Gln Ala Gly Gly Ile Val Phe Glu
130 135 140

Pro Phe Phe Ile Ser Asn Asp Thr Asp Leu Ala Leu Phe Lys Thr Thr
145 150 155 160

Lys Trp Gly Ile Cys Arg Ala Ile Ala Asp Ala Ile Ala Met Glu Leu
165 170 175

Gly Ala Ala Arg Val
180

<210> SEQ ID NO 57
<211> LENGTH: 237
<212> TYPE: DNA
<213> ORGANISM: Neisseria meningitidis -continued

<400> SEQUENCE: 57

```
atgcgtattt tggatatttt taaaaaccca gcgacaggca atgtgtcgca ctcgaaactg     60

tgggcaaacg ttgcctgcgc ggcggggacg gttaagtttg tgatgctgcc cgacccgtcg    120

gcggagattt gggcggtgta tttgggcatt gtcggcggct atgcggtggc gcgttcgttg    180

gtcagcgtca aacgtcagga ggtcgagaat gaatctcgtg aaactgctgg cgaataa       237
```

<210> SEQ ID NO 58
<211> LENGTH: 78
<212> TYPE: PRT
<213> ORGANISM: Neisseria meningitidis

<400> SEQUENCE: 58

```
Met Arg Ile Leu Asp Ile Phe Lys Asn Pro Ala Thr Gly Asn Val Ser
  1               5                  10                  15

His Ser Lys Leu Trp Ala Asn Val Ala Cys Ala Ala Gly Thr Val Lys
             20                  25                  30

Phe Val Met Leu Pro Asp Pro Ser Ala Glu Ile Trp Ala Val Tyr Leu
         35                  40                  45

Gly Ile Val Gly Gly Tyr Ala Val Ala Arg Ser Leu Val Ser Val Lys
     50                  55                  60

Arg Gln Glu Val Glu Asn Glu Ser Arg Glu Thr Ala Gly Glu
 65                  70                  75
```

<210> SEQ ID NO 59
<211> LENGTH: 468
<212> TYPE: DNA
<213> ORGANISM: Neisseria meningitidis

<400> SEQUENCE: 59

```
atgcggtggc gcgttcgttg gtcagcgtca aacgtcagga ggtcgagaat gaatctcgtg     60

aaactgctgg cgaataactg gcaaccgatt gccatcatcg cgcttgtcgg cacgggtttg    120

gcggtgtcgc accatcaagg ctacaagtcg gcttttgcga agcagcaggc ggtcattgag    180

aaaatgaagc gcgacaaggc gcaagccctg ctgttgtcgg ctcaaaacta cgcccgcgaa    240

ctggaacagg cgcgtgcgga agctaaaaaa tatgaagtca aggcgcacgc cgtcggcatg    300

gctttggcga aaaaacaggc ggaagtcagc cgtctgaaaa cggaaaataa aaaggaaatc    360

gaaaatgtcc ttactcaaga ccgtaaaaat gcaggcggcg gttgtattga cggctttggc    420

catcacggct tgcagctcta caagcgcgcc ctcggctacg gaaattaa                 468
```

<210> SEQ ID NO 60
<211> LENGTH: 155
<212> TYPE: PRT
<213> ORGANISM: Neisseria meningitidis

<400> SEQUENCE: 60

```
Met Arg Trp Arg Val Arg Trp Ser Ala Ser Asn Val Arg Arg Ser Arg
  1               5                  10                  15

Met Asn Leu Val Lys Leu Leu Ala Asn Asn Trp Gln Pro Ile Ala Ile
             20                  25                  30

Ile Ala Leu Val Gly Thr Gly Leu Ala Val Ser His His Gln Gly Tyr
         35                  40                  45

Lys Ser Ala Phe Ala Lys Gln Gln Ala Val Ile Glu Lys Met Lys Arg
     50                  55                  60

Asp Lys Ala Gln Ala Leu Leu Leu Ser Ala Gln Asn Tyr Ala Arg Glu
```

-continued

```
 65                  70                  75                  80

Leu Glu Gln Ala Arg Ala Glu Ala Lys Lys Tyr Glu Val Lys Ala His
                 85                  90                  95

Ala Val Gly Met Ala Leu Ala Lys Lys Gln Ala Glu Val Ser Arg Leu
            100                 105                 110

Lys Thr Glu Asn Lys Lys Glu Ile Glu Asn Val Leu Thr Gln Asp Arg
        115                 120                 125

Lys Asn Ala Gly Gly Gly Cys Ile Asp Gly Phe Gly His His Gly Leu
    130                 135                 140

Gln Leu Tyr Lys Arg Ala Leu Gly Tyr Gly Asn
145                 150                 155
```

<210> SEQ ID NO 61
<211> LENGTH: 306
<212> TYPE: DNA
<213> ORGANISM: Neisseria meningitidis

<400> SEQUENCE: 61

```
atgtccttac tcaagaccgt aaaaatgcag gcggcggttg tattgacggc tttggccatc     60

acggcttgca gctctacaag cgcgccctcg gctacggaaa ttaaggttgt cgaaaaggcg    120

gtcatgccga caccgcctgc cgcgttgatg gtcgcgccgg tgcgcccgaa tccgccgaaa    180

gacggcaaga cggccacgct gttggaacac gccgccgagt ttggcggcta tgttgccgaa    240

cttgaaaacc aaaatcaggc ttggcgcgac tgggcgggca atcactcccg caaagtcgga    300

aactga                                                               306
```

<210> SEQ ID NO 62
<211> LENGTH: 101
<212> TYPE: PRT
<213> ORGANISM: Neisseria meningitidis

<400> SEQUENCE: 62

```
Met Ser Leu Leu Lys Thr Val Lys Met Gln Ala Ala Val Val Leu Thr
  1               5                  10                  15

Ala Leu Ala Ile Thr Ala Cys Ser Ser Thr Ser Ala Pro Ser Ala Thr
             20                  25                  30

Glu Ile Lys Val Val Glu Lys Ala Val Met Pro Thr Pro Pro Ala Ala
         35                  40                  45

Leu Met Val Ala Pro Val Arg Pro Asn Pro Pro Lys Asp Gly Lys Thr
     50                  55                  60

Ala Thr Leu Leu Glu His Ala Ala Glu Phe Gly Gly Tyr Val Ala Glu
 65                  70                  75                  80

Leu Glu Asn Gln Asn Gln Ala Trp Arg Asp Trp Ala Gly Asn His Ser
                 85                  90                  95

Arg Lys Val Gly Asn
            100
```

<210> SEQ ID NO 63
<211> LENGTH: 348
<212> TYPE: DNA
<213> ORGANISM: Neisseria meningitidis

<400> SEQUENCE: 63

```
gtgctggcag ttttgcttgc tggtgtagcc ttcgccctga gcgatgattt catggttggc     60

tgctttcaaa cgccaacggt attcgccttt tgcgtcttta tagatttcaa aatacataag    120

gtttctccta tgaatgagta cacgttttct taccgcttta acggcaagtc ctggtcattg    180
```

-continued

```
agcatttggg cggacaaccc tgaagaagcc agggcgaaat ttcgggctgc acgagaaaat    240

gcgcactatg acggcgaagt tgtagcaaag gtttatacat ttgtaaatat ttcgtgggtt    300

aagaaattgt acaagcggac aaaatattta atgggtatca aagaatga                 348
```

<210> SEQ ID NO 64
<211> LENGTH: 115
<212> TYPE: PRT
<213> ORGANISM: Neisseria meningitidis

<400> SEQUENCE: 64

```
Val Leu Ala Val Leu Leu Ala Gly Val Ala Phe Ala Leu Ser Asp Asp
  1               5                  10                  15

Phe Met Val Gly Cys Phe Gln Thr Pro Thr Val Phe Ala Phe Cys Val
             20                  25                  30

Phe Ile Asp Phe Lys Ile His Lys Val Ser Pro Met Asn Glu Tyr Thr
         35                  40                  45

Phe Ser Tyr Arg Phe Asn Gly Lys Ser Trp Ser Leu Ser Ile Trp Ala
     50                  55                  60

Asp Asn Pro Glu Glu Ala Arg Ala Lys Phe Arg Ala Ala Arg Glu Asn
 65                  70                  75                  80

Ala His Tyr Asp Gly Glu Val Val Ala Lys Val Tyr Thr Phe Val Asn
                 85                  90                  95

Ile Ser Trp Val Lys Lys Leu Tyr Lys Arg Thr Lys Tyr Leu Met Gly
            100                 105                 110

Ile Lys Glu
        115
```

<210> SEQ ID NO 65
<211> LENGTH: 1404
<212> TYPE: DNA
<213> ORGANISM: Neisseria meningitidis

<400> SEQUENCE: 65

```
atgacattgc tcaatctaat gataatgcaa gattacggta tttccgtttg cctgacactg     60

acgccctatt tgcaacatga actattttcg gctatgaaat cctatttttc caaatatatc    120

ctacccgttt cactttttac cttgccacta tccctttccc catccgtttc ggcttttacg    180

ctgcctgaag catggcgggc ggcgcagcaa cattcggctg attttcaagc gtcccattac    240

cagcgtgatg cagtgcgcgc acggcaacaa caagccaagg ccgcattcct tccccatgta    300

tccgccaatg ccagctacca gcgccagccg ccatcgattt cttccacccg cgaaacacag    360

ggatggagcg tgcaggtggg acaaacctta tttgacgctg ccaaatttgc acaataccgc    420

caaagcaggt tcgatacgca ggctgcagaa cagcgtttcg atgcggcacg cgaagaattg    480

ctgttgaaag ttgccgaaag ttatttcaac gttttactca gccgagacac cgttgccgcc    540

catgcggcgg aaaaagaggc ttatgcccag caggtaaggc aggcgcaggc tttattcaat    600

aaaggtgctg ccaccgcgct ggatattcac gaagccaaag ccggttacga caatgccctg    660

gcccaagaaa tcgccgtatt ggctgagaaa caaacctatg aaaaccagtt gaacgactac    720

accggcctgg acagcaaaca aatcgaggcc atagataccg ccaacctgtt ggcacgctat    780

ctgcccaagc tggaacgtta cagtctggat gaatggcagc gcattgcctt atccaacaat    840

catgaatacc ggatgcagca gcttgccctg caaagcagcg gacaggcgct tcgggcagca    900

cagaacagcc gctatcccac cgtttctgcc catgtcggct atcagaataa cctctacact    960
```

-continued

```
tcatctgcgc agaataatga ctaccactat cggggcaaag ggatgagcgt cggcgtacag   1020

ttgaatttgc cgctttatac cggcggagaa ttgtcgggca aaatccatga agccgaagcg   1080

caatacgggg ctgccgaagc acagctgacc gcaaccgagc ggcacatcaa actcgccgta   1140

cgccaggctt ataccgaaag cggtgcggcg cgttaccaaa tcatggcgca agaacgggtt   1200

ttggaaagca gccgtttgaa actgaaatcg accgaaaccg gccaacaata cggcatccgc   1260

aaccggctgg aagtaatacg ggcgcggcag gaagtcgccc aagcagaaca gaaactggct   1320

caagcacggt ataaattcat gctggcttat ttgcgcttgg tgaaagagag cgggttaggg   1380

ttggaaacgg tatttgcgga ataa                                          1404


<210> SEQ ID NO 66
<211> LENGTH: 467
<212> TYPE: PRT
<213> ORGANISM: Neisseria meningitidis

<400> SEQUENCE: 66

Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
             20                  25                  30

Lys Ser Tyr Phe Ser Lys Tyr Ile Leu Pro Val Ser Leu Phe Thr Leu
         35                  40                  45

Pro Leu Ser Leu Ser Pro Ser Val Ser Ala Phe Thr Leu Pro Glu Ala
     50                  55                  60

Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Gly Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
```

-continued

```
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465


<210> SEQ ID NO 67
<211> LENGTH: 1404
<212> TYPE: DNA
<213> ORGANISM: Neisseria meningitidis

<400> SEQUENCE: 67

atgacattgc tcaatctaat gataatgcaa gattacggta tttccgtttg cctgacactg     60

acgccctatt tgcaacatga actattttcg gctatgaaat cctatttttc caaatatatc    120

ctacccgttt cactttttac cttgccacta tccctttccc catccgtttc ggcttttacg    180

ctgcctgaag catggcgggc ggcgcagcaa cattcggctg attttcaagc gtcccattac    240

cagcgtgatg cagtgcgcgc acggcaacaa caagccaagg ccgcattcct tccccatgta    300

tccgccaatg ccagctacca gcgccagccg ccatcgattt cttccacccg cgaaacacag    360

ggatggagcg tgcaggtggg acaaacctta tttgacgctg ccaaatttgc acaataccgc    420

caaagcaggt tcgatacgca ggctgcagaa cagcgtttcg atgcggcacg cgaagaattg    480

ctgttgaaag ttgccgaaag ttatttcaac gttttactca gccgagacac cgttgccgcc    540

catgcggcgg aaaaagaggc ttatgcccag caggtaaggc aggcgcaggc tttattcaat    600

aaaggtgctg ccaccgcgct ggatattcac gaagccaaag ccggttacga caatgccctg    660

gcccaagaaa tcgccgtatt ggctgagaaa caaacctatg aaaaccagtt gaacgactac    720

accggcctgg acagcaaaca aatcgaggcc atagataccg ccaacctgtt ggcacgctat    780

ctgcccaagc tggaacgtta cagtctggat gaatggcagc gcattgcctt atccaacaat    840

catgaatacc ggatgcagca gcttgccctg caaagcagcg gacaggcgct tcgggcagca    900

cagaacagcc gctatcccac cgtttctgcc catgtcggct atcagaataa cctctacact    960

tcatctgcgc agaataatga ctaccactat cggggcaaag ggatgagcgt cggcgtacag   1020

ttgaatttgc cgctttatac cggcggagaa ttgtcgggca aaatccatga agccgaagcg   1080
```

-continued

```
caatacgggg ctgccgaagc acagctgacc gcaaccgagc ggcacatcaa actcgccgta   1140

cgccaggctt ataccgaaag cggtgcggcg cgttaccaaa tcatggcgca agaacgggtt   1200

ttggaaagca gccgtttgaa actgaaatcg accgaaaccg gccaacaata cggcatccgc   1260

aaccggctgg aagtaatacg ggcgcggcag gaagtcgccc aagcagaaca gaaactggct   1320

caagcacggt ataaattcat gctggcttat ttgcgcttgg tgaaagagag cgggttaggg   1380

ttggaaacgg tatttgcgga ataa                                           1404
```

<210> SEQ ID NO 68
<211> LENGTH: 467
<212> TYPE: PRT
<213> ORGANISM: Neisseria meningitidis

<400> SEQUENCE: 68

```
Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
             20                  25                  30

Lys Ser Tyr Phe Ser Lys Tyr Ile Leu Pro Val Ser Leu Phe Thr Leu
         35                  40                  45

Pro Leu Ser Leu Ser Pro Ser Val Ser Ala Phe Thr Leu Pro Glu Ala
     50                  55                  60

Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Gly Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320
```

-continued

Ser Ser Ala Gln Asn Asn Asp Tyr His Tyr Arg Gly Lys Gly Met Ser
325 330 335

Val Gly Val Gln Leu Asn Leu Pro Leu Tyr Thr Gly Gly Glu Leu Ser
340 345 350

Gly Lys Ile His Glu Ala Glu Ala Gln Tyr Gly Ala Ala Glu Ala Gln
355 360 365

Leu Thr Ala Thr Glu Arg His Ile Lys Leu Ala Val Arg Gln Ala Tyr
370 375 380

Thr Glu Ser Gly Ala Ala Arg Tyr Gln Ile Met Ala Gln Glu Arg Val
385 390 395 400

Leu Glu Ser Ser Arg Leu Lys Leu Lys Ser Thr Glu Thr Gly Gln Gln
405 410 415

Tyr Gly Ile Arg Asn Arg Leu Glu Val Ile Arg Ala Arg Gln Glu Val
420 425 430

Ala Gln Ala Glu Gln Lys Leu Ala Gln Ala Arg Tyr Lys Phe Met Leu
435 440 445

Ala Tyr Leu Arg Leu Val Lys Glu Ser Gly Leu Gly Leu Glu Thr Val
450 455 460

Phe Ala Glu
465

<210> SEQ ID NO 69
<211> LENGTH: 1400
<212> TYPE: DNA
<213> ORGANISM: Neisseria meningitidis

<400> SEQUENCE: 69
atgacattgc tcaatctaat atgcaagatt acggtatttc cgtttgcctg acactgacgc 60
cctatttgca acatgaacta ttttcggcta tgaaatccta tttttccaaa tatatcctac 120
ccgtttcact ttttaccttg ccactatccc tttccccatc cgtttcggct tttacgctgc 180
ctgaagcatg gcgggcggcg cagcaacatt cggctgattt tcaagcgtcc cattaccagc 240
gtgatgcagt gcgcgcacgg caacaacaag ccaaggccgc attccttccc catgtatccg 300
ccaatgccag ctaccagcgc cagccgccat cgatttcttc cacccgcgaa acacagggat 360
ggagcgtgca ggtgggacaa accttatttg actctgccaa atttgcacaa taccgccaaa 420
gcaggttcga tacgcaggct gcagaacagc gtttcgatgc ggcacgcgaa gaattgctgt 480
tgaaagttgc cgaaagttat ttcaacgttt tactcagccg agacaccgtt gccgcccatg 540
cggcggaaaa agaggcttat gcccagcagg taaggcaggc gcaggcttta ttcaataaag 600
gtgctgccac cgcgctagat attcacgaag ccaaagccgg ttacgacaat gccctggccc 660
aagaaatcgc cgtattggct gagaaacaaa cctatgaaaa ccagttgaac gactacaccg 720
gcctggacag caaacaaatc gaggccatag ataccgccaa cctgttggca cgctatctgc 780
ccaagctgga acgttacagt ctggatgaat ggcagcgcat tgccttatcc aacaatcatg 840
aataccggat gcagcagctt gccctgcaaa gcagcggaca ggcgcttcgg gcagcacaga 900
acagccgcta tcccaccgtt tctgcccatg tcggctatca gaataacctc tacacttcat 960
ctgcgcagaa taatgactac cactatcggg gcaaagggat gagcgtcggc gtacagttga 1020
atttgccgct ttataccggc ggagaattgt cgggcaaaat ccatgaagcc gaagcgcaat 1080
acggggctgc cgaagcacag ctgaccgcaa ccgagcggca catcaaactc gccgtacgcc 1140
aggcttatac cgaaagcggt gcggcgcgtt accaaatcat ggcgcaagaa cgggttttgg 1200

-continued

```
aaagcagccg tttgaaactg aaatcgaccg aaaccggcca acaatacggc atccgcaacc   1260

ggctggaagt aatacgggcg cggcaggaag tcgcccaagc agaacagaaa ctggctcaag   1320

cacggtataa attcatgctg gcttatttgc gcttggtgaa agagagcggg ttagggttgg   1380

aaacggtatt tgcggaataa                                               1400


<210> SEQ ID NO 70
<211> LENGTH: 450
<212> TYPE: PRT
<213> ORGANISM: Neisseria meningitidis

<400> SEQUENCE: 70

Met Thr Leu Leu Asn Leu Ile Cys Lys Ile Thr Val Phe Pro Phe Ala
  1               5                  10                  15

His Arg Pro Ile Cys Asn Met Asn Tyr Phe Arg Leu Asn Pro Ile Phe
             20                  25                  30

Pro Asn Ile Ser Tyr Pro Phe His Phe Leu Pro Cys His Tyr Pro Phe
         35                  40                  45

Pro His Pro Phe Arg Leu Leu Arg Cys Leu Lys His Gly Gly Arg Arg
     50                  55                  60

Ser Asn Ile Arg Leu Ile Phe Lys Arg Pro Ile Thr Ser Val Met Gln
 65                  70                  75                  80

Cys Ala His Gly Asn Asn Lys Pro Arg Pro His Ser Phe Pro Met Tyr
                 85                  90                  95

Pro Pro Met Pro Ala Thr Ser Ala Ser Arg His Arg Phe Leu Pro Pro
            100                 105                 110

Ala Lys His Arg Asp Gly Ala Cys Arg Trp Asp Lys Pro Tyr Leu Thr
        115                 120                 125

Leu Pro Asn Leu His Asn Thr Ala Lys Ala Gly Ser Ile Arg Arg Leu
    130                 135                 140

Gln Asn Ser Val Ser Met Arg His Ala Lys Asn Cys Cys Lys Leu Pro
145                 150                 155                 160

Lys Val Ile Ser Thr Phe Tyr Ser Ala Glu Thr Pro Leu Pro Pro Met
                165                 170                 175

Arg Arg Lys Lys Arg Leu Met Pro Ser Arg Gly Arg Arg Arg Leu Tyr
            180                 185                 190

Ser Ile Lys Val Leu Pro Pro Arg Ile Phe Thr Lys Pro Lys Pro Val
        195                 200                 205

Thr Thr Met Pro Trp Pro Lys Lys Ser Pro Tyr Trp Leu Arg Asn Lys
    210                 215                 220

Pro Met Lys Thr Ser Thr Thr Thr Pro Ala Trp Thr Ala Asn Lys Ser
225                 230                 235                 240

Arg Pro Ile Pro Pro Thr Cys Trp His Ala Ile Cys Pro Ser Trp Asn
                245                 250                 255

Val Thr Val Trp Met Asn Gly Ser Ala Leu Pro Tyr Pro Thr Ile Met
            260                 265                 270

Asn Thr Gly Cys Ser Ser Leu Pro Cys Lys Ala Ala Asp Arg Arg Phe
        275                 280                 285

Gly Gln His Arg Thr Ala Ala Ile Pro Pro Phe Leu Pro Met Ser Ala
    290                 295                 300

Ile Arg Ile Thr Ser Thr Leu His Leu Arg Arg Ile Met Thr Thr Thr
305                 310                 315                 320

Ile Gly Ala Lys Gly Ala Ser Ala Tyr Ser Ile Cys Arg Phe Ile Pro
                325                 330                 335
```

-continued

```
Ala Glu Asn Cys Arg Ala Lys Ser Met Lys Pro Lys Arg Asn Thr Gly
            340                 345                 350

Leu Pro Lys His Ser Pro Gln Pro Ser Gly Thr Ser Asn Ser Pro Tyr
        355                 360                 365

Ala Arg Leu Ile Pro Lys Ala Val Arg Arg Val Thr Lys Ser Trp Arg
    370                 375                 380

Lys Asn Gly Phe Trp Lys Ala Ala Val Asn Asn Arg Pro Lys Pro Ala
385                 390                 395                 400

Asn Asn Thr Ala Ser Ala Thr Gly Trp Lys Tyr Gly Arg Gly Arg Lys
                405                 410                 415

Ser Pro Lys Gln Asn Arg Asn Trp Leu Lys His Gly Ile Asn Ser Cys
            420                 425                 430

Trp Leu Ile Cys Ala Trp Lys Arg Ala Gly Gly Trp Lys Arg Tyr Leu
        435                 440                 445

Arg Asn
    450
```

<210> SEQ ID NO 71
<211> LENGTH: 1404
<212> TYPE: DNA
<213> ORGANISM: Neisseria meningitidis

<400> SEQUENCE: 71

```
atgacattgc tcaatctaat gataatgcaa gattacggta tttccgtttg cctgacactg     60

acgccctatt tgcaacatga actattttcg gctatgaaat cctatttttc caaatatatc    120

ctacccgttt cactttttac cttgccacta tccctttccc catccgtttc ggcttttacg    180

ctgcctgaag catggcgggc ggcgcagcaa cattcggctg attttcaagc gtcccattac    240

cagcgtgatg cagtgcgcgc acggcaacaa caagccaagg ccgcattcct tccccatgta    300

tccgccaatg ccagctacca gcgccagccg ccatcgattt cttccacccg cgaaacacag    360

ggatggagcg tgcaggtggg acaaacctta tttgacgctg ccaaatttgc acaataccgc    420

caaagcaggt tcgatacgca ggctgcagaa cagcgtttcg atgcggcacg cgaagaattg    480

ctgttgaaag ttgccgaaag ttatttcaac gttttactca gccgagacac cgttgccgcc    540

catgcggcgg aaaaagaggc ttatgcccag caggtaaggc aggcgcaggc tttattcaat    600

aaaggtgctg ccaccgcgct ggatattcac gaagccaaag ccggttacga caatgccctg    660

gcccaagaaa tcgccgtatt ggctgagaaa caaacctatg aaaaccagtt gaacgactac    720

accgacctgg atagcaaaca aatcgaggcc atagataccg ccaacctgtt ggcacgctat    780

ctgcccaagc tggaacgtta cagtctggat gaatggcagc gcattgcctt atccaacaat    840

catgaatacc ggatgcagca gcttgccctg caaagcagcg gacaggcgct tcgggcagca    900

cagaacagcc gctatcccac cgtttctgcc catgtcggct atcagaataa cctctacact    960

tcatctgcgc agaataatga ctaccactat cggggcaaag ggatgagcgt cggcgtacag   1020

ttgaatttgc cgctttatac cggcggagaa ttgtcgggca aaatccatga agccgaagcg   1080

caatacgggg ccgccgaagc acagctgacc gcaaccgagc ggcacatcaa actcgccgta   1140

cgccaggctt ataccgaaag cggtgcggcg cgttaccaaa tcatggcgca agaacgggtt   1200

ttggaaagca gccgtttgaa actgaaatcg accgaaaccg gccaacaata cggcatccgc   1260

aaccggctgg aagtaatacg ggcgcggcag gaagtcgccc aagcagaaca gaaactggct   1320

caagcacggt ataaattcat gctggcttat ttgcgcttgg tgaaagagag cgggttaggg   1380

ttggaaacgg tatttgcgga ataa                                           1404
```

-continued

<210> SEQ ID NO 72
<211> LENGTH: 467
<212> TYPE: PRT
<213> ORGANISM: Neisseria meningitidis

<400> SEQUENCE: 72

```
Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
             20                  25                  30

Lys Ser Tyr Phe Ser Lys Tyr Ile Leu Pro Val Ser Leu Phe Thr Leu
         35                  40                  45

Pro Leu Ser Leu Ser Pro Ser Val Ser Ala Phe Thr Leu Pro Glu Ala
     50                  55                  60

Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
```

-continued

```
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465


<210> SEQ ID NO 73
<211> LENGTH: 1404
<212> TYPE: DNA
<213> ORGANISM: Neisseria meningitidis

<400> SEQUENCE: 73

atgacattgc tcaatctaat gataatgcaa gattacggta tttccgtttg cctgacactg     60

acgccctatt tgcaacatga actattttcg gctatgaaat cctatttttc caaatatatc    120

ctacccgttt cactttttac cttgccacta tccctttccc catccgtttc ggcttttacg    180

ctgcctgaag catggcgggc ggcgcagcaa cattcggctg attttcaagc gtcccattac    240

cagcgtgatg cagtgcgcgc acggcaacaa caagccaagg ccgcattcct tccccatgta    300

tccgccaatg ccagctacca gcgccagccg ccatcgattt cttccacccg cgaaacacag    360

ggatggagcg tgcaggtggg acaaacctta tttgacgctg ccaaatttgc acaataccgc    420

caaagcaggt tcgatacgca ggctgcagaa cagcgtttcg atgcggcacg cgaagaattg    480

ctgttgaaag ttgccgaaag ttatttcaac gttttactca gccgagacac cgttgccgcc    540

catgcggcgg aaaaagaggc ttatgcccag caggtaaggc aggcgcaggc tttattcaat    600

aaaggtgctg ccaccgcgct ggatattcac gaagccaaag ccggttacga caatgccctg    660

gcccaagaaa tcgccgtatt ggctgagaaa caaacctatg aaaaccagtt gaacgactac    720

accgacctgg atagcaaaca aatcgaggcc atagataccg ccaacctgtt ggcacgctat    780

ctgcccaagc tggaacgtta cagtctggat gaatggcagc gcattgcctt atccaacaat    840

catgaatacc ggatgcagca gcttgccctg caaagcagcg gacaggcgct tcgggcagca    900

cagaacagcc gctatcccac cgtttctgcc catgtcggct atcagaataa cctctacact    960

tcatctgcgc agaataatga ctaccactat cggggcaaag ggatgagcgt cggcgtacag   1020

ttgaatttgc cgctttatac cggcggagaa ttgtcgggca aaatccatga agccgaagcg   1080

caatacgggg ccgccgaagc acagctgacc gcaaccgagc ggcacatcaa actcgccgta   1140

cgccaggctt ataccgaaag cggtgcggcg cgttaccaaa tcatggcgca agaacgggtt   1200

ttggaaagca gccgtttgaa actgaaatcg accgaaaccg gccaacaata cggcatccgc   1260

aaccggctgg aagtaatacg ggcgcggcag gaagtcgccc aagcagaaca gaaactggct   1320

caagcacggt ataaattcat gctggcttat ttgcgcttgg tgaaagagag cgggttaggg   1380

ttggaaacgg tatttgcgga ataa                                          1404


<210> SEQ ID NO 74
<211> LENGTH: 467
```

-continued

```
<212> TYPE: PRT
<213> ORGANISM: Neisseria meningitidis

<400> SEQUENCE: 74

Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
             20                  25                  30

Lys Ser Tyr Phe Ser Lys Tyr Ile Leu Pro Val Ser Leu Phe Thr Leu
         35                  40                  45

Pro Leu Ser Leu Ser Pro Ser Val Ser Ala Phe Thr Leu Pro Glu Ala
     50                  55                  60

Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400
```

-continued

```
Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465
```

```
<210> SEQ ID NO 75
<211> LENGTH: 1404
<212> TYPE: DNA
<213> ORGANISM: Neisseria meningitidis

<400> SEQUENCE: 75

atgacattgc tcaatctaat gataatgcaa gattacggta tttccgtttg cctgacactg      60

acgccctatt tgcaacatga actattttcg gctatgaaat cctatttttc caaatatatc     120

ctacccgttt cactttttac cttgccacta tccctttccc catccgtttc ggcttttacg     180

ctgcctgaag catggcgggc ggcgcagcaa cattcggctg attttcaagc gtcccattac     240

cagcgtgatg cagtgcgcgc acggcaacaa caagccaagg ccgcattcct tccccatgta     300

tccgccaatg ccagctacca gcgccagccg ccatcgattt cttccacccg cgaaacacag     360

ggatggagcg tgcaggtggg acaaacctta tttgacgctg ccaaatttgc acaataccgc     420

caaagcaggt tcgatacgca ggctgcagaa cagcgtttcg atgcggcacg cgaagaattg     480

ctgttgaaag ttgccgaaag ttatttcaac gttttactca gccgagacac cgttgccgcc     540

catgcggcgg aaaaagaggc ttatgcccag caggtaaggc aggcgcaggc tttattcaat     600

aaaggtgctg ccaccgcgct ggatattcac gaagccaaag ccggttacga caatgccctg     660

gcccaagaaa tcgccgtatt ggctgagaaa caaacctatg aaaaccagtt gaacgactac     720

accgacctgg atagcaaaca aatcgaggcc atagataccg ccaacctgtt ggcacgctat     780

ctgcccaagc tggaacgtta cagtctggat gaatggcagc gcattgcctt atccaacaat     840

catgaatacc ggatgcagca gcttgccctg caaagcagcg gacaggcgct tcgggcagca     900

cagaacagcc gctatcccac cgtttctgcc catgtcggct atcagaataa cctctacact     960

tcatctgcgc agaataatga ctaccactat cggggcaaag ggatgagcgt cggcgtacag    1020

ttgaatttgc cgctttatac cggcggagaa ttgtcgggca aaatccatga agccgaagcg    1080

caatacgggg ccgccgaagc acagctgacc gcaaccgagc ggcacatcaa actcgccgta    1140

cgccaggctt ataccgaaag cggtgcggcg cgttaccaaa tcatggcgca agaacgggtt    1200

ttggaaagca gccgtttgaa actgaaatcg accgaaaccg gccaacaata cggcatccgc    1260

aaccggctgg aagtaatacg ggcgcggcag gaagtcgccc aagcagaaca gaaactggct    1320

caagcacggt ataaattcat gctggcttat ttgcgcttgg tgaaagagag cgggttaggg    1380

ttggaaacgg tatttgcgga ataa                                            1404

<210> SEQ ID NO 76
<211> LENGTH: 467
<212> TYPE: PRT
<213> ORGANISM: Neisseria meningitidis

<400> SEQUENCE: 76
```

-continued

```
Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
            20                  25                  30

Lys Ser Tyr Phe Ser Lys Tyr Ile Leu Pro Val Ser Leu Phe Thr Leu
        35                  40                  45

Pro Leu Ser Leu Ser Pro Ser Val Ser Ala Phe Thr Leu Pro Glu Ala
    50                  55                  60

Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415
```

-continued

```
Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465


<210> SEQ ID NO 77
<211> LENGTH: 1404
<212> TYPE: DNA
<213> ORGANISM: Neisseria meningitidis

<400> SEQUENCE: 77

atgacattgc tcaatctaat gataatgcaa gattacggta tttccgtttg cctgacactg     60

acgccctatt tgcaacatga actattttcg gctatgaaat cctatttttc caaatatatc    120

ctacccgttt cactttttac cttgccacta tccctttccc catccgtttc ggcttttacg    180

ctgcctgaag catggcgggc ggcgcagcaa cattcggctg attttcaagc gtcccattac    240

cagcgtgatg cagtgcgcgc acggcaacaa caagccaagg ccgcattcct tccccatgta    300

tccgccaatg ccagctacca gcgccagccg ccatcgattt cttccacccg cgaaacacag    360

ggatggagcg tgcaggtggg acaaacctta tttgacgctg ccaaatttgc acaataccgc    420

caaagcaggt tcgatacgca ggctgcagaa cagcgtttcg atgcggcacg cgaagaattg    480

ctgttgaaag ttgccgaaag ttatttcaac gttttactca gccgagacac cgttgccgcc    540

catgcggcgg aaaaagaggc ttatgcccag caggtaaggc aggcgcaggc tttattcaat    600

aaaggtgctg ccaccgcgct ggatattcac gaagccaaag ccggttacga caatgccctg    660

gcccaagaaa tcgccgtatt ggctgagaaa caaacctatg aaaaccagtt gaacgactac    720

accgacctgg atagcaaaca aatcgaggcc atagataccg ccaacctgtt ggcacgctat    780

ctgcccaagc tggaacgtta cagtctggat gaatggcagc gcattgcctt atccaacaat    840

catgaatacc ggatgcagca gcttgccctg caaagcagcg gacaggcgct tcgggcagca    900

cagaacagcc gctatcccac cgtttctgcc catgtcggct atcagaataa cctctacact    960

tcatctgcgc agaataatga ctaccactat cggggcaaag ggatgagcgt cggcgtacag   1020

ttgaatttgc cgctttatac cggcggagaa ttgtcgggca aaatccatga agccgaagcg   1080

caatacgggg ccgccgaagc acagctgacc gcaaccgagc ggcacatcaa actcgccgta   1140

cgccaggctt ataccgaaag cggtgcggcg cgttaccaaa tcatggcgca agaacgggtt   1200

ttggaaagca gccgtttgaa actgaaatcg accgaaaccg gccaacaata cggcatccgc   1260

aaccggctgg aagtaatacg ggcgcggcag gaagtcgccc aagcagaaca gaaactggct   1320

caagcacggt ataaattcat gctggcttat ttgcgcttgg tgaaagagag cgggttaggg   1380

ttggaaacgg tatttgcgga ataa                                          1404


<210> SEQ ID NO 78
<211> LENGTH: 467
<212> TYPE: PRT
<213> ORGANISM: Neisseria meningitidis

<400> SEQUENCE: 78

Met Thr Leu Leu Asn Leu Met Ile Met Gln Asp Tyr Gly Ile Ser Val
  1               5                  10                  15
```

-continued

```
Cys Leu Thr Leu Thr Pro Tyr Leu Gln His Glu Leu Phe Ser Ala Met
            20                  25                  30

Lys Ser Tyr Phe Ser Lys Tyr Ile Leu Pro Val Ser Leu Phe Thr Leu
        35                  40                  45

Pro Leu Ser Leu Ser Pro Ser Val Ser Ala Phe Thr Leu Pro Glu Ala
    50                  55                  60

Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
```

-continued

```
        435                 440                 445

Ala Tyr Leu Arg Leu Val Lys Glu Ser Gly Leu Gly Leu Glu Thr Val
    450                 455                 460

Phe Ala Glu
465


<210> SEQ ID NO 79
<211> LENGTH: 1404
<212> TYPE: DNA
<213> ORGANISM: Neisseria meningitidis

<400> SEQUENCE: 79

atgacattgc tcaatctaat gataatgcaa gattacggta tttccgtttg cctgacactg      60

acgccctatt tgcaacatga actattttcg gctatgaaat cctatttttc caaatatatc     120

ctacccgttt cactttttac cttgccacta tccctttccc catccgtttc ggcttttacg     180

ctgcctgaag catggcgggc ggcgcagcaa cattcggctg attttcaagc gtcccattac     240

cagcgtgatg cagtgcgcgc acggcaacaa caagccaagg ccgcattcct tccccatgta     300

tccgccaatg ccagctacca gcgccagccg ccatcgattt cttccacccg cgaaacacag     360

ggatggagcg tgcaggtggg acaaacctta tttgacgctg ccaaatttgc acaataccgc     420

caaagcaggt tcgatacgca ggctgcagaa cagcgtttcg atgcggcacg cgaagaattg     480

ctgttgaaag ttgccgaaag ttatttcaac gttttactca gccgagacac cgttgccgcc     540

catgcggcgg aaaaagaggc ttatgcccag caggtaaggc aggcgcaggc tttattcaat     600

aaaggtgctg ccaccgcgct ggatattcac gaagccaaag ccggttacga caatgccctg     660

gcccaagaaa tcgccgtatt ggctgagaaa caaacctatg aaaaccagtt gaacgactac     720

accgacctgg atagcaaaca aatcgaggcc atagataccg ccaacctgtt ggcacgctat     780

ctgcccaagc tggaacgtta cagtctggat gaatggcagc gcattgcctt atccaacaat     840

catgaatacc ggatgcagca gcttgccctg caaagcagcg gacaggcgct tcgggcagca     900

cagaacagcc gctatcccac cgtttctgcc catgtcggct atcagaataa cctctacact     960

tcatctgcgc agaataatga ctaccactat cggggcaaag ggatgagcgt cggcgtacag    1020

ttgaatttgc cgctttatac cggcggagaa ttgtcgggca aaatccatga agccgaagcg    1080

caatacgggg ccgccgaagc acagctgacc gcaaccgagc ggcacatcaa actcgccgta    1140

cgccaggctt ataccgaaag cggtgcggcg cgttaccaaa tcatggcgca agaacgggtt    1200

ttggaaagca gccgtttgaa actgaaatcg accgaaaccg gccaacaata cggcatccgc    1260

aaccggctgg aagtaatacg ggcgcggcag gaagtcgccc aagcagaaca gaaactggct    1320

caagcacggt ataaattcat gctggcttat ttgcgcttgg tgaaagagag cgggttaggg    1380

ttggaaacgg tatttgcgga ataa                                            1404


<210> SEQ ID NO 80
<211> LENGTH: 467
<212> TYPE: PRT
<213> ORGANISM: Neisseria meningitidis

<400> SEQUENCE: 80

Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
             20                  25                  30

Lys Ser Tyr Phe Ser Lys Tyr Ile Leu Pro Val Ser Leu Phe Thr Leu
```

-continued

```
        35                  40                  45

Pro Leu Ser Leu Ser Pro Ser Val Ser Ala Phe Thr Leu Pro Glu Ala
    50                  55                  60

Trp Arg Ala Ala Gln Gln His Ser Ala Asp Phe Gln Ala Ser His Tyr
65                  70                  75                  80

Gln Arg Asp Ala Val Arg Ala Arg Gln Gln Gln Ala Lys Ala Ala Phe
                85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460
```

-continued

Phe Ala Glu
465

<210> SEQ ID NO 81
<211> LENGTH: 1404
<212> TYPE: DNA
<213> ORGANISM: Neisseria meningitidis

<400> SEQUENCE: 81
atgacattgc tcaatctaat gataatgcaa gattacggta tttccgtttg cctgacactg 60
acgccctatt tgcaacatga actattttcg gctatgaaat cctatttttc caaatatatc 120
ctacccgttt cactttttac cttgccacta tccctttccc catccgtttc ggcttttacg 180
ctgcctgaag catggcgggc ggcgcagcaa cattcggctg attttcaagc gtcccattac 240
cagcgtgatg cagtgcgcgc acggcaacaa caagccaagg ccgcattcct tccccatgta 300
tccgccaatg ccagctacca gcgccagccg ccatcgattt cttccacccg cgaaacacag 360
ggatggagcg tgcaggtggg acaaacctta tttgacgctg ccaaatttgc acaataccgc 420
caaagcaggt tcgatacgca ggctgcagaa cagcgtttcg atgcggcacg cgaagaattg 480
ctgttgaaag ttgccgaaag ttatttcaac gttttactca gccgagacac cgttgccgcc 540
catgcggcgg aaaaagaggc ttatgcccag caggtaaggc aggcgcaggc tttattcaat 600
aaaggtgctg ccaccgcgct ggatattcac gaagccaaag ccggttacga caatgccctg 660
gcccaagaaa tcgccgtatt ggctgagaaa caaacctatg aaaaccagtt gaacgactac 720
accgacctgg atagcaaaca aatcgaggcc atagataccg ccaacctgtt ggcacgctat 780
ctgcccaagc tggaacgtta cagtctggat gaatggcagc gcattgcctt atccaacaat 840
catgaatacc ggatgcagca gcttgccctg caaagcagcg gacaggcgct tcgggcagca 900
cagaacagcc gctatcccac cgtttctgcc catgtcggct atcagaataa cctctacact 960
tcatctgcgc agaataatga ctaccactat cggggcaaag ggatgagcgt cggcgtacag 1020
ttgaatttgc cgctttatac cggcggagaa ttgtcgggca aaatccatga agccgaagcg 1080
caatacgggg ccgccgaagc acagctgacc gcaaccgagc ggcacatcaa actcgccgta 1140
cgccaagctt ataccgaaag cggtgcggcg cgttaccaaa tcatggcgca agaacgggtt 1200
ttggaaagca gccgtttgaa actgaaatcg accgaaaccg gccaacaata cggcatccgc 1260
aaccggctgg aagtaatacg ggcgcggcag gaagtcgccc aagcagaaca gaaactggct 1320
caagcacggt ataaattcat gctggcttat ttgcgcttgg tgaaagagag cgggttaggg 1380
ttggaaacgg tatttgcgga ataa 1404

<210> SEQ ID NO 82
<211> LENGTH: 467
<212> TYPE: PRT
<213> ORGANISM: Neisseria meningitidis

<400> SEQUENCE: 82

Met Thr Leu Leu Asn Leu Met Ile Met Gln Asp Tyr Gly Ile Ser Val
1 5 10 15

Cys Leu Thr Leu Thr Pro Tyr Leu Gln His Glu Leu Phe Ser Ala Met
20 25 30

Lys Ser Tyr Phe Ser Lys Tyr Ile Leu Pro Val Ser Leu Phe Thr Leu
35 40 45

Pro Leu Ser Leu Ser Pro Ser Val Ser Ala Phe Thr Leu Pro Glu Ala
50 55 60

-continued

```
Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465
```

-continued

<210> SEQ ID NO 83
<211> LENGTH: 1404
<212> TYPE: DNA
<213> ORGANISM: Neisseria meningitidis

<400> SEQUENCE: 83

```
atgacattgc tcaatctaat gataatgcaa gattacggta tttccgtttg cctgacactg      60
acgccctatt tgcaacatga actattttcg gctatgaaat cctatttttc caaatatatc     120
ctacccgttt cactttttac cttgccacta tccctttccc catccgtttc ggcttttacg     180
ctgcctgaag catggcgggc ggcgcagcaa cattcggctg attttcaagc gtcccattac     240
cagcgtgatg cagtgcgcgc acggcaacaa caagccaagg ccgcattcct tccccatgta     300
tccgccaatg ccagctacca gcgccagccg ccatcgattt cttccacccg cgaaacacag     360
ggatggagcg tgcaggtggg acaaacctta tttgacgctg ccaaatttgc acaataccgc     420
caaagcaggt tcgatacgca ggctgcagaa cagcgtttcg atgcggcacg cgaagaattg     480
ctgttgaaag ttgccgaaag ttatttcaac gttttactca gccgagacac cgttgccgcc     540
catgcggcgg aaaaagaggc ttatgcccag caggtaaggc aggcgcaggc tttattcaat     600
aaaggtgctg ccaccgcgct ggatattcac gaagccaaag ccggttacga caatgccctg     660
gcccaagaaa tcgccgtatt ggctgagaaa caaacctatg aaaaccagtt gaacgactac     720
accgacctgg atagcaaaca aatcgaggcc atagataccg ccaacctgtt ggcacgctat     780
ctgcccaagc tggaacgtta cagtctggat gaatggcagc gcattgcctt atccaacaat     840
catgaatacc ggatgcagca gcttgccctg caaagcagcg gacaggcgct tcgggcagca     900
cagaacagcc gctatcccac cgtttctgcc catgtcggct atcagaataa cctctacact     960
tcatctgcgc agaataatga ctaccactat cggggcaaag ggatgagcgt cggcgtacag    1020
ttgaatttgc cgctttatac cggcggagaa ttgtcgggca aaatccatga agccgaagcg    1080
caatacgggg ccgccgaagc acagctgacc gcaaccgagc ggcacatcaa actcgccgta    1140
cgccaggctt ataccgaaag cggtgcggcg cgttaccaaa tcatggcgca agaacgggtt    1200
ttggaaagca gccgtttgaa actgaaatcg accgaaaccg gccaacaata cggcatccgc    1260
aaccggctgg aagtaatacg ggcgcggcag gaagtcgccc aagcagaaca gaaactggct    1320
caagcacggt ataaattcat gctggcttat ttgcgcttgg tgaaagagag cgggttaggg    1380
ttggaaacgg tatttgcgga ataa                                           1404
```

<210> SEQ ID NO 84
<211> LENGTH: 467
<212> TYPE: PRT
<213> ORGANISM: Neisseria meningitidis

<400> SEQUENCE: 84

```
Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
             20                  25                  30

Lys Ser Tyr Phe Ser Lys Tyr Ile Leu Pro Val Ser Leu Phe Thr Leu
         35                  40                  45

Pro Leu Ser Leu Ser Pro Ser Val Ser Ala Phe Thr Leu Pro Glu Ala
     50                  55                  60

Trp Arg Ala Ala Gln Gln His Ser Ala Asp Phe Gln Ala Ser His Tyr
 65                  70                  75                  80
```

-continued

```
Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465
```

<210> SEQ ID NO 85
<211> LENGTH: 1404
<212> TYPE: DNA

-continued

<213> ORGANISM: Neisseria meningitidis

<400> SEQUENCE: 85

```
atgacattgc tcaatctaat gataatgcaa gattacggta tttccgtttg cctgacactg     60
acgccctatt tgcaacatga actattttcg gctatgaaat cctatttttc caaatatatc    120
ctacccgttt cactttttac cttgccacta tccctttccc catccgtttc ggcttttacg    180
ctgcctgaag catggcgggc ggcgcagcaa cattcggctg attttcaagc gtcccattac    240
cagcgtgatg cagtgcgcgc acggcaacaa caagccaagg ccgcattcct tccccatgta    300
tccgccaatg ccagctacca gcgccagccg ccatcgattt cttccacccg cgaaacacag    360
ggatggagcg tgcaggtggg acaaacctta tttgacgctg ccaaatttgc acaataccgc    420
caaagcaggt tcgatacgca ggctgcagaa cagcgtttcg atgcggcacg cgaagaattg    480
ctgttgaaag ttgccgaaag ttatttcaac gttttactca gccgagacac cgttgccgcc    540
catgcggcgg aaaaagaggc ttatgcccag caggtaaggc aggcgcaggc tttattcaat    600
aaaggtgctg ccaccgcgct ggatattcac gaagccaaag ccggttacga caatgccctg    660
gcccaagaaa tcgccgtatt ggctgagaaa caaacctatg aaaaccagtt gaacgactac    720
accgacctgg atagcaaaca aatcgaggcc atagataccg ccaacctgtt ggcacgctat    780
ctgcccaagc tggaacgtta cagtctggat gaatggcagc gcattgcctt atccaacaat    840
catgaatacc ggatgcagca gcttgccctg caaagcagcg gacaggcgct tcgggcagca    900
cagaacagcc gctatcccac cgtttctgcc catgtcggct atcagaataa cctctacact    960
tcatctgcgc agaataatga ctaccactat cggggcaaag ggatgagcgt cggcgtacag   1020
ttgaatttgc cgctttatac cggcggagaa ttgtcgggca aaatccatga agccgaagcg   1080
caatacgggg ccgccgaagc acagctgacc gcaaccgagc ggcacatcaa actcgccgta   1140
cgccaggctt ataccgaaag cggtgcggcg cgttaccaaa tcatggcgca agaacgggtt   1200
ttggaaagca gccgtttgaa actgaaatcg accgaaaccg gccaacaata cggcatccgc   1260
aaccggctgg aagtaatacg ggcgcggcag gaagtcgccc aagcagaaca gaaactggct   1320
caagcacggt ataaattcat gctggcttat ttgcgcttgg tgaaagagag cgggttaggg   1380
ttggaaacgg tatttgcgga ataa                                            1404
```

<210> SEQ ID NO 86
<211> LENGTH: 467
<212> TYPE: PRT
<213> ORGANISM: Neisseria meningitidis

<400> SEQUENCE: 86

```
Met Thr Leu Leu Asn Leu Met Ile Met Gln Asp Tyr Gly Ile Ser Val
 1               5                  10                  15

Cys Leu Thr Leu Thr Pro Tyr Leu Gln His Glu Leu Phe Ser Ala Met
            20                  25                  30

Lys Ser Tyr Phe Ser Lys Tyr Ile Leu Pro Val Ser Leu Phe Thr Leu
        35                  40                  45

Pro Leu Ser Leu Ser Pro Ser Val Ser Ala Phe Thr Leu Pro Glu Ala
    50                  55                  60

Trp Arg Ala Ala Gln Gln His Ser Ala Asp Phe Gln Ala Ser His Tyr
65                  70                  75                  80

Gln Arg Asp Ala Val Arg Ala Arg Gln Gln Gln Ala Lys Ala Ala Phe
                85                  90                  95

Leu Pro His Val Ser Ala Asn Ala Ser Tyr Gln Arg Gln Pro Pro Ser
```

-continued

```
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465
```

<210> SEQ ID NO 87
<211> LENGTH: 1404
<212> TYPE: DNA
<213> ORGANISM: Neisseria meningitidis

<400> SEQUENCE: 87

-continued

```
atgacattgc tcaatctaat gataatgcaa gattacggta tttccgtttg cctgacactg      60

acgccctatt tgcaacatga actattttcg gctatgaaat cctatttttc caaatatatc     120

ctacccgttt cactttttac cttgccacta tccctttccc catccgtttc ggcttttacg     180

ctgcctgaag catggcgggc ggcgcagcaa cattcggctg attttcaagc gtcccattac     240

cagcgtgatg cagtgcgcgc acggcaacaa caagccaagg ccgcattcct tccccatgta     300

tccgccaatg ccagctacca gcgccagccg ccatcgattt cttccacccg cgaaacacag     360

ggatggagcg tgcaggtggg acaaacctta tttgacgctg ccaaatttgc acaataccgc     420

caaagcaggt tcgatacgca ggctgcagaa cagcgtttcg atgcggcacg cgaagaattg     480

ctgttgaaag ttgccgaaag ttatttcaac gttttactca gccgagacac cgttgccgcc     540

catgcggcgg aaaaagaggc ttatgcccag caggtaaggc aggcgcaggc tttattcaat     600

aaaggtgctg ccaccgcgct ggatattcac gaagccaaag ccggttacga caatgccctg     660

gcccaagaaa tcgccgtatt ggctgagaaa caaacctatg aaaaccagtt gaacgactac     720

accgacctgg atagcaaaca aatcgaggcc atagataccg ccaacctgtt ggcacgctat     780

ctgcccaagc tggaacgtta cagtctggat gaatggcagc gcattgcctt atccaacaat     840

catgaatacc ggatgcagca gcttgccctg caaagcagcg gacaggcgct tcgggcagca     900

cagaacagcc gctatcccac cgtttctgcc catgtcggct atcagaataa cctctacact     960

tcatctgcgc agaataatga ctaccactat cggggcaaag ggatgagcgt cggcgtacag    1020

ttgaatttgc cgctttatac cggcggagaa ttgtcgggca aaatccatga agccgaagcg    1080

caatacgggg ccgccgaagc acagctgacc gcaaccgagc ggcacatcaa actcgccgta    1140

cgccaggctt ataccgaaag cggtgcggcg cgttaccaaa tcatggcgca agaacgggtt    1200

ttggaaagca gccgtttgaa actgaaatcg accgaaaccg gccaacaata cggcatccgc    1260

aaccggctgg aagtaatacg ggcgcggcag gaagtcgccc aagcagaaca gaaactggct    1320

caagcacggt ataaattcat gctggcttat ttgcgcttgg tgaaagagag cgggttaggg    1380

ttggaaacgg tatttgcgga ataa                                           1404
```

```
<210> SEQ ID NO 88
<211> LENGTH: 467
<212> TYPE: PRT
<213> ORGANISM: Neisseria meningitidis

<400> SEQUENCE: 88

Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
             20                  25                  30

Lys Ser Tyr Phe Ser Lys Tyr Ile Leu Pro Val Ser Leu Phe Thr Leu
         35                  40                  45

Pro Leu Ser Leu Ser Pro Ser Val Ser Ala Phe Thr Leu Pro Glu Ala
     50                  55                  60

Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125
```

-continued

```
Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465
```

<210> SEQ ID NO 89
<211> LENGTH: 1404
<212> TYPE: DNA
<213> ORGANISM: Neisseria meningitidis

<400> SEQUENCE: 89

```
atgacattgc tcaatctaat gataatgcaa gattacggta tttccgtttg cctgacactg      60

acgccctatt tgcaacatga actattttcg gctatgaaat cctatttttc caaatatatc     120
```

-continued

```
ctacccgttt cactttttac cttgccacta tccctttccc catccgtttc ggcttttacg    180

ctgcctgaag catggcgggc ggcgcagcaa cattcggctg attttcaagc gtcccattac    240

cagcgtgatg cagtgcgcgc acggcaacaa caagccaagg ccgcattcct tccccatgta    300

tccgccaatg ccagctacca gcgccagccg ccatcgattt cttccacccg cgaaacacag    360

ggatggagcg tgcaggtggg acaaacctta tttgacgctg ccaaatttgc acaataccgc    420

caaagcaggt tcgatacgca ggctgcagaa cagcgtttcg atgcggcacg cgaagaattg    480

ctgttgaaag ttgccgaaag ttatttcaac gttttactca gccgagacac cgttgccgcc    540

catgcggcgg aaaaagaggc ttatgcccag caggtaaggc aggcgcaggc tttattcaat    600

aaaggtgctg ccaccgcgct ggatattcac gaagccaaag ccggttacga caatgccctg    660

gcccaagaaa tcgccgtatt ggctgagaaa caaacctatg aaaaccagtt gaacgactac    720

accgacctgg atagcaaaca aatcgaggcc atagataccg ccaacctgtt ggcacgctat    780

ctgcccaagc tggaacgtta cagtctggat gaatggcagc gcattgcctt atccaacaat    840

catgaatacc ggatgcagca gcttgccctg caaagcagcg gacaggcgct tcgggcagca    900

cagaacagcc gctatcccac cgtttctgcc catgtcggct atcagaataa cctctacact    960

tcatctgcgc agaataatga ctaccactat cggggcaaag ggatgagcgt cggcgtacag   1020

ttgaatttgc cgctttatac cggcggagaa ttgtcgggca aaatccatga agccgaagcg   1080

caatacgggg ccgccgaagc acagctgacc gcaaccgagc ggcacatcaa actcgccgta   1140

cgccaggctt ataccgaaag cggtgcggcg cgttaccaaa tcatggcgca agaacgggtt   1200

ttggaaagca gccgtttgaa actgaaatcg accgaaaccg gccaacaata cggcatccgc   1260

aaccggctgg aagtaatacg ggcgcggcag gaagtcgccc aagcagaaca gaaactggct   1320

caagcacggt ataaattcat gctggcttat ttgcgcttgg tgaaagagag cgggttaggg   1380

ttggaaacgg tatttgcgga ataa                                          1404
```

```
<210> SEQ ID NO 90
<211> LENGTH: 467
<212> TYPE: PRT
<213> ORGANISM: Neisseria meningitidis

<400> SEQUENCE: 90

Met Thr Leu Leu Asn Leu Met Ile Met Gln Asp Tyr Gly Ile Ser Val
  1               5                  10                  15

Cys Leu Thr Leu Thr Pro Tyr Leu Gln His Glu Leu Phe Ser Ala Met
             20                  25                  30

Lys Ser Tyr Phe Ser Lys Tyr Ile Leu Pro Val Ser Leu Phe Thr Leu
         35                  40                  45

Pro Leu Ser Leu Ser Pro Ser Val Ser Ala Phe Thr Leu Pro Glu Ala
     50                  55                  60

Trp Arg Ala Ala Gln Gln His Ser Ala Asp Phe Gln Ala Ser His Tyr
 65                  70                  75                  80

Gln Arg Asp Ala Val Arg Ala Arg Gln Gln Gln Ala Lys Ala Ala Phe
                 85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140
```

-continued

```
Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240

Thr Asp Leu Asp Ser Lys Gln Ile Glu Ala Ile Asp Thr Ala Asn Leu
                245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
        275                 280                 285

Ala Leu Gln Ser Ser Gly Gln Ala Leu Arg Ala Ala Gln Asn Ser Arg
    290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
                325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
        355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
                405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
        435                 440                 445

Ala Tyr Leu Arg Leu Val Lys Glu Ser Gly Leu Gly Leu Glu Thr Val
    450                 455                 460

Phe Ala Glu
465


<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 91

gaacatggat cccgtccaca cactttacg                                   29


<210> SEQ ID NO 92
<211> LENGTH: 30
<212> TYPE: DNA
```

-continued

<213> ORGANISM: Artificial Sequence
<220> FEATURE:
<223> OTHER INFORMATION: Description of Artificial Sequence:primer

<400> SEQUENCE: 92
gcggccgaat tccaacaggg tcaatgaagt 30

<210> SEQ ID NO 93
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 93
ctgttggaat tcggccgctt gtagcaaaca ggct 34

<210> SEQ ID NO 94
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 94
tagtacggta ccgattcact tggtgctt 28

<210> SEQ ID NO 95
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 95
gcttgtggta ccatatgagc aaacaggctg aaaccagt 38

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 96
tcaatcctcg agttgcggct ttttctgctc tt 32

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 97
gctttgactt cattgaccct gttggcattg gcc 33

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 98
tatccaccaa ctggtcaatc gtggtcatac cgg 33

-continued

<210> SEQ ID NO 99
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 99
ccacgctgat tattgcttcc ttccctgttg ctg 33

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 100
acccggcata gagtccgaac gccaatattt ttg 33

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 101
tgtttcccac ccaaacttac 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 102
gttcgtggat gcagacatag 20

<210> SEQ ID NO 103
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 103
gcctgacact gacgccctat ttgcaacatg aac 33

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 104
taccgtgctt gagccagttt ctgttctgct tgg 33

<210> SEQ ID NO 105
<211> LENGTH: 19
<212> TYPE: DNA
<213> ORGANISM: Artificial Sequence
<220> FEATURE:

-continued

<223> OTHER INFORMATION: Description of Artificial Sequence:primer

<400> SEQUENCE: 105
accgtgaggc ggacttggc 19

<210> SEQ ID NO 106
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 106
tggcccgcat tgtcgggttt aaagccgtct tcg 33

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 107
atttgcggag ggcgaactgg 20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 108
gcttcgcaaa agccgacttg 20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 109
ggcaaccgat tgccatcatc 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 110
tttccgtttt cagacggctg 20

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 111
aagaccgtaa aaatgcaggc g 21

-continued

```
<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 112

tttccgactt tgcgggagtg                                                   20


<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 113

ggttggctgc tttcaaacgc                                                   20


<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 114

attaaatatt ttgtccgctt gtac                                              24


<210> SEQ ID NO 115
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 115

aaagcacagc accatggttg cagtagccga aac                                    33


<210> SEQ ID NO 116
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 116

agtgtcttta gcctcaatta cagcagcact gcc                                    33
```

NEISSERIA MENINGITIDIS COMPOUNDS AND ANTI-INFECTION APPLICATIONS THEREOF

The present application is a divisional of U.S. application Ser. No. 10/030,740, filed Mar. 27, 2002 (abandoned), which is a U.S. national phase of international application PCT/EP00/06943, filed Jul. 5, 2000, which designated the U.S., the entire contents of each of which is hereby incorporated by reference.

FIELD OF THE INVENTION

This invention generally relates to novel *Neisseria meningitides* (Nm) compounds, and to their anti-Nm infection applications. It more particularly relates to polynucleotides, herein referred to as Nm polynucleotide(s), polypeptides encoded by them (referred to herein as Nm polypeptide(s)), recombinant materials and methods for their production. In another aspect, the invention relates to methods for using such Nm polypeptides and Nm polynucleotides in anti-Nm infection applications, such as diagnostic, prophylactic and therapeutic uses thereof including vaccines against Nm infections. In a further aspect, the invention relates to diagnostic assays for detecting an Nm infection.

BACKGROUND OF THE INVENTION

*Neisseria meningitidis* (meningococcus) is a Gram negative bacterium frequently isolated from the human upper respiratory tract. It occasionally causes invasive bacterial diseases such as bacteremia and meningitis. The incidence of meningococcal disease shows geographical seasonal and annual differences (Schwartz, B., Moore, P. S., Broome, C. V.; Clin. Microbiol. Rev. 2 (Supplement), S18-S24, 1989). Most disease in temperate countries is due to strains of serogroup B, and varies in incidence from 1-10/100,000/year total population sometimes reaching higher values (Kaczmarski, E. B. (1997), Commun. Dis. Rep. Rev. 7: R55-9, 1995; Scholten, R. J. P. M., Bijlmer, H. A., Poolman, J. T. et al. Clin. Infect. Dis. 16: 237-246, 1993; Cruz, C., Pavez, G., Aguilar, E., et al. Epidemiol. Infect 105: 119-126, 1990).

Epidemics dominated by serogroup A meningococci mostly in central Africa, are encountered, sometimes reaching levels up to 1000/100,000/year (Schwartz, B., Moore, P. S., Broome, C. V. Clin. Microbiol. Rev. 2 (Supplement), S18-S24, 1989). Nearly all cases as a whole of meningococcal disease are caused by serogroup A, B, C, W-135 and Y meningococci and a tetravalent A, C, W-135, Y polysaccharide vaccine is available (Armand, J., Arminjon, F., Mynard, M. C., Lafaix, C., J. Biol. Stand. 10: 335-339, 1982).

The polysaccharide vaccines are currently being improved by way of chemical conjugating them to carrier proteins (Lieberman, J. M., Chiu, S. S., Wong, V. K., et al. JAMA 275: 1499-1503, 1996).

A serogroup B vaccine is not available, since the B capsular polysaccharide was found to be nonimmunogenic, most likely because it shares structural similarity to host components (Wyle, F. A., Artenstein, M. S., Brandt, M. L. et al. J. Infect. Dis. 126: 514-522, 1972; Finne, J. M., Leinonen, M., Mäkelä, P. M. Lancet ii.: 355-357, 1983).

For many years efforts have been initiated and carried out to develop meningococcal outer membrane based vaccines (de Moraes, J. C., Perkins, B., Camargo, M. C. et al. Lancet 340: 1074-1078, 1992; Bjune, G., Hoiby, E. A. Gronnesby, J. K. et al. 338: 1093-1096, 1991). Such vaccines have demonstrated efficcacies from 57%-85% in older children (>4 years) and adolescents, but none of them has demonstrated no significant efficacies in younger children/adults. These efficacies were further restricted to certain defined Nm strains, i.e. to the strain used to make the vaccine, and to related strains (e.g. of same electrophoretic type), without providing an efficient protection against most of the existing Nm strains. Such vaccines does notably not provide an efficient protection against a wide range of Nm strains, such as every strain of at least one defined serogroup (such as serogroup B).

The frequency of *Neisseria meningitidis* infections has risen dramatically in the past few decades. This has been attributed to the emergence of multiply antibiotic resistant strains and an increasing population of people with weakened immune systems. It is no longer uncommon to isolate *Neisseria meningitidis* strains that are resistant to some or all of the standard antibiotics. This phenomenon has created an unmet medical need and demand for new anti-microbial agents, vaccines, drug screening methods, and diagnostic tests for this organism.

SUMMARY OF THE INVENTION

The present invention relates to *Neisseria meningitidis* (Nm) polynucleotides and polypeptides, recombinant materials and methods for their production. In another aspect, the invention relates to methods for using such Nm polypeptides and polynucleotides, including prevention and treatment of Nm-related diseases. In a further aspect, the invention relates to diagnostic assays for detecting Nm-related diseases and conditions associated with Nm infections, such as assays for detecting expression or activity of Nm polynucleotides or polypeptides.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to *Neisseria meningitidis* (Nm) polypeptides and polynucleotides as described in greater detail below. In particular, the invention relates to Nm polynucleotides which cover the Nm genetic diversity and which correspond to Nm polypeptides of the outer membrane and/or the periplasma of Nm, and to the corresponding Nm polypeptide.

By "a polynucleotide which covers the Nm genetic diversity", it is herein meant that when assaying Nm Z2491, said polynucleotide can be observed as corresponding to at least an ORF fraction of more than 250 nucleotides, advantageously more than 500 nucleotides, preferably more than 750 nucleotides, but most preferably as corresponding to a complete ORF, and that said ORF is present in more than 70%, preferably in more than 80%, and more preferably in more than 90% of the strans of a panel of Nm strains chosen according to the MLST standard (multilocus sequence typing : see e.g Maiden et al. 1998, Proc. Natl. Acad. Sci. 95: 3140-3145) of which teaching is herein incorporated by reference. By "a polynucleotide corresponding to an ORF fraction, or a complete ORF" as above-mentioned, it is herein meant that said polynucleotide shows with said ORF fraction, or complete ORF, a sequence homology which is superior to about 85%, preferably to about 90%, more preferably to about 95%, and most preferably is a 100% homologue to said ORF fraction sequence, or ORF sequence. Such a panel may comprise Nm strains chosen serogroup A Nm strains, serogroup B Nm strains, serogroup C Nm strains, serogroup W135 Nm strains, and/or serogroup Y Nm strains. An advantageous Nm panel e.g. comprises Nm strains of the A, B, C, and W135 serogroups.

The invention relates especially to Nm compounds having the nucleotide and amino acid sequences set out in SEQ ID NO:1 to SEQ NO:90 (odd SEQ ID numbers for polynucleotides, even SEQ ID numbers for polypeptides), and are also illustrated in FIGS. 1A to 45A-2 (polynucleotides), and in FIGS. 1B to 45B (polypeptides). It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

Means for assaying the presence or absence of a polynucleotide in a bacterial strain are well known techniques to the person skilled in the art and examples of such means comprise nucleic probe hybridization (see e.g. dot blot experiments in the below example 1). Said polynucleotide may correspond, or be part of a gene as well as, in certain Nm strains, to a pseudogene. Examples of such probes for said SEQ ID No: 1-90 products include probes obtained by PCR amplification using the primers recited as SEQ ID No: 97-116 and chromosomal DNA from Nm Z2491 as target DNA (see e.g. examples below and Table 2: SEQ ID No97 and No98 are nucleotidic forward and, respectively reverse primers for dsbA, SEQ ID No99 and No100 are nucleotidic forward and, respectively reverse primers for fhuA, SEQ ID No101 and No102 are nucleotidic forward and, respectively reverse primers for rni5, SEQ ID No103 and No104 are nucleotidic forward and, respectively reverse primers for tolC, SEQ ID No105 and No106 are nucleotidic forward and, respectively reverse primers for rth17, SEQ ID No107 and No108 are nucleotidic forward and, respectively reverse primers for rth18, SEQ ID No109 and No110 are nucleotidic forward and, respectively reverse primers for rth19, SEQ ID No111 and No112 are nucleotidic forward and, respectively reverse primers for rth20, SEQ ID No113 and No114 are nucleotidic forward and, respectively reverse primers for rth21, SEQ ID No115 and No116 are nucleotidic forward and, respectively reverse primers for fhaB). Appropriate PCR conditions for obtaining such probes with said primers and DNA template can be determined by the person skilled in the art; as an example, these conditions may be: 1 μg. $ml^{-1}$ of template DNA; reaction buffer (10 mM Tris-Cl, pH 8.0, 50 mM KCl, 1.5 mM MgCl2, 0.001% gelatin); dATP, dCTP, dGTP and dTTP (200 μM each); dimethylsulfoxide (5%); forward and reverse primers (100 nM each) and Taq polymerase; PCR incubation: 1 min at 94° C., 30 cycles of 1 min at 94° C., 1.5 min at 5° C. below the Tm of the oligonucleotide primers, and 2 min at 72° C. followed by incubation for 5 min at 72° C.

It is understood that sequences recited herein as corresponding to any of SEQ ID NO:1-90 represent an exemplification of one embodiment of the invention since those of ordinary skill in the art will recognize that these sequences correspond to those identified on a panel of Nm strains constituted of Nm Z2491, Nm Z3524, Nm Z3842, Nm Z4667, Nm Z4707, Nm Z5005, Nm Z6466, Nm Z7176, Nm Z4662, Nm Z6904, Nm Z4259, Nm Z4673, Nm Z4683 (see "examples" below) as Nm ORF, and that variant, but homologue, dsbA, fhaB, fhuA, rni5, rth17, rth18, rth19, rth20, rth21, tolC, sequences can be found in other Nm strains. Any appropriate technique can be implemented by the skilled person, e.g. sequencing the products which hibridize with said primers. Such variant sequences are thus encompassed by the present invention.

It is also understood that whereas the products of SEQ ID NO: 1-90 according to the invention are of first interest because of inter alia their Nm genetic diversity coverage, variant but homologue products which do not cover Nm genetic diversity on such a wide basis, can also be produced by the skilled person when desired This means that the polypeptides and polynucleotides of the invention are candidates of first interest for construction or obtention of variant but homologue products which cover only one Nm serogroup, such as serogroup B, or which cover some but not all serogroups, such as serogroups B and A. Simple screening and/or trial and error tests can provide such variant sequences without undue burden. Such variant sequences are thus encompassed by the present invention.

Polypeptides

In one aspect of the invention there are provided polypeptides of *Neisseria meningitidis* referred to herein as Nm polypeptides as well as biologically, diagnostically, prophylactically, clinically or therapeutically useful variants thereof and compositions comprising the same.

The present invention further provides for:

(a) an isolated polypeptide which comprises an amino acid sequence which has at least 70% identity, preferably at least 80% identity, more preferably at least 90% identity, yet more preferably at least 95% identity, most preferably at least 97-99% or exact identity, to that of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90;

(b) a polypeptide encoded by an isolated polynucleotide comprising a polynucleotide sequence which has at least 70% identity, preferably at least 80% identity, more preferably at least 90% identity, yet more preferably at least 95% identity, even more preferably at least 97-99% or exact identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91,over the entire length of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89 respectively;

(c) a polypeptide encoded by an isolated polynucleotide comprising a polynucleotide sequence encoding a polypeptide which has at least 70% identity, preferably at least 80% identity, more preferably at least 90% identity, yet more preferably at least 95% identity, even more preferably at least 97-99% or exact identity, to the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90.

The Nm polypeptide provided in SEQ ID NO: 2, 4, 6, 8, 10, 12, 14, 16, 18, 20, 22, 24, 26 are the DsbA polypeptides from *Neisseria meningitidis* strains Z2491; Z3524, Z3842, Z4667, Z4707, Z5005, Z6466, Z7176, Z4662, Z6904, Z4259, Z4673, Z4683 respectively.

The Nm polypeptide provided in SEQ ID NO: 28 is the polypeptide (348 aminoacids) corresponding to the 3' end fraction of FhaB from *Neisseria meningitidis* strains Z2491.

The Nm polypeptides provided in SEQ ID NO: 30, 32, 34, 36, 38, 40, 42, 44, 46, 48, 50, 52 are the FhuA polypeptides from *Neisseria meningitidis* strains Z2491, Z3524, Z3842, Z4259, Z4662; Z4667, Z4673, Z4683, Z4707, Z5005, Z6904, Z7176 respectively.

The Nm polypeptides provided in SEQ ID NO: 54 is the Rni5 polypeptide from *Neisseria meningitidis* strain Z2491.

The Nm polypeptides provided in SEQ ID NO: 56, 60, 62, 64 are the Rth17, respectively Rth18, Rth19, Rth20, Rth21 polypeptides from *Neisseria meningitidis* strain Z2491.

The Nm polypeptides provided in SEQ ID NO: 66, 68, 70, 72, 74, 76, 78, 80, 82, 84, 86, 88, 90 are the TolC polypeptides from *Neisseria meningitidis* strain Z2491, Z3524, Z4707, Z3842, Z4259, Z4662, Z4667, Z4673Z4683, Z5005, Z6466, Z6904, Z7176 respectively.

The Nm polypeptides of which ORF has some correspondance (i.e. significant hit in a computer program for sequence identity determination such as a standard BLAST program, see also the below "definitions" section), though with no significant sequence identity/similarly, with an previously described ORF in another bacteria species have been named according to this previously known ORF. This is particularly the case of DsbA, FhaB, FhuA, Rth17 and TolC (see the below "examples"). The Nm polypeptides of which ORF has no significant hit with any gene of known function have been named according to the region plus a sequential number. This is particularly the case of Rni5, Rth18, Rth19, Rth20, Rth21.

A source of said Nm strains is given in the below "examples".

The invention also provides an immunogenic fragment of a Nm polypeptide, that is a contiguous portion of the Nm polypeptide which has the same or substantially the same immunogenic activity as the polypeptide comprising the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90. That is to say, the fragment (if necessary when coupled to a carrier) is capable of raising an immune response which recognises the Nm polypeptide. Such an immunogenic fragment may include, for example, the Nm polypeptide lacking an N-terminal leader sequence, and/or a transmembrane domain and/or a C-terminal anchor domain In a preferred aspect the immunogenic fragment according to the invention comprises substantially all of the extracellular domain of a polypeptide which has at least 70% identity, preferably at least 80% identity, more preferably at least 90% identity, yet more preferably at least 95% identity, most preferably at least 97-99% identity, to that of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90.

A fragment is a polypeptide having an amino acid sequence that is entirely the same as part but not all of any amino acid sequence of any polypeptide of the invention. As with Nm polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, or an isolated polypeptide comprising an amino acid sequence having at least 15, 20, 30, 40, 50 or 100 contiguous amino acids truncated or deleted from the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5-10, 1-5, 1-3, 1-2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenzae virus, NS1 (hemagglutinin). Another fusion partner is the protein known as LYTA. Preferably the C terminal portion of the molecule is used. Lyta is derived from *Streptococcus pneumoniae* which synthesize an N-acetyl-L-alanine amidase, amidase LYTA, (coded by the lytA gene {Gene, 43 (1986) page 265-272}) an autolysin that specifically degrades certain bonds in the peptidoglycan backbone. The C-terminal domain of the LYTA protein is responsible for the affinity to the choline or to some choline analogues such as DEAE. This property has been exploited for the development of *E.coli* C-LYTA expressing plasmids useful for expression of fusion proteins. Purification of hybrid proteins containing the C-LYTA fragment at its amino terminus has been described {Biotechnology: 10, (1992) page 795-798}. It is possible to use the repeat portion of the Lyta molecule found in the C terminal end starting at residue 178, for example residues 188-305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art Polynucleotides It is an object of the invention to provide polynucleotides, herein designated Nm polynucleotides, which cover the Nm genetic diversity above and “examples” below for a definition of “Nm genetic diversity coverage”), and which correspond to outer membrane and/or periplasma Nm polypeptides. The present invention is particularly related to such Nm polynucleotides which comprises an ORF (open Reading Frame) coding for outer membrane and/or periplasma polypeptides.

In a particularly preferred embodiment of the invention the polynucleotide comprises a sequence set out in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, or a variant thereof The Nm polynucleotides provided in SEQ ID NO: 1, 3, 5, 7, 9, 11, 13, 15, 17, 19, 21, 23, 25 are the dsbA polynucleotides (complete ORF) from *Neisseria meningitidis* strain Z2491, Z3524, Z3842, Z4667, Z4707, Z5055, Z6466, Z7176, Z4662, Z6904, Z4259, Z4673, Z4683 respectively.

The Nm polynucleotide provided in SEQ ID NO: 27 is the 3' end fraction (1047 nucleotides) of the FhaB ORF from *Neisseria meningitidis* strain Z2491.

The Nm polynucleotides provided in SEQ ID NO: 29, 31, 33, 35, 37, 39, 41, 43, 45, 47, 49, 51 are the fhuA polynucleotides (complete ORF) from *Neisseria meningitidis* strain Z2491, Z3524, Z3842, Z4259, Z4662, Z4667, Z4673, Z4683, Z4707, Z5005, Z6904, Z7176 respectively.

The Nm polynucleotide provided in SEQ ID NO: 53 is the rni5 polynucleotide (complete ORF) from *Neisseria meningitidis* strain Z2491.

The Nm polynucleotides provided in SEQ ID NO: 55, 57, 59, 61, 63 are the rth17, respectively rth18, rth19, rth20, rth21 polynucleotides (complete ORF) from *Neisseria meningitidis* strain Z2491.

The Nm polynucleotides provided in SEQ ID NO: 65, 67, 69, 71, 73, 75, 77, 79, 81, 83, 85, 87, 89 are the tolC polynucleotides (complete ORF) from *Neisseria meningitidis* strain Z2491, Z3524, Z4707, Z3842, Z4259, Z4662, Z4667, Z4673, Z4683, Z5005, Z6466, Z6904, Z7176 respectively.

As above explained for Nm polypeptides, Nm polynucleotides have been named according to the ORF with which some correspondance, though with no significant identity/similarity has been found in another species (dsbA, fhaB, fhuA, rth17 and tolC), or, when no correspondance with a gene of known function has been found said Nm polynucleotides have been named according to the Nm region in which they have been located, plus a sequential number (rni5, rth18, rth19, rth20, rth21).

As a further aspect of the invention there are provided isolated nucleic acid molecules encoding and/or expressing Nm polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a Nm polypeptide having a deduced amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, and polynucleotides closely related thereto and variants thereof.

In another particularly preferred embodiment of the invention there is a Nm polypeptide from *Neisseria meningitidis* comprising or consisting of an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, or a variant thereof.

Using the information provided herein, such as a polynucleotide sequence set out in SEQ ID NO: 1, 3, 5, 7, 9, 11, 13, 15, 17, 19, 21, 23, 25, 27, 29, 31, 33, 35, 37, 39, 41, 43, 45,47, 49, 51, 53, 55, 57, 59, 61, 63, 65, 67, 69, 71, 73, 75, 77, 79, 81, 83, 85, 87, 89, a polynucleotide of the invention encoding Nm polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, typically a library of clones of chromosomal DNA of *Neisseria meningitidis* in *E.coli* (such as a lambda DashII library) or some other suitable host is probed with a radiolabeled oligonucleotide, preferably a 17-mer or longer, derived from a partial sequence. Examples of such probes can be obtained by PCR amplification with the primers SEQ ID No: 97-116 and with Nm Z2491 DNA as target DNA (see example 1 and Table 2 below).

Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F.

and Sambrook et al., *MOLECULAR CLONING, A LABORATORY MANUAL,* 2nd Ed.; Cold Spring Harbor Laboratory Press, Cold Spring Harbor, N.Y. (1989) (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, was discovered in a DNA library derived from a *Neisseria meningitidis* panel (MLST).

Moreover, each DNA sequence set out in SEQ ID NO: 1, 3, 5, 7, 9, 11, 13, 15, 17, 19, 21, 23, 25, 29, 31, 33, 35, 37, 39,41, 43, 45, 47, 49, 51, 53, 55, 57, 59, 61, 63, 65, 67, 69, 71, 73, 75, 77, 79, 81, 83, 85, 87, 89 corresponds to an open reading frame (ORF) encoding a protein having about the number of amino acid residues set forth in SEQ ID NO: 2, 4, 6, 8, 10, 12, 14, 16, 18, 20, 22, 24, 26, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, respectively with a deduced molecular weight that can be calculated using amino acid residue molecular weight values well known to those skilled in the art. The DNA sequence set out in SEQ ID No: 27 corresponds to the 1047 3' end fraction of the ORF encoding a protein having about the number of amino acid residues set forth in SEQ ID NO: 28.

In a further aspect, the present invention provides for an isolated polynucleotide comprising or consisting of:

(a) a polynucleotide sequence which has at least 70% identity, preferably at least 80% identity, more preferably at least 90% identity, yet more preferably at least 95% identity, even more preferably at least 97-99% or exact identity to SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, over the entire length of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, (b) a polynucleotide sequence encoding a polypeptide which has at least 70% identity, preferably at least 80% identity, more preferably at least 90% identity, yet more preferably at least 95% identity, even more preferably at least 97-99% or 100% exact, to the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90 over the entire length of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90 respectively.

A polynucleotide encoding a polypeptide of the present invention may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, or a fragment thereof; and isolating a fill-length gene and/or genomic clones containing said polynucleotide sequence.

The invention provides a polynucleotide sequence identical over its entire length to a coding sequence (open reading frame) in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-tanslated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded In certain embodiments of the invention, the marker sequence is a hexa-histidine peptide, as provided in the pQE vector (Qiagen, Inc.) and described in Gentz et al., *Proc. Natl. Acad Sci., USA* 86: 821-824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding Nm polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90 may be identical to the polypeptide encoding sequence contained in Nm nucleotides of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, respectively. Alternatively it may be a sequence, which as a result of the redundancy (degeneracy) of the genetic code, also encodes the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90.

The term "polynucleotide encoding a polypeptide" as used herein encompasses polynucleotides that include a sequence encoding a polypeptide of the invention, particularly a *Neisseria meningitidis* polypeptide having an amino acid sequence set out in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90. Fragments of polynucleotides of the invention may be used, for example, to synthesize full-length polynucleotides of the invention.

Further particularly preferred embodiments are polynucleotides encoding Nm variants, that have the amino acid sequence of Nm polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90 in which several a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of Nm polypeptide.

Further preferred embodiments of the invention are polynucleotides that are at least 70% identical over their entire length to a polynucleotide encoding Nm polypeptide having an amino acid sequence set out in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, and polynucleotides that are complementary to such polynucleotides. Alternatively, most highly preferred are polynucleotides that comprise a region that is at least 80% identical over its entire length to a polynucleotide encoding Nm polypeptide and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89.

In accordance with certain preferred embodiments of this invention there are provided polynucleotides that hybridize, particularly under stringent conditions, to Nm polynucleotide sequences, such as those polynucleotides in SEQ ID NO : 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89 under stringent hybridization conditions with a probe having the sequence of said polynucleotide sequence set forth in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, or a fragment thereof; and isolating said polynucleotide sequence. Fragments useful for obtaining such a polynucleotide include, for example, probes and primers fully described elsewhere herein. An appropriate library may e.g. be a lambda DashII library containing Nm Z2491 ADN fragments from about 12 to about 23 kb.

As discussed elsewhere herein regarding polynucleotide assays of the invention, for instance, the polynucleotides of the invention, may be used as a hybridization probe for RNA, cDNA and genomic DNA to isolate fill-length cDNAs and genomic clones encoding Nm polypeptides, and to isolate cDNA and genomic clones of other genes that have a high identity, particularly high sequence identity, to the Nm gene. Such probes generally will comprise at least 15 nucleotide residues or base pairs. Preferably, such probes will have at least 30 nucleotide residues or base pairs and may have at least 50 nucleotide residues or base pairs.

Particularly preferred probes will have at least 20 nucleotide residues or base pairs and will have less than 30 nucleotide residues or base pairs.

A coding region of a Nm gene may be isolated by screening using a DNA sequence provided in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998-9002, 1988). Recent modifications of the technique, exemplified by the Marathons technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for Nm-related diseases, particularly human Nm-related diseases, as further discussed herein relating to polynucleotide assays.

The polynucleotides of the invention that are oligonucleotides derived from a sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., *Hum Mol Genet (*1992) 1: 363, Manthorpe et al., *Hum. Gene Ther*. (1983) 4: 419), delivery of DNA complexed with specific protein carriers (Wu et al., *J Biol Chem*. (1989) 264: 16985), coprecipitation of DNA with calcium phosphate (Benvenisty & Reshef, *PNAS USA*, (1986) 83: 9551), encapsulation of DNA in various forms of liposomes (Kaneda et al., *Science (*1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING. A LABORATORY MANUAL,* 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci enterococci, *E. coli*, streptomyces, cyanobacteria, *Bacillus subtilis*, and *Neisseria meningitidis*; fungal cells, such as cells of a yeast, *Kluveromyces, Saccharomyces*, a basidiomycete, *Candida albicans* and *Aspergillus*; insect cells such as cells of *Drosophila* S2 and *Spodoptera* Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviuuses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g. vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc.), Listeria, Salmonella, Shigella, BCG. These viruses and bacteria can be virulent, or attenuated in various ways in order to obtain live vaccines. Such live vaccines also form part of the invention.

Diagnostic, Prognostic, Serotyping and Mutation Assays

This invention is also related to the use of Nm polynucleotides and Nm polypeptides of the invention for use as diagnostic reagents. Detection of Nm polynucleotides and/or polypeptides in an eukaryote, particularly a mammal, and especially a human, will provide a diagnostic method for diagnosis of Nm-related disease, staging of disease or response of an infectious organism to drugs. Eukaryotes, particularly mammals, and especially humans, particularly those infected or suspected to be infected with an organism comprising the Nm gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled Nm polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science,* 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad Sci., USA,* 85: 4397-4401 (1985).

In another embodiment, an array of oligonucleotides probes comprising Nm nucleotide sequence or fragments thereof can be constructed to conduct efficient screening of for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science,* 274: 610 (1996)).

Thus in another aspect, the present invention relates to a diagnostic kit which comprises:

(a) at least one polynucleotide of the present invention, preferably the nucleotide sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, or a fragment thereof; and/or (b) at least one nucleotide sequence complementary to that of (a); and/or (c) at least one polypeptide of the present invention, preferably the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, or a fragment thereof; and/or (d) at least one antibody to a polypeptide of the present invention, preferably to the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90.

It will be appreciated that in any such kit, (a), (b), (c) or (d) may comprise a substantial component. Such a kit will be of use in diagnosing a disease or susceptibility to a Nm-related disease.

This invention also relates to the use of polynucleotides of the present invention as diagnostic reagents. Detection of a mutated form of a polynucleotide of the invention, preferably, SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, which is associated with a Nm-related disease or pathogenicity will provide a diagnostic tool that can add to, or define, a diagnosis of said disease, a prognosis of a course of disease, a determination of a stage of disease, or a susceptibility to said disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR As an example, PCR primers complementary to a polynucleotide encoding Nm polypeptide can be used to identify and analyze mutations.

The invention further provides primers with 1, 2, 3 or 4 nucleotides removed from the 5' and/or the 3' end. These primers may be used for, among other things, amplifying Nm DNA and/or RNA isolated from a sample derived from an individual such as a bodily material. The primers may be used to amplify a polynucleotide isolated from an Nm-infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing infections caused by *Neisseria meningitides*, comprising determining from a sample derived from an individual, such as a bodily material, an increased level of expression of polynucleotide having a sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89. Increased or decreased expression of a Nm polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of Nm polypeptide compared to normal control tissue samples may be used to detect the presence of an infection, for example. Assay techniques that can be used to determine levels of a Nm polypeptide, in a sample derived from a host, such as a bodily material are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probes obtained or derived from a bodily sample, to determine the presence of a particular polynucleotide sequence or related sequence in an individual. Such a presence may indicate the presence of a pathogen, particularly *Neisseria meningitides*, and may be useful in diagnosing and/or prognosing a Nm-related infection or a course of infection. A grid comprising a number of variants of the polynucleotide sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, are preferred. Also preferred is a comprising a number of variants of a polynucleotide sequence encoding the polypeptide sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against Nm polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Köhler, G. and Milstein, C., *Nature* 256: 495-497 (1975); Kozbor et al., *Immunology Today* 4: 72 (1983); Cole et al., pg. 77-96 in *MONOCLONAL ANTIBODIES AND CANCER THERAPY*, Alan R. Lists, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention preferably, said antibodies can bind to at least one Nm polypeptide according to the invention in in vivo conditions, or in in vitro ones mimicking in vivo ones, but do not recognize the patient cells.

Alternatively, phage display technology may be utilized to select antibody genes with binding activities towards a polypeptide of the invention either from repertoires of PCR amplified v-genes of lymphocytes from humans screened for possessing anti-Nm or from naive libraries (McCafferty, et al., (1990), Nature 348, 552-554; Marks, et al., (1992) *Biotechnology* 10, 779-783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against Nm-polypeptide or Nm-polynucleotide may be employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarily determining region or regions of the hybridoma-derived antibody has been transplanted into a human monoclonal antibody, for example as described in Jones et al. (1986), *Nature* 321, 522-525 or Tempest et al., (1991) *Biotechnology* 9, 266-273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring Nm polypeptide and/or polynucleotide activity in the mixture, and comparing the Nm polypeptide and/or polynucleotide activity of the mixture to a standard. Fusion proteins, such as those made from Fc portion and Nm polypeptide, as hereinbefore described, can also be used for high-throughput screening assays to identify antagonists of the polypeptide of the present invention, as well as of phylogenetically and/or functionally related polypeptides (see D. Bennett et al., J Mol Recognition, 8:52-58 (1995); and K. Johanson et al., J Biol Chem, 270(16):9459-9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of Nm polypeptides or polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising Nm polypeptide and a labeled substrate or ligand of such polypeptide is incubated in the absence or the presence of a candidate molecule that may be a Nm agonist or antagonist. The ability of the candidate molecule to agonize or antagonize the Nm polypeptide is reflected in decreased binding of the labeled ligand or decreased production of product from such substrate. Molecules that bind gratuitously, i.e., without inducing the effects of Nm polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to calorimetric, labeled substrate converted into product, a reporter gene that is responsive to changes in Nm polynucleotide or polypeptide activity, and binding assays known in the art.

Another example of an assay for Nm agonists is a competitive assay that combines an Nm compound according to the invention and a potential agonist with Nm compound binding molecules, recombinant Nm binding molecules, natural substrates or ligands, or substrate or ligand mimetics, under appropriate conditions for a competitive inhibition assay. Said Nm compound can be labeled, such as by radioactivity or a colorimetric compound, such that the number of Nm molecules bound to a binding molecule or converted to product can be determined accurately to assess the effectiveness of the potential antagonist Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing activities induced by a Nm compound according to the invention, thereby preventing the action or expression of Nm polypeptides and/or polynucleotides by excluding Nm polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of NMEN.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial Nm proteins that mediate tissue damage and/or; to block the normal progression of pathogenesis in infections initiated other than by the implantation of in-dwelling devices or by other surgical techniques.

In accordance with yet another aspect of the invention, there are provided Nm agonists and antagonists of said Nm compounds according to the invention, preferably bacteristatic or bactericidal agonists and antagonists.

The antagonists and agonists of the invention may be employed, for instance, to prevent, inhibit and/or treat Nm-related diseases.

In a further aspect, the present invention relates to mimotopes of the polypeptide of the invention. A mimotope is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with Nm polynucleotide and/or Nm polypeptide, or a fragment or variant thereof, adequate to produce antibody and/ or T cell immune response to protect said individual from infection, particularly bacterial infection and most particularly *Neisseria meningitidis* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of Nm polynucleotide and/or polypeptide, or a fragment or a variant thereof, for expressing Nm polynucleotide and/or polypeptide, or a fragment or a variant thereof in vivo in order to induce an immunological response, such as, to produce antibody and/ or T cell immune response, including, for example, cytokine-producing T cells or cytotoxic T cells, to protect said individual, preferably a human, from a Nm-related disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex. The expression system may also be a recombinant live micro-organism, such as a virus or a bacterium, which can be virulent, or attenuated in various ways in order to obtain live vaccines (see "Vectors, Host Cells, Expression Systems" above).

A further aspect of the invention relates to an immunological composition that when introduced into an individual, preferably a human, capable of having induced within it an immunological response, induces an immunological response in such individual to a Nm polynucleotide and/or Nm polypeptide encoded therefrom, wherein the composition comprises a recombinant Nm polynucleotide and/or polypeptide encoded therefrom and/or comprises DNA and/or RNA which encodes and expresses an antigen of said Nm polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+T cells.

The immunological methods and compositions according to the invention advantageously show efficacies against at least one Nm strain belonging to one serogroup, preferably against at least two Nm strains belonging to more than one Nm serogroups, preferably more than two Nm serogroups, most preferably more than three Nm serogroups e.g. against Nm serogroups A, B, C and W135 and/or Y.

A Nm polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Haemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

Provided by this invention are compositions, particularly vaccine compositions, and methods comprising the polypeptides and/or polynucleotides of the invention and immunostimulatory DNA sequences, such as those described in Sato, Y. et al. Science 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in anal models of infection with *Neisseria meningitidis*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Neisseria meningitidis* infection, in mammmals, particularly humans.

The invention also includes a vaccine formulation which comprises an immunogenic recombinant polypeptide and/or polynucleotide of the invention together with a suitable carrier, such as a pharmaceutically acceptable carrier. The vaccine formulation according to the invention advantageously shows efficacies against at least one Nm serogroup, advantageously more than 2 Nm serogroups, preferably more than 3 Nm serogroups (e.g. Nm serogroups A, B, C and W135 and/or Y), most preferably against any Nm strain. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. Preferably, the vaccine formulation according to the invention is a anti-Nm meningitidis formulation.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4 +ve T cell clones by Mosmann and Coffman (*Mosmann, T. R. and Coffman, R. L.* .(1989) TH1 and TH2 *cells: different patterns of lymphokine secretion lead to different functional properties. Annual Review of Immunology,* 7, p145-173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKine Beecham Biologicals SA).

Preferably, the particles of 3D-MPL are small enough to be sterile filtered through a 0.22 micron membrane (European Patent number 0 689 454). 3D-MPL will be present in the range of 10 mg-100 mg preferably 25-50 mg per dose wherein the antigen will typically be present in a range 2-50 mg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. NO:5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5: 1 to 1: 1 3D-MPL:QS21.

Preferably a carrier is also present in the vaccine composition according to the invention. The carrier may be an oil in water emulsion, or an aluminium salt, such as aluminium phosphate or aluminum hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 mg-200 mg, such as 10-100 mg, preferably 10mg-50 mg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, or autoimmune diseases. Such a polyvalent vaccine composition may include a TH-1 inducing adjuvant as hereinbefore described.

While the invention has been described with reference to certain Nm polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

Compositions, Kits and Administration

In a further aspect of the invention there are provided compositions comprising a Nm polynucleotide and/or a Nm polypeptide for administration to a cell or to a multicellular organism.

The invention also relates to compositions comprising a polynucleotide and/or a polypeptides discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal vaginal intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds. The present invention also provides for a therapeutic composition useful in treating animals or humans with *Neisseria meningitidis*-related disease, said composition comprising at least one antibody directed against a polypeptide according to the invention, and a suitable pharmaceutical carrier. Preferably, said antibody does not recognize the patient cells.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 μg/kg to 100 μg/kg, preferably from 0.1 to 10 μg/kg, typically around 1 μg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1-100 μg/kg of subject.

A vaccine composition is conveniently in injectable form. Conventional adjuvants may be employed to enhance the immune response. A suitable unit dose for vaccination is 0.5-5 microgram/kg of antigen, and such dose is preferably administered 1-3. times and with an interval of 1-3 weeks. With the indicated dose range, no adverse toxicological effects will be observed with the compounds of the invention which would preclude their administration to suitable individuals. A preferred vaccine composition is an anti-Nm *meningitidis* vaccine composition.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Definitions

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.,* 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J. Molec. Biol.* 215: 403-410 (1990), and FASTA (Pearson and Lipman Proc. Natl. Acad. Sci. USA 85; 2444-2448 (1988). The BLAST family of programs is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following:

Algorithm: Needleman and Wunsch, J. Mol Biol. 48: 443-453 (1970)

Comparison matrix: BLOSSUM62 from Henikoff and Henikoff,

Proc. Natl. Acad. Sci. USA. 89:10915-10919 (1992)

Gap Penalty: 8

Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm:. Needleman and Wunsch, J. Mol Biol. 48: 443-453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case maybe, are provided in (1) and (2) below.

(1) Polynucleotide embodiments further include an isolated polynucleotide comprising a polynucleotide sequence having at least a 70, 80, 85, 90, 95, 97 or 100% identity to the reference sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, wherein said polynucleotide sequence may be identical to the reference sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, by the integer defining the percent identity divided by 100 and then subtracting that product from said total number of nucleotides in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89:

$$n_n \leq x_n - (x_n \cdot y),$$

wherein $n_n$ is the number of nucleotide alterations, $x_n$ is the total number of nucleotides in SEQ ID NO: 1, 3, 5, 7, 9, 1, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, y is 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, by the integer defining the percent identity divided by 100 and then subtracting that product from said total number of nucleic acids in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, or:

$$n_n \leq x_n - (x_n \cdot y),$$

wherein $n_n$ is the number of nucleic acid alterations, $x_n$ is the total number of nucleic acids in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, or 89, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 70, 77, 80, 87, 89 or 100% identity to a polypeptide reference sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, wherein said polypeptide sequence may be identical to the reference sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, by the integer defining the percent identity divided by 100 and then subtracting that product from said total number of amino acids in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90:

$$n_a \leq x_a - (x_a \cdot y),$$

wherein $n_a$ is the number of amino acid alterations, $x_a$ s the total number of amino acids in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, y is 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, by the integer defining the percent identity divided by 100 and then subtracting that product from said total number of amino acids in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90

$$n_a \leq x_a - (x_a \cdot y),$$

wherein $n_a$ is the number of amino acid alterations, $x_a$ is the total number of amino acids in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by at least one *Neisseria meningitidis* stain, such as Nm meningitis.

Figure 47:
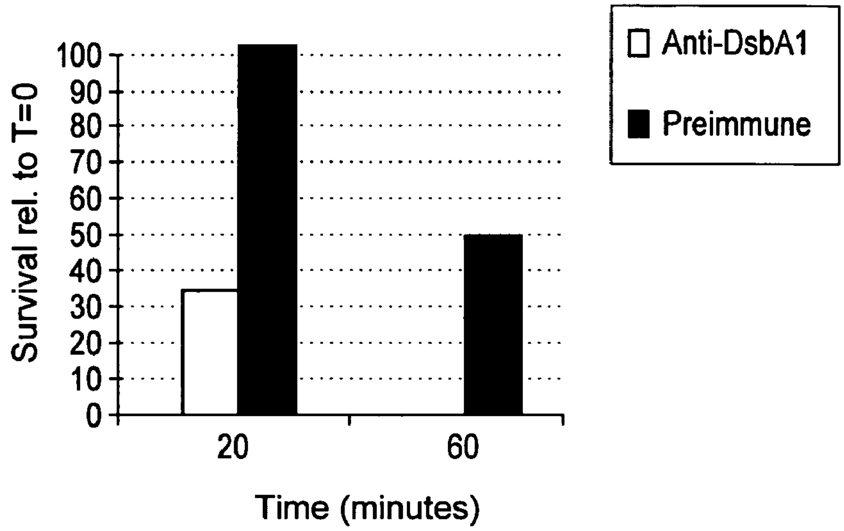
Figure 48:
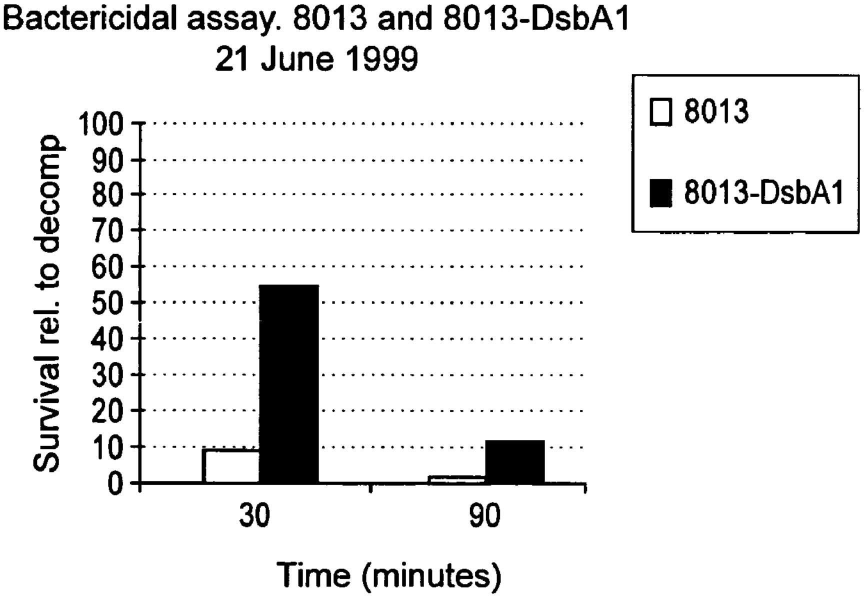
Figure 49:
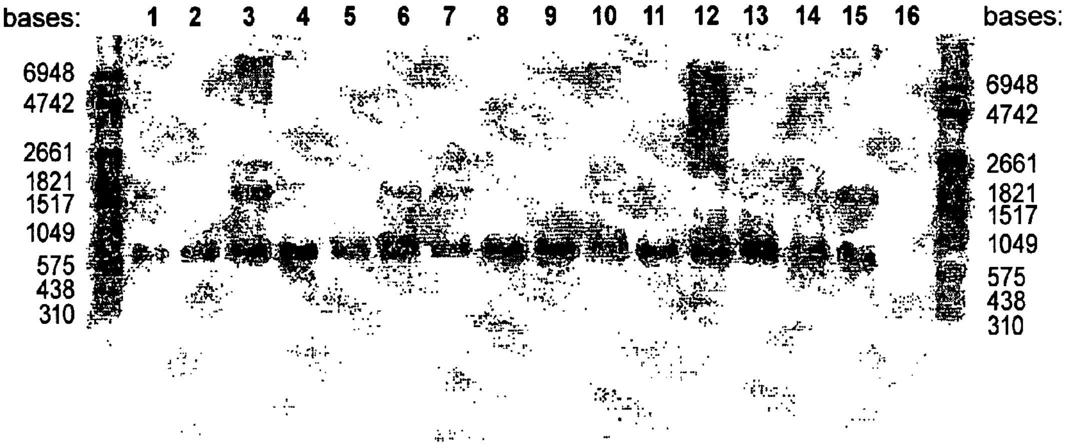

In the below examples, reference is made to FIGS. 1 to 50 which represent (for FIG. 1 to 45: "A" letters for polynucleotidic sequences, "B" letters for polypeptidic ones):

FIGS. 1 to 13 correspond dsbA/DsBA sequences obtained:

for allele 1:

from Nm strain Z2491 (FIGS. 1A and 1A-1, 1B),
from Nm strain Z3524 (FIGS. 2A and 2A-1, 2B),
from Nm strain Z3842 (FIGS. 3A and 3A-1, 3B),
from Nm strain Z4667 (FIGS. 4A and 4A-1, 4B),
from Nm strain Z4707 (FIGS. 5A and 5A-1, 5B),
from Nm strain Z5005 (FIGS. 6A and 6A-1, 6B),
from Nm strain Z6466 (FIGS. 7A and 7A-1, 7B),
from Nm strain Z7176 (FIGS. 8A and 8A-1, 8B), for allele 2:

from Nm strain Z4662 (FIGS. 9A and 9A-1, 9B),
from Nm strain Z6904 (FIGS. 10A and 10A-1, 10B), for allele 3 from Nm strain Z4259 (FIGS. 11A and 11A-1, 11B),
from Nm strain Z4673 (FIGS. 12A and 12A-1, 12B), for allele 4:

from Nm strain Z4683 (FIGS. 13A, and 13A-1, 13B),

FIGS. 14A and 14A-1 (1047 nucleotides) and 14B (348 aminoacids) correspond to the 3' end fraction of the fhaB, respectively FhaB, sequences obtained from Nm strain Z2491, FIGS. 15 to 26 correspond to fhuA, FhuA sequences obtained from:

from Nm strain Z2491 (FIGS. 15A, 15A-1, 15A-2 and 15A-3, 15B and 15B-1),
from Nm strain Z3524 (FIGS. 16A, 16A-1, 16A-2 and 16A-3, 16B and 16B-1),
from Nm strain Z3842 (FIGS. 17A, 17A-1, 17A-2 and 17A-3, 17B and 17B-1),
from Nm strain Z4259 (FIGS. 18A, 18A-1, 18A-2 and 18A-3, 18B and 18B-1),
from Nm strain Z4662 (FIGS. 19A, 19A-1, 19A-2 and 19A-3, 19B and 19B-1),
from Nm strain Z4667 (FIGS. 20A, 20A-1, 20A-2 and 20A-3, 20B and 20B-1),
from Nm strain Z4673 (FIGS. 21A, 21A-1, 21A-2 and 21A-3, 21B and 21B-1),
from Nm strain Z4683 (FIGS. 22A, 22A-1, 22A-2 and 22A-3, 22B and 22B-1),
from Nm strain Z4707 (FIGS. 23A, 23A-1, 23A-2 and 23A-3, 23B and 23B-1),
from Nm strain Z5005 (FIGS. 24A, 24A-1, 24A-2 and 24A-3, 24B and 24B-1),
from Nm strain Z6904 (FIGS. 25A, 25A-1, 25A-2 and 25A-3, 25B and 25B-1),
from Nm strain Z7176 (FIGS. 26A, 26A-1, 26A-2 and 26A-3, 26B and 26B-1), FIGS. 27A, 27B and 27B-1 correspond to rni5, respectively Rni5, sequences obtained from Nm Z2491, FIGS. 28A and 28B correspond to rth17, respectively Rth17, sequences obtained from Nm Z2491, FIGS. 29A and 29B correspond to rth18, respectively Rth18, sequences obtained from Nm Z2491, FIGS. 30A and 30B correspond to rth19, respectively Rth19, sequences obtained from Nm Z2491, FIGS. 31A and 31B correspond to rth20, respectively Rth20, sequences obtained from Nm Z2491, FIGS. 32A and 32B correspond to rth21, respectively Rth21, sequences obtained from Nm Z2491, FIGS. 33 to 45 correspond to tolC/TolC sequences obtained:

for allele 1:

from Nm strain Z2491 (FIGS. 33A, 33A-1, 33A-2, 33B), from Nm strain Z3524 (FIGS. 34A, 34A-1, and 34A-2, 34B), for allele 2:

from Nm strain Z4707 (FIGS. 35A, 35A-1 and 35A-2, 35B), for allele 3:

from Nm strain Z3842 (FIGS. 36A, 36A-1 and 36A-2, 36B), from Nm strain Z4259 (FIGS. 37A, 37A-1 and 37A-2, 37B), from Nm strain Z4662 (FIGS. 38A, 38A-1 and 38A-2, 38B), from Nm strain Z4683 (FIGS. 39A, 39A-1 and 39A-2, 39B), from Nm strain Z4673 (FIGS. 40A, 40A-1 and 40A-2, 40B), from Nm strain Z4667 (FIGS. 41A, 41A-1 and 41A-2, 41B), from Nm strain Z5005 (FIGS. 42A, 42A-1 and 42A-2, 42B), from Nm strain Z6466 (FIGS. 43A, 43A-1 and 43A-2, 43B), from Nm strain Z6904 (FIGS. 44A and 44A-1, 44B and 44B-1), from Nm strain Z7176 (FIGS. 45A, 45A-1 and 45A-2 and 45B), FIG. 46 illustrates the production of a knockout mutation of DsbA, FIG. 47 illustrates the bactericidal activity of anti-DsbA and the corresponding pre-immune serum FIG. 48 illustrates the bactericidal activity of anti-DsbA antiserum against meringococci expressing an isogenic mutant lacking the protein DsbA, FIG. 49 illustrates Northern blot controls of the presence of DsbA in every MLST strains.

EXAMPLE 1

The examples below are carried out using standard techniques, which are well known and routine to those of skill in the art, except where otherwise described in detail. The examples are illustrative, but do not limit the invention.

Strains of Nm were tested that represent the genetic diversity of this species according to MLST (Maiden et al. 1998, supra).

TABLE 1

| Nm strain Z number | Serological group | Clonal subgroup | ST |
|---|---|---|---|
| 2491 | A | IV-1 | 4 |
| 5005 | A | I | 1 |
| 3524 | A | III | 5 |
| 6466 | A | IX | 60 |
| 4662 | B | groupe A4 | 8 |
| 3842 | B | ET-5 (44/76) | 32 |
| 7176 | B | ET-5 (MC58) | 74 |
| 4673 | B | Lignée 3 | 41 |
| 4259 | C | ET-37 (FAM18) | 11 |

TABLE 1-continued

| Nm strain Z number | Serological group | Clonal subgroup | ST |
|---|---|---|---|
| 6904 | W135 | ET-37 (ROU) | 11 |
| 4690 | B | Autre | 25 |
| 4683 | B | Autre | 30 |
| 4707 | B | Autre | 49 |
| 4667 | B | Autre | 48 |

Their MLST assignments were: ST1 (subgroup L strain B40); ST2 (subgroup VI, Z6835); ST4 (subgroup IV-1, Z2491 (Sarkari et al., 1994 Mol. Microbiol. 13: 207-217)), ST5 (subgroup III, Z3524); ST8 (A4 cluster, BZ 10); ST11 (ET-37 complex, serogroup C: FAM18; serogroup W135: ROU (Pron et al., 1997, J. Infect. Dis. 176: 1285-1292)); ST 25 (NG G40); ST30 (NG 4/88); ST32 ET-5 complex, 44/76); ST41 (lineage 3, BZ 198); ST48 (BZ147); ST49 (297-0); ST60q (subgroup IX, 890592) et ST74 (ET-5 complex, MC58 (Virji et al., 1995, Mol. Microbiol. 18: 741-754)).

Nm were grown on GC agar (GCB, Difco), with the addition of Kellogg's defined supplement plus ferric nitrate (Kellog et al., 1963) for 12 to 20 hours at 37° C. in a moist atmosphere containing 5% $CO_2$. Liquid media were GC-$PO_4$ (1.5% Protease peptone number3 (Difco), 0.5% NaCl, 30 mM potassium phosphate, pH 7.5) and GC-Hepes (like GC-$PO_4$ but potassium phosphate replaced by 30 mM Hepes, pH7.5) both supplemented as for the solid medium.

Cloning of the Polynucleotides Coding for Outer Membrane and/or Periplasma Polypeptides in Each Nm Strains By sequencing a Nm DNA library, such as a lambda DashII library containing 12-23 kb DNA fragments of Nm Z2491, nine ORF coding for outer membrane and/or periplasma polypeptides were cloned into *E. coli* and sequenced:

dsbA (allele 1) SEQ ID NO: 1 (corresponding polypeptide: SEQ ID NO: 2), fhuA SEQ ID No: 29 (corresponding polypeptide: SEQ ID NO: 30), rni5 SEQ ID No: 53 (corresponding polypeptide: SEQ ID No: 54), rth17 SEQ ID No: 55 (corresponding polypeptide: SEQ ID No: 56), rth18 SEQ ID No: 57 (corresponding polypeptide: SEQ ID No: 58), rth19 SEQ ID No: 59 (corresponding polypeptide: SEQ ID No: 60), rth20 SEQ ID No: 61 (corresponding polypeptide: SEQ ID No: 62), rth21 SEQ ID No: 63 (corresponding polypeptide: SEQ ID No: 64), tolC (allele 1) SEQ ID No: 65 (corresponding polypeptide: SEQ ID No: 66).

A further tenth ORF was identified as fhaB, but only a 3' end fraction of this ORF is herewith given:SEQ ID No 27 (1047 nucleotides).

These sequences are illustrated by FIGS. 1A, 1A-1 and 1B, 14A, 14A-1 and 14B, 27A, 27B and 27B-1, 28A and 28B, 29A and 29B, 30A and 30B, 31A and 31B, 32A and 32B, 33A, 33A-1, 33A-2 and 33B respectively, as above-recited (fig. number+A letter: polynucleotides; same fig. number+B letter: corresponding polypeptides).

From these 10 new products isolated from Nm Z2491, probes were constructed so as to determine whether these 9 new ORF and the complete ORF corresponding to said new fhaB ORF fraction are also present in the MLST Nm panel.

Means for obtaining such probes include PCR amplification using the primers recited as SEQ ID No: 97-116 and chromosomal DNA from Nm Z2491 as target DNA. Appropriate PCR conditions for obtaining such probes with said primers and DNA template can be determined by the person skilled in the art ; as an example, these conditions may be: 1 µg. ml$^{-1}$ of template DNA; reaction buffer (10 mM Tris-Cl, pH 8.0, 50 mM KCl, 1.5 mM MgCl2, 0.001% gelatin); DATP, dCTP, dGTP and dTTP (200 µM each); dimethylsulfoxide (5%); forward and reverse primers (100 nM each) and Taq polymerase; PCR incubation: 1 min at 94° C., 30 cycles of 1 min at 94°C., 1.5 min at 5° C. below the Tm of the oligonucleotide primers, and 2 min at 72° C. followed by incubation for 5 min at 72° C. Primer sequences are given in the below Table 2, together with the size of the PCR products thus obtained:

TABLE 2

| ORF | forward primer | 5'-3' sequence | reverse primer | 5'-3' sequence | size of PCR product (kb) |
|---|---|---|---|---|---|
| fhaB (probe, N-term) | fhaB-for | AAAGCACAGCACCATGGTTGCAGTAGCCGAAAC (SEQ ID N°115) | fhaB-rev | AGTGTCTTTAGCCTCAATTACAGCAG CACTGCC (SEQ ID N°116) | 1.40 |
| rth17 | rth17-for | ACCGTGAGGCGGACTTGGC (SEQ ID N°107) | rth17-rev | TGGCCCGCATTGTCGGGTTTAAAGCC GTCTTCG (SEQ ID N°108) | 0.32 |
| rth18* | rth18-for | ATTTGCGGAGGGCGAACTGG (SEQ ID N°109) | rth18-rev | GCTTCGCAAAAGCCGACTTG (SEQ ID N°110) | 0.40 |
| rth19 | rth19-for | GGCAACCGATTGCCATCATC (SEQ ID N°111) | rth19-rev | TTTCCGTTTTCAGACGGCTG (SEQ ID N°112) | 0.27 |
| rth20 | rth20-for | AAGACCGTAAAAATGCAGGCG (SEQ ID N°113) | rth20-rev | TTTCCGACTTTGCGGGAGTG (SEQ ID N°114) | 0.29 |
| rth21 | rth21-for | GGTTGGCTGCTTTCAAACGC (SEQ ID N°115) | rth21-rev | ATTAAATATTTTGTCCGCTTGTAC (SEQ ID N°116) | 0.28 |
| tolC | tolC-for | GCCTGACACTGACGCCCTATTTGCAACATGAAC (SEQ ID N°103) | tolC-rev | TACCGTGCTTGAGCCAGTTTCTGTTC TGCTTGG (SEQ ID N°104) | 1.28 |
| dsbA | dsbA-for | GCTTTGACTTCATTGACCCTGTTGGCATTGGCC (SEQ ID N°97) | dsbA-rev | TATCCACCAACTGGTCAATCGTGGTC ATACCGG (SEQ ID N°99) | 0.65 |
| fhuA | fhuA-for | CCACGCTGATTATTGCTTCCTTCCCTGTTGCTG (SEQ ID N°99) | fhuA-rev | ACCCGGCATAGAGTCCGAACGCCAAT ATTTTTG (SEQ ID N°100) | 2.04 |
| rni5 | rni5-for | TGTTTCCCACCCAAACTTAC (SEQ ID N°101) | rni5-rev | GTTCGTGGATGCAGACATAG (SEQ ID N°102) | 0.36 |

*primers for rth18 are lying upstream of the start and downstream of the stop codon.

These hybridization experiments performed under usual stringency conditions led to the conclusion that the nine new ORF and the complete ORF corresponding to the new fhaB fraction, which were isolated from Nm Z2491, are present in every Nm strain of the MLST panel. DNA dot blot hybridization was performed according to the DIG System Users Guide (Boehringer). One microliter containing 100 ng of denatured chromosomal DNA from each strain was spotted on nylon membranes (Hybond N, Amersham) and hybridized with DIG-labeled probes obtained by PCR amplification of each ORF. The hybridizations were performed using high SDS buffer (Church buffer) at 37° C., and the last washing step was with 0.5×SSC, 0.1% SDS at 50° C. in order to allow approximately 30% mismatch Positive hybridization signals were detected by chemiluminescence.

Some of these precise sequences corresponding to those initially isolated in Nm Z2491 are shown on (A letter for polynucleotides; B letter for corresponding polypeptides):

FIGS. 2A and 2A-1 and 2B (Nm Z3524; SEQ ID No3 and 4, respectively), FIGS. 3A and 3A-1 and 3B (Nm Z4832; SEQ ID No5 and 6, respectively), FIGS. 4A and 4A-1 and 4B (Nm Z4667; SEQ ID No7 and 8, respectively), FIGS. 5A and 5A-1 and 5B (Nm Z4707; SEQ ID No9 and 10, respectively), FIGS. 6A and 6A-1 and 6B (Nm Z5005; SEQ ID No11 and 12, respectively), FIGS. 7A and 7A-1 and 7B (Nm Z6466; SEQ ID No13 and 14, respectively),FIGS. 8A and 8A-1 and 8B (Nm Z7176; SEQ ID No15 and 16, respectively), FIGS. 9A and 9A-1 and 9B (Nm Z4662; SEQ ID No17 and 18, respectively), FIGS. 10A and 10A-1 and 10B (Nm Z6904; SEQ ID No19 and 20, respectively), FIGS. 11A and 11A-1 and 11B (Nm Z4259; SEQ ID No21 and 22, respectively), FIGS. 12A and 12A-1 and 12B (Nm Z4673; SEQ ID No23 and 24, respectively), FIGS. 13A and 13A-1 and 13B (Nm Z4683; SEQ ID No25 and 26, respectively), for dsbA (respectively DsbA), FIGS. 16A and 16A-1, 16A-2 and 16A-3 and 16B and 16B-1 (Nm Z3524; SEQ ID No31 and 32, respectively), FIGS.17A and 17A-1 ,17A-2 and 17A-3 and 17B and 17B-1 (Nm Z3842; SEQ ID No33 and 34, respectively), FIGS. 18A, 18A-1, 18A-2, and 18A-3 and 18B and 18B-1 (Nm Z4259; SEQ ID No35 and 36, respectively), FIGS. 19A, 19A-1, 19A-2 and 19A-3 and 19B and 19B-1 (Nm Z4662; SEQ ID No37 and 38, respectively), FIGS. 20A, 20A-1, 20A-2 and 20A-3,and 20B and 20B-1 (Nm Z4667; SEQ ID No39 and 40, respectively), FIGS. 21A, 21A-1, 21A-2 and 21A-3, and 21B and 21B-1 (Nm Z4673; SEQ ID No41 and 42, respectively), FIGS. 22A, 22A-1, 22A-2 and 22A-3, and 22B and 22B-1 (Nm Z4683; SEQ ID No43 and 44, respectively), FIGS. 23A, 23A-1, 23A-2 and 23A-3, and 23B and 23B-1 (Nm Z4707; SEQ ID No45 and 46, respectively), FIGS. 24A, 24A-1, 24A-2 and 24A-3, and 24B and 24B-1 (Nm Z5005; SEQ ID No47 and 48, respectively), FIGS. 25A, 25A-1, 25A-2 and 25A-3, and 25B and 25B-1 (Nm Z6904; SEQ ID No49 and 50, respectively), FIGS. 26A, 26A-1, 26A-2 and 26A-3, and 26B and 26B-1 (Nm Z7176; SEQ ID No51 and 52, respectively), for fhuA (respectively FhuA), FIGS. 34A, 34A-1 and 34A-2, and 34B (Nm Z3524; SEQ ID No67 and 68, respectively), FIGS. 35A, 35A-1 and 35A-2, and 35B (Nm Z4707; SEQ ID No:69 and 70, respectively), FIGS. 36A, 36A-1 and 36A-2, and 36B (Nm Z3842; SEQ ID No71 and 72, respectively), FIGS. 37A, 37A-1 and 37A-2, and 37B (Nm Z4259; SEQ ID No73 and 74, respectively), FIGS. 38A, 38A-1 and 38A-3, and 38B (Nm Z4662; SEQ ID No75 and 76, respectively), FIGS. 39A, 39A-1 and 39A-2, and 39B (Nm Z4683; SEQ ID No77 and 78, respectively), FIGS. 40A, 40A-1 and 40A-2, and 40B (Nm Z4673; SEQ ID No79 and 80, respectively), FIGS. 41A, 41A-1 and 41A-2, and 41B (Nm Z4667; SEQ ID No81 and 82, respectively), FIGS. 42A, 42A-1 and 42A-2, and 42B (Nm Z5005; SEQ ID No83 and 84, respectively), FIGS. 43A, 43A-1 and 43A-2, and 43B (Nm Z6466; SEQ ID No85 and 86, respectively), FIGS. 44A and 44A-1, and 44B and 44B-1 (Nm 26904; SEQ ID No87 and 88, respectively), FIGS. 45A, 45A-1 and 45A-2, and 45B (Nm Z7176; SEQ ID No89 and 90, respectively), for tolC (respectively TolC).

Below is illustrated the high identity % observed for each of these compounds when comparing different Nm strains tested.

TABLE 3

Identity (%) between the fhuA DNA sequences (5 alleles) of the different Nm strains tested. Only intact gene sequences have been compared (no pseudogenes)

| | Z4683 | Z4259 | Z6904 | Z7176 |
|---|---|---|---|---|
| Z2491 | 97.2 | 96.9 | 96.2 | 98.7 |
| Z4683 | | 96.5 | 96.1 | 98.2 |
| Z4259 | | | 98.9 | 98.0 |
| Z6904 | | | | 97.0 |

TABLE 4

Identity/similarly (%) between the FhuA proteins of the different Nm strains tested.

| | Z4683 | Z4259 | Z6904 | Z7176 |
|---|---|---|---|---|
| Z2491 | 98.0/98.1 | 97.6/97.9 | 97.0/97.4 | 99.6 |
| Z4683 | | 96.7/97.2 | 96.9/97.2 | 98.4/98.6 |
| Z4259 | | | 99.1/99.3 | 98.0/98.3 |
| Z6904 | | | | 97.4/97.9 |

TABLE 5

Identity (%) between the dsbA DNA sequences (4 alleles) of the different Nm strains tested.

| | Z4662 | Z4259 | Z4683 |
|---|---|---|---|
| Z2491 | 99.9 | 97.7 | 98.0 |
| Z4662 | | 97.6 | 97.8 |
| Z4259 | | | 99.7 |

Nm strains which are below reported as linked by an "=" sign show an identical dsbA sequence.

Z2491=Z3524=Z3842=Z4667=Z4707=Z5005=Z6466Z7176

Z4662=Z6904

Z4259=Z4673

Z4683

TABLE 6

Identity similarly (%) between the DsbA proteins (3 types) of the different Nm strains tested.

| | Z4259 | Z4683 |
|---|---|---|
| Z2491 | 99.8/98.3 | 98.3/98.7 |
| Z4259 | | 99.6 |

Nm strains which are below reported as linked by an "=" sign show an identical dsbA sequence.

Z2491=Z3524=Z3842=Z4667=Z4707=Z5005=Z6466=Z7176=Z4662=Z6904

Z4259=Z4673

Z4683

TABLE 7

Identity (%) between the tolC DNA sequences (4 alleles) of the different Nm strains tested.

| | Z4259 | Z4683 | Z4707 |
|---|---|---|---|
| Z2491 | 99.8 | 99.7 | 99.9 |
| Z4259 | | 99.9 | 99.6 |
| Z4683 | | | 99.6 |

Nm strains which are below reported as linked by an "=" sign show an identical dsbA sequence

Z2491=Z3524

Z4259=Z6904=Z3842=Z7176=Z6466=Z5005=Z46773=Z4667=Z4662

Z4683

Z4707 (pseudogene with a 4 pb deletion which causes a stop codon after 16aa)

Identity/similarly between the TolC proteins (2 types) of the different NM strains tested.

Nm strains which are below reported as linked by an "=" sign show an identical dsbA sequence Z2491 compared to Z4259: identity=similarly=99,8%

Z2491=Z3524

Z4259=Z6904=Z3842=Z7176=Z6466=Z5005=Z4673=Z4667=Z4662=Z4683

The 45 polynucleotides herein illustrated thus appear as covering the Nm genetic diversity, as assessed by said MLST standard test. The person skilled in the art can further verify this Nm genetic diversity coverage by standard polynucleotide detection tests (e.g. with the help of said SEQ ID No: 97-116 primers) performed in any other statistically significant Nm panel, and observe that said Nm polynucleotides are present in more than 90%, preferably more than 95%, more preferably in 100% of the Nm panel.

Each of said 45 Nm polynucleotides (ORF) were assessed for homologies to known proteins using standard BLAST programs as described in the below "definitions" section.

These results are illustrated in the below table 8.

TABLE 8

Open reading frames common to all Nm strains tested, and their correspondance (BLAST hits) with known proteins

| | | Known protein | | | | | |
|---|---|---|---|---|---|---|---|
| ORF | length (aa) | function | species | length (aa) | P | % identity/ % similarity | Accession # |
| fhaB | 2015 | filamentous hemagglutinin B precursor | *B. pertussis* | 3591 | 1e−50 | 25/42 | P12255 |
| rth17 | 181 | gene 25 | phage SPP1 | 271 | 4e−04 | 28/39 | X97918 |
| ORFs with no significant hit (length in aa) rth18 (78), rth19 (155), rth20 (101), rth21 (115) | | | | | | | |
| tolC | 467 | outer membrane protein | *E. coli* | 495 | 5e−20 | 23/40 | P02930 |
| fhuA | 703 | ferrichrome iron receptor | *E. coli* | 747 | 5e−26 | 23/40 | P06971 |
| dsbA | 231 | disulfide oxidoreductase | *P. syringae* | 214 | 3e−18 | 28/47 | AF036929 |
| rni5 | 230 | MTH939, unknown function | Methanobacterium | 188 | 1e−7 | 27/47 | AE000868 |

The products according to the invention thus appear as novel compounds.

EXAMPLE 2

Efficacy of the Products According to the Invention such as DsbA (SEQ ID No:2) from *Neisseria meningitidis* for the Production of Anti-Meningococcal Vaccines In order to be considered as a good vaccine candidate against endemic meningococcal infections, a purified protein has to induce protective antibodies against a wide range of strains representative of the meningococcal population. Subsequently, to be considered as a vaccine candidate a protein has to be immunogenic, to be expressed on the outer membrane, and to induce protective antibodies. In this example (i) we demonstrate that DsbA is expressed in a set of NM strains representative of the meningococcal population by northern blots, (ii) we purified the protein and raised antibodies in rabbit, (iii) using this polyclonal antibody and immunofluorescence of whole bacteria we localised the protein on the outermembrane, (iv) we engineered a non polar mutation and using this mutant we demonstrate that the anti DsbA polyclonal antibody has a bactericidal activity against the wild type strain and not against the isogenic mutant. In this example, DsbA (SEQ ID No:2) was purified as a recombinant protein lacking the signal sequence associated with a hexahistidine tract only in order to facilitate purification. The same procedure can be implemented by the skilled person with any preparation of DsbA isolated directly from *Neisseria meningitidis*, by immunological or biochemical means and all other recombinant forms of the protein, or similarly with any product according to the invention.

I. Northern Blot

Controls of the presence of said recombinant DsbA in every MLST Nm strain have been performed by Northern blot analysis, as below detailed. These controls have confirmed said DsbA covers Nm genetic diversity, as e.g. illustrated by FIG. 49 (Northern blots lanes are given in the below table 9). The marker used was the RNA molecular weight marker I, digoxigenin-labeled, from Boehringer, with 9 fragments, the sizes are indicated in the blot.

Bacteria

TABLE 9

| lane | strain |
|---|---|
| 1 | Nm, serogroup A, subgroup IV-1 |
| 2 | Nm, serogroup A, subgroup III |
| 3 | Nm, serogroup A, subgroup I |
| 4 | Nm, serogroup A, subgroup VI |
| 5 | Nm, serogroup A, subgroup IX |
| 6 | Nm, serogroup C, ET-37 complex, FAM18 |
| 7 | Nm, serogroup W135, ET-37 complex, ROU |
| 8 | Nm, serogroup B, ET-5 complex, 44/76 |
| 9 | Nm, serogroup B, ET-5 complex, MC58 |
| 10 | Nm, serogroup B, Lineage 3 |
| 11 | Nm, serogroup B, A4 cluster |
| 12 | Nm, serogroup B, ST25 |
| 13 | Nm, serogroup B, ST30 |
| 14 | Nm, serogroup B, ST48 |
| 15 | Nm, serogroup B, ST49 |
| 16 | Ng, FA1090 |

The *Neisseria meningitidis* strains chosen for RNA analysis represent the genetic diversity of this species according to multilocus sequence typing (MLST) (Maiden et al., 1998).

Isolation of Total RNA from *Neisseria*

Bacteria were grown on supplemented GC plates overnight at 37° C., 5% $CO_2$, 95% humidity. Single colonies were inoculated in 5 ml supplemented GC medium and grown at 37° C., 180 rpm until an optical density of Klett 50 was reached. 4 ml bacterial culture was pelleted by centrifugation (5000 rpm, 10 min).

RNA isolation was performed using the RNAqueous Kit (Ambion, Austin, Tex., USA) according to the manufacturer's protocol: The bacterial pellet was resuspended in 350 µl Lysis/Binding Solution. 400 µl 64% ethanol were added and mixed by repeated pipetting 400 µl of the lysate/ethanol mixture were applied to a filter cartridge and centrifuged in a microcentrifuge for 1 min. The flow-through was discarded and the remaining lysate/ethanol mixture was centrifuged through the filter. The filter cartridge was once washed with 700 µl Wash Solution #1 and twice with 500 µl Wash Solution #2/3. The wash solutions were passed through the filter by centrifugation for 1 min; the last traces of wash solution were removed by 2 min centrifugation after the last washing step. The filter cartridge was transferred to a fresh collection tube and 60 µl of elution solution was added to the center of the filter. The cartridge was incubated in a heat block at 65° C. for 10 min and the eluate was recovered by centrifugation for 1 min. This elution step was repeated with another 60 μl of elution solution. The concentration of the RNA was measured in a 1:10 dilution in elution solution. The average RNA yield was around 1.5 μg/μl. RNA was stored at −80° C.

RNA Electrophoresis and Transfer (Northern Blot)

A 1% denaturing agarose gel was prepared by dissolving 0.5 g agarose in 40.5 ml $H_2O$ and cooling to 60° C. 5 ml 10×MOPS buffer (0.2 M MOPS, pH 7.0, 0.05 M sodium-acetate, 0.01 M EDTA) and 4.5 ml formaldehyde (37%) were added and the gel was poured (gel size: 13 cm×7.5 cm). 1×MOPS was used as running buffer.

The RNA samples (ca. 3 μg per lane) were mixed with 4 volumes of gel loading solution (supplied with the RNAqueous Kit) containing. 10 μg/ml ethidium bromide. The samples were heated at 65° C. for 10 min and immediately put on ice. The RNA was loaded and electrophoresis was performed at 5 V/cm until the bromophenol blue band had migrated two thirds of the length of the gel. The gel was photographed and washed for 10 min in $H_2O$ to remove formaldehyde.

The RNA was transferred from the gel to Hybond N+ membrane (Amersham) by capillary transfer (Sambrook et al., 1989) overnight using 20×SSC (3 M NaCl, 0.3 M sodium citrate, pH 7.0) as transfer buffer.

The membrane was shortly washed with 2×SSC and baked between Whatman 3 MM filter paper for 30 min at 120° C.

Hybridization and Detection

The RNA was detected using the DIG system (Boehringer Mannheim).

Labeling of the DNA probe:

Primers specific for the dsbA homolog of strain Z2491 (forward primer: 5'-GCTTTGACTTCATTGACCCTGTTGGCATTGGCC; (SEQ ID No97)

reverse primer: 5'-TATCCACCAACTGGTCAATCGTGGTCATACCGG) SEQ ID No98 were used in PCR amplification with DIG-labeled dUTP. Template chromosomal DNA of strain Z2491 was isolated as described (Sarkari et al., 1994). The PCR reaction mixture contained template DNA (1 μg/ml); reaction buffer (10 mM Tris-Cl, pH 8.0, 50 mM KCl, 1.5 mM $MgCl_2$, 0.01% gelatin); PCR DIG probe synthesis mix (200 μM dATP, dCTP, dGTP each, 190 μM dTTP, 10 μM digoxigenin-11-dUTP; Boehringer); forward and reverse primer (100 nM each) and Taq polymerase. The PCR reaction was incubated 1 min at 94° C, followed by 30 cycles of 1 min at 94° C., 1.5 min at 60° C. and 2 min at 72° C. followed by incubation for 5 min at 72° C. The labeled PCR product was purified using the Qiaquick PCR Purification Kit.(Qiagen).

Hybridization Conditions:

For prehybridization, the membrane was incubated for 2 h at 42° C. with 20 ml of hybridization solution (High SDS Buffer: 7% SDS, 50% formamide, 5×SSC, 2% Bloclcing Reagent (Boehringer), 50 mrM sodium-phosphate, pH 7.0, 0.1% N-lauroylsarcosine) in a hybridization tube. This solution was replaced by 10 ml hybridization solution containing 250 ng of labeled probe. For denaturation, this solution was heated at 68° C. for 10 min before adding. Hybridization was performed overnight at 42° C. After that, the membrane was washed 2×5 min at room temperature with 2×SSC, 0.1% SDS and 2×30 min at 68° C. with 0.5×SSC, 0.1% SDS.

Detection by Chemiluminescence:

After hybridization and washing, the membrane was equilibrated for 1 min in maleic acid buffer (100 mM maleic acid, 150 mM NaCl, pH 7.5). The membrane was blocked by gentle agitation in blocking solution (1% Blocking Reagent (Boehringer) in maleic acid buffer), followed by incubation with antibody solution (Anti-Digoxigenin, Fab fragments conjugated to alkaline phosphatase, 1:10000 in blocking solution) for further 30 min. The membrane was washed 2×15 min with maleic acid buffer and then equilibrated for 2 min, in detection buffer (100 mM Tris-Cl, 100 mM NaCl, pH 9.5). The chemilumescence substrate CSPD was diluted 1:100 in detection buffer. The membrane was treated with CSPD-solution for 5 min at room temperature in a sealed bag. After removing the CSPD-solution, the membrane was sealed again and incubated for 15 min at 37° C. The membrane was exposed to X-ray film for 1 h.

II. Creation of an Isogenic DsbA Mutant of meningococci

Oligonucleotides were designed to amplifier DNA fragments extending about 1 kilobase on either side of the first cysteine codon in dsbA (SEQ ID No1) (This cysteine is immediately after the predicted site of proteolytic cleavage in the maturation of the protein DsbA). Oligonucleotides were designed such that a ligation of the two fragments recreates the DNA sequence of DsbA and some flanking sequence, with the exception that there is an EcoRI restriction endonuclease site (an EcoRI site) in place of the DNA sequence coding for the predicted protease recognition site, the first cysteine codon is no longer present, there is an in-frame translational stop codon and the transational frame of the rest (3') of the gene is shifted by one base.

Oligonucleotides used to amplify the 5' end of the DsbA gene plus upstream sequence were:

```
b31331:
GAACATGGATCCCGTCCACACACTTTACG      (SEQ ID N°91)

b31311:
GCGGCCGAATTCCAACAGGGTCAATGAAGT     (SEQ ID N°92)
```

Oligonucleotides used to amplify the 3' end of DsbA plus downstream sequence were

```
b31312:
CTGTTGGAATTCGGCCGCTTGTAGCAAACAGGCT   (SEQ ID N°93)

b31313:
TAGTACGGTACCGATTCACTTGGTGCTT         (SEQ ID N°94)
```

In order to mutate the dsbA gene PCR amplification was performed using chromosomal DNA from strain 8013 (a serogroup C clinical isolate) as template.

Oligonucleotides b31311 and b31312 contain complementary sequences, such that mixture of the two PCR products in the presence of the two 'external' oligonucleotides b31331 and b31313 results in 'PCR ligation' forming the DNA fragment extending from the position of b31331 to that of b31313, and including the modifications described above. This fragment was cleaved with the enzymes BamHI and KpnI and cloned into appropriately cleaved vector pBluescript II SK(+), which was then propagated in *E. coli* DH5α. This construction was linearised by digestion with EcoRI. Into the EcoRI site was inserted a resistance cassette containing a gene encoding resistance to erythromycin and two neisserial uptake sequences (GCCGTCTGAA) which have been shown to be necessary for efficient transformation of Nm [Goodman, S. D., and Scocca, J. J. (1988). Identification and arrangement of the DNA sequence recognized in specific transformation of *Neisseria gonorrhoeae. Proc. Natl. Acad Sci. USA* 85, 6982-6986]. The plasmid containing the dsbA gene interrupted by the erythomycin resistance cassette was used to transform Nm to erythromycin resistance, selecting on 2 μg/ml erythromycin. Chromosomal DNA, prepared from a selected transformant strain was used to back transform the parental strain 8013 (serogroup C; see Nassif X., D. Puaoi, and M. So. Transposition of Tn1545-*3 in the pathogenic *Neissria: a genetic tool for mutagenesis, Journal of Bacteriology,* 1991, 173, 2147-2154) and several hundred transformant colonies were taken to give a statistically homogeneous genetic background.

The transformant strain was tested by western blot in order to show that it no longer expressed the protein DsbA, using either rabbit anti-whole cell (strain Z5463) or anti-DsbA antiserum.

The overall strategy is illustrated by FIG. 46 which shows the production of a knockout mutation of DsbA. On this figure, ORF are shown as arrows (note that the sequence shown is that of Z2491 and that strain 8013 does not contain the ORF rei1; the PCR product b31331-31311 is correspondingly shorter). The position of the oligonucleotide primers are shown as small arrows. PCR products are shown as shaded boxes. The two PCR products were ligated (FIG. 46*a*) and cloned into the vector pBluescript. After linearisation of the plasmid by cleavage with EcoRI, the resistance cassette (dark grey) was inserted (FIG. 46*b*). This construction was used to transform Nm to erythromycin resistance (FIG. 46*c*), thus replacing the wild-type dsbA gene with that interrupted with the resistance cassette.

III. Cloning and Expression of DsbA for use in Production of Anti-DsbA Antiserum Overview of cloning strategy. The antigen DsbA is predicted to be a lipoprotein, whose lipophilic signal sequence is cleaved to leave an N-terminal cysteine residue which is subsequently modified by the addition of (a) fatty acid molecule(s) for anchorage in the outer membrane [Pugsley, A. P. (1993). The complete general secretory pathway in Gram-negative bacteria. *Microbiol. Rev.* 57, 50-108]. This signal sequence is not present in the mature protein. After cloning and overexpression of the gene, if the protein were exported in large quantities to the outer membrane of the host *E. coli* it could prove toxic for the bacteria. On the basis of these considerations, the gene was not cloned in its entirety, but only the sequence coding for the predicted mature protein was cloned and expressed. In order to minimise the metabolic load on the host bacteria, the (codon for the) N-terminal cysteine of the mature protein was replaced by a (codon for a) serine.

Primers were designed in order to amplify DNA corresponding to the predicted mature protein DsbA and to allow subsequent ligation into an expression vector which links the protein at its C-terminal end to a hexahistidine tract (His-tag) in order to facilitate subsequent purification, using a nickel affinity column.

Oligonucleotides b31316b (GCTTGTGGTACCATATGAGCAAACAGGCTGAAACCAGT; SEQ ID No95)

and b31317 (TCAATCCTCGAGTTGCGGCTTTTTCTGCTCTT;

SEQ ID No96) were designed to amplify a fragment from the chromosome of Nm strain Z2491. Oligonucleotide b31316b contains a recognition site for the restriction endonuclease NdeI (CATATG) allowing the fragment to be cloned into the expression vector pET20b(+) (Novagen R&D systems). The latter half of this site specifies the amino acid methionine, which is the N-terminal amino acid of the expressed protein. This is followed by a codon specifying serine (which was chosen to replace the N-terminal cysteine of the mature protein) and subsequently by bases corresponding to the gene sequence. The oligonucleotide b31317 causes the replacement of the gene's natural stop codon with the first three bases of an XhoI site (CTCGAG), which allows an in frame link to the expression vector's hexahistidine encoding sequence. Translation is terminated after the hexahistidine by a stop codon in the vector.

Overview of strategy for overexpression of the cloned protein. The expression vector takes advantage of an NdeI site to allow insertion of a coding DNA sequence such that the second half of this site (ATG) is recognised by the ribosome as the first amino acid of the recombinant protein to be expressed. Since cleavage by the enzyme NdeI is particularly inefficient near the extremity of a PCR product, it is easier to clone the PCR product using another method (either using a site incorporated into the oligonucleotide 5' to the NdeI site, by 'TA cloning', or by enzymatically blunting the fragment and ligating into a 'blunt-ended' restriction ezyme site) then excise the coding fragment using the enzymes NdeI and that at the 3' end of the gene). This fragment is then ligated into the expression vector and the resulting plasmid grown in *E. coli* strain DH5α, which is highly transformable and will not be harmed by the expression of the potentially toxic foreign protein since it is incapable of initiating transcription from the T7 RNA polymerase promoter in the expression vectors. Plasmid isolated from DH5α is then used to transform (at high efficiency) *E. coli* strain BL21(DE3). This strain contains a gene for T7 RNA polymerase preceded by the lac promoter and hence inducible by isopropyl b-D-thiogalactoside (IPTG). Addition of IPTG to the culture medium induces the transcription of the T7 RNA polymerase gene. The recombinant protein gene is read by the T7 RNA polymerase, and the transcript translated to overproduce the recombinant protein.

Cloning of the DsbA gene. The PCR products from b31316b and b31317 using chromosomal DNA as template were blunted (using the Klenow fragment of *E. coli* DNA polymerase and T4 phage polynucleotide kinase in the presence of the four deoxynucleotide triphosphates and ATP) and ligated into the SmaI site of plasmid pUC18. The ligation mixtures were used to transform *E. coli* DH5α, and the resulting plasmid were cleaved with NdeI and XhoI. The liberated fragment was gel purified and ligated into the expression vector pET-20b(+). The ligation mixture was used to transform *E. coli* DH5α, then plasmid was isolated and used to transform BL21(DE3). Individual colony isolates were screened for production of the recombinant protein by SDS-PAGE. One isolate was chosen for subsequent use in protein purification. This isolate was designated 2g:

| Name | *E. coli* strain | construction | expressed protein |
|---|---|---|---|
| 2 g | BL21 (DE3) | pET20b(+):PCR product b31316b-b31317 | DsbA-(C-terminal his tag) |

Purification of the recombinant proteins. Recombinant DsbA protein was purified using an affinity column produced with Poly-His protein purification resin. Bacteria (20 to 50 isolated colonies of overnight growth on LB agar containing 100 mg/ml of ampicillin) were inoculated into 500 ml of LB medium containing 100 mg/ml of ampicillin and incubated at 37° C. in a conical flask with orbital shaking to maintain aeration. When the OD at 600 nm of the culture had reached between 0.4 and 0.5, the expression of the protein was induced by addition of IPTG to 2 mM. Growth was continued for a further 2 hours, then the bacteria were harvested by centrifugation at 3500×g for 25 minutes. The pellets were sonicted (three times 5 minutes, on ice) in 10 ml of PBS to break the cells. The suspension was centrifuged at 15000×g and the supernatant taken. For purification, 5 ml of the supernatant was passed through a column made from 1 ml of 'poly-His protein purification resin' (Boehringer Mannheim). The column was washed with 5 ml of PBS containing 10 mM imidazole, then 5 ml of PBS/20 mM imidazole. The recombinant DsbA protein was eluted in PBS/50 mM imidazole, then PBS/500 mM imidazole. Fractions containing pure recombinant DsbA (by SDS-PAGE analysis) were pooled and dialysed against PBS. Stocks containing recombinant DsbA at 100 μg/ml were stored at −80° C.

IV. Immunisation of a Rabbit with Recombinant DsbA.

New Zealand white rabbits were immunised three times at intervals of 15 days with 100 μg of recombinant DsbA (preparation 2g).

| | |
|---|---|
| 1st immunisation | 2 ml of antigen '2 g' in PBS:Freund's complete adjuvant (1:1) |
| 2nd immunisation | 2 ml of antigen '2 g' in PBS:Freund's incomplete adjuvant (1:1) |
| 3rd immunisation | 2 ml of antigen '2 g' in PBS:Freund's incomplete adjuvant (1:1) |

Blood was taken from the rabbits 3 weeks after the third immunisation and allowed to clot overnight. Serum was separated from the clot by centrifugation and stored in aliquots at −80C.

V. Immunofluorescence Staining of meningococci

Meningococci were grown for 18 hours on GCB-agar (Difco), then resuspended in PBS. Drops of suspension were immediately placed on glass microscope slides and allowed to dry at 45° C. The bacteria were fixed to the slide by adding methanol and allowing to evaporate (twice). The bacteria were pretreated with PBS containing 1% gelatin, then reacted with the primary antibody (1/1000 dilution of the rabbit anti-recombinant DsbA in PBS/gelatin) for 30 minutes at room temperature. The slides were washed twice for 2 minutes in an excess of PBS, then reacted with 1/200 dilutions the secondary antibody in PBS/gelatin (sheep anti-rabbit immunoglobulin G-Cy3-conjugate) for 30 minutes at room temperature. Slides were washed three times for 5 minutes in an excess of PBS, then the bacteria were counterstained with DAPI (1 μg/ml in PBS/10% methanol) and rinced twice in PBS. The slides were allowed nearly to dry, then the mounting fluid 'morviol' (Sigma) was added to the bacteria and cover slips were fixed in place. The bacteria and fixed antibodies were visualised by ultraviolet and light microscopy.

Anti-DsbA antiserum gave a halo of reacting antibodies around the wild type Nm (8013) which was reduced to the background level of reactivity of the secondary (sheep anti-rabbit immunoglobulin G) antibody alone in the case of the DsbA mutant. Immunofluorescence microscopy of wild-type and DsbA mutant bacteria with anti-recombinant DsbA antiserum, showed wild-type Nm 8013 reacted with anti-DsbA antiserum and revealed with anti-rabbit immunoglobulin G-Cy3 conjugate, and DsbA mutant 8013 reacted with anti-DsbA antiserum and revealed with anti-rabbit immunoglobulin G-Cy3 conjugate.

V. Assay for the Bactericidal Activity of the Rabbit Anti-Recombinant DsbA Antiserum Volumes of 10 μl of PBS containing 2000 bacteria were mixed with 500 μl of freshly- Thawed rabbit serum. Volumes of 95 μl were taken from the assays for enumeration immediately and at time points up to 90 minutes after addition of the serum. Enumeration was performed by plating 50 μl aliqots of 10-fold dilutions of the assays onto GCB agar (Difco).

The results show that while the antiserum killed 65% of the parental meningococcus (strain 8013) within 20 minutes and all of the bacteria within 60 minutes, the preimmune serum (serum taken from the rabbit before the first immunisation) killed none after 20 minutes and only half after 60 minutes. Hence the antiserum is capable of killing heterologous meningococci (The DsbA sequence was taken from strain Z2491). This is illustrated by FIG. 47 which shows the bactericidal activity of anti-DsbA and the corresponding preimmune antiserum.

The bactericidal activity of the antiserum against the parental strain 8013 was compared with that against the isogenic mutant containing an interrupted DsbA gene (and shown by western blot not to express this protein). In this case freshly-thawed anti-recombinant DsbA antiserum was added to the parental and to the DsbA mutant. The results show that the bactericidal activity is specific for the DsbA-expressing strain, since the parental strain was killed to a much greater extent than was the mutant. This is illustrated by FIG. 48, which shows the bactericidal activity of anti-DsbA antiserum against meningococci expressing an isogenic mutant lacking the protein DsbA.

SEQUENCE LISTING BRIEF SUMMARY

| SEQ ID N° | Sequence nature | Nm strain source | product name | |
|---|---|---|---|---|
| | | | | DsbA Allele 1 |
| 1 | nucleotides | Z2491 | dsbA | |
| 2 | aminoacids | Z2491 | DsbA | |
| 3 | nucleotides | Z3524 | dsbA | |
| 4 | aminoacids | Z3524 | DsbA | |
| 5 | nucleotides | Z3842 | dsbA | |
| 6 | aminoacids | Z3842 | DsbA | |
| 7 | nucleotides | Z4667 | dsbA | |
| 8 | aminoacids | Z4667 | DsbA | |
| 9 | nucleotides | Z4707 | dsbA | |
| 10 | aminoacids | Z4707 | DsbA | |
| 11 | nucleotides | Z5005 | dsbA | |
| 12 | aminoacids | Z5005 | DsbA | |
| 13 | nucleotides | Z6466 | dsbA | |
| 14 | aminoacids | Z6466 | DsbA | |
| 15 | nucleotides | Z7176 | dsbA | |
| 16 | aminoacids | Z7176 | DsbA | |
| | | | | DsbA Allele 2 |
| 17 | nucleotides | Z4662 | dsbA | |
| 18 | aminoacids | Z4662 | DsbA | |
| 19 | nucleotides | Z6904 | dsbA | |
| 20 | aminoacids | Z6904 | Dsba | |
| | | | | DsbA Allele 3 |
| 21 | nucleotides | Z4259 | dsbA | |
| 22 | aminoacids | Z4259 | DsbA | |

-continued

| SEQ ID N° | Sequence nature | Nm strain source | product name | |
|---|---|---|---|---|
| 23 | nucleotides | Z4673 | dsbA | |
| 24 | aminoacids | Z4673 | DsbA | |
| | | | | DsbA Allele 4 |
| 25 | nucleotides | Z4683 | dsbA | |
| 26 | aminoacids | Z4683 | DsbA | |
| | | | | FhaB |
| 27 | nucleotides (3' end 1047 ones) | Z2491 | fhaB | |
| 28 | aminoacids | Z2491 | FhaB | |
| | | | | FhuA |
| 29 | nucleotides | Z2491 | fhuA | |
| 30 | aminoacids | Z2491 | FhuA | |
| 31 | nucleotides | Z3524 | fhuA | |
| 32 | aminoacids | Z3524 | FhuA | |
| 33 | nucleotides | Z3842 | fhuA | |
| 34 | aminoacids | Z3842 | FhuA | |
| 35 | nucleotides | Z4259 | fhuA | |
| 36 | aminoacids | Z4259 | FhuA | |
| 37 | nucleotides | Z4662 | fhuA | |
| 38 | aminoacids | Z4662 | FhuA | |
| 39 | nucleotides | Z4667 | fhuA | |
| 40 | aminoacids | Z4667 | FhuA | |
| 41 | nucleotides | Z4673 | fhuA | |
| 42 | aminoacids | Z4673 | FhuA | |
| 43 | nucleotides | Z4683 | fhuA | |
| 44 | aminoacids | Z4683 | FhuA | |
| 45 | nucleotides | Z4707 | fhuA | |
| 46 | aminoacids | Z4707 | FhuA | |
| 47 | nucleotides | Z5005 | fhuA | |
| 48 | aminoacids | Z5005 | FhuA | |
| 49 | nucleotides | Z6904 | fhuA | |
| 50 | aminoacids | Z6904 | FhuA | |
| 51 | nucleotides | Z7176 | fhuA | |
| 52 | aminoacids | Z7176 | FhuA | |
| | | | | Rni5 |
| 53 | nucleotides | Z2491 | rni5 | |
| 54 | aminoacids | Z2491 | Rni5 | |
| | | | | Rth17 à 21 |
| 55 | nucleotides | Z2491 | Rth17 | |
| 56 | aminoacids | Z2491 | Rth17 | |
| 57 | nucleotides | Z2491 | rth18 | |
| 58 | aminoacids | Z2491 | Rth18 | |
| 59 | nucleotides | Z2491 | rth19 | |
| 60 | aminoacids | Z2491 | Rth19 | |
| 61 | nucleotides | Z2491 | rth20 | |
| 62 | aminoacids | Z2491 | Rth20 | |
| 63 | nucleotides | Z2491 | rth21 | |
| 64 | aminoacids | Z2491 | Rth21 | |
| | | | | TolC Allele 1 |
| 65 | nucleotides | Z2491 | tolC | |
| 66 | aminoacids | Z2491 | TolC | |
| 67 | nucleotides | Z3524 | tolC | |
| 68 | aminoacids | Z3524 | TolC | |
| | | | | TolC Allele 2 |
| 69 | nucleotides | Z4707 | tolC | |
| 70 | aminoacids | Z4707 | TolC | |
| | | | | TolC Allele 3 |
| 71 | nucleotides | Z3842 | tolC | |
| 72 | aminoacids | Z3842 | TolC | |
| 73 | nucleotides | Z4259 | tolC | |
| 74 | aminoacids | Z4259 | TolC | |

-continued

| SEQ ID N° | Sequence nature | Nm strain source | product name | |
|---|---|---|---|---|
| 75 | nucleotides | Z4662 | tolC | |
| 76 | aminoacids | Z4662 | TolC | |
| 77 | nucleotides | Z4667 | tolC | |
| 78 | aminoacids | Z4667 | TolC | |
| 79 | nucleotides | Z4673 | tolC | |
| 80 | aminoacids | Z4673 | TolC | |
| 81 | nucleotides | Z4683 | tolC | |
| 82 | aminoacids | Z4683 | TolC | |
| 83 | nucleotides | Z5005 | tolC | |
| 84 | aminoacids | Z5005 | TolC | |
| 85 | nucleotides | Z6466 | tolC | |
| 86 | aminoacids | Z6466 | TolC | |
| 87 | nucleotides | Z6904 | tolC | |
| 88 | aminoacids | Z6904 | TolC | |
| 89 | nucleotides | Z7176 | tolC | |
| 90 | aminoacids | Z7176 | TolC | |
| | | | | PCR oligo |
| 91 | nucleotidic forward primer | Z2491 | dsbA 5' end | dsbA |
| 92 | nucleotidic reverse primer | Z2491 | dsbA 5' end | |
| 93 | nucleotidic forward primer | Z2491 | dsbA 3' end | |
| 94 | nucleotidic reverse primer | Z2491 | dsbA 3' end | |
| 95 | nucleotidic forward primer | Z2491 | dsbA 5' end | |
| 96 | nucleotidic reverse primer | Z2491 | dsbA 3' end | |
| | | | | Primers |
| 97 | nucleotidic forward primer | Z2491 | dsbA | dsbA |
| 98 | nucleotidic reverse primer | Z2491 | dsbA | |
| 99 | nucleotidic forward primer | Z2491 | fhuA | fhuA |
| 100 | nucleotidic reverse primer | Z2491 | fhuA | |
| 101 | nucleotidic forward primer | Z2491 | rni5 | rni5 |
| 102 | nucleotidic reverse primer | Z2491 | rni5 | |
| 103 | nucleotidic forward primer | Z2491 | tolC | tolC |
| 104 | nucleotidic reverse primer | Z2491 | tolC | |
| 105 | nucleotidic forward primer | Z2491 | rth17 | rth17 |
| 106 | nucleotidic reverse primer | Z2491 | rth17 | |
| 107 | nucleotidic forward primer | Z2491 | rth18 | rth18 |
| 108 | nucleotidic reverse primer | Z2491 | rth18 | |
| 109 | nucleotidic forward primer | Z2491 | rth19 | rth19 |
| 110 | nucleotidic reverse primer | Z2491 | rth19 | |
| 111 | nucleotidic forward primer | Z2491 | rth20 | rth20 |
| 112 | nucleotidic reverse primer | Z2491 | rth20 | |
| 113 | nucleotidic forward primer | Z2491 | rth21 | rth21 |
| 114 | nucleotidic reverse primer | Z2491 | rth21 | |
| 115 | nucleotidic forward primer | Z2491 | fhaB | fhaB |
| 116 | nucleotidic reverse primer | Z2491 | fhaB | |

The invention claimed is:

1. An isolated polypeptide comprising the amino acid sequence of SEQ ID NO: 28.

2. An isolated polypeptide consisting of the amino acid sequence of SEQ ID NO: 28.

3. A composition comprising the polypeptide of claim 1 and a carrier.

4. The composition according to claim 3 further comprising a peptide capable of raising a *Neisseria meningitides*—specific immune response in an animal.

5. A composition comprising the polypeptide of claim 2 and a carrier.

* * * * *